US005932222A

United States Patent [19]
Randolph et al.

[11] Patent Number: 5,932,222
[45] Date of Patent: Aug. 3, 1999

[54] MUTANT RESPIRATORY SYNCYTIAL VIRUS (RSV), VACCINES CONTAINING SAME AND METHODS OF USE

[75] Inventors: Valerie B. Randolph, Lincoln Park; Joan C. Crowley, Englewood, both of N.J.

[73] Assignee: American Cyanamid Company, Wayne, N.J.

[21] Appl. No.: 08/059,444

[22] Filed: May 7, 1993

Related U.S. Application Data

[63] Continuation-in-part of application No. 07/871,420, Apr. 21, 1992, abandoned.

[51] Int. Cl.$^6$ .............................. A61K 39/155; C12N 7/08
[52] U.S. Cl. ..................................... 424/211.1; 424/184.1; 424/278.1; 435/237
[58] Field of Search .................................... 424/89, 211.1, 424/278.1, 88; 435/237

[56] References Cited

FOREIGN PATENT DOCUMENTS

| WO 87/04185 | 7/1987 | WIPO . |
| WO 89/02935 | 4/1989 | WIPO . |
| WO 89/04835 | 6/1989 | WIPO . |
| WO 89/05823 | 6/1989 | WIPO . |
| 93/21310 | 10/1993 | WIPO . |

OTHER PUBLICATIONS

Maassab, et al., "Development and characterization of cold–adapted viruses for use as live virus vaccines", Vaccine, vol. 3:355–369 (1985).

Belshe, et al., "Cold Adaptation of Parainfluenza Virus Type 3: Induction of Three Phenotypic Markers", Journal of Medical Virology 10:235–242 (1982).

Murphy, et al., "A Cold–adapted Mutant of Human Parainfluenza Virus Type 3 Is attenuated and Protective in CHimpanzees", Vaccines 90:91–95 (1990).

Friedewald, W. T. et al., "Low–Temperature–Grown RS Virus in Adult Volunteers," *The J. of the American Medical Association* 204(8) :690–694 (1968).

Wright et al., Infection and Immunity, vol. 37, No. 1, Jul. 1982 pp. 397–400.

Pringle et al., Vaccine 1993; 11:473–478.

Crowe et al, Vaccine 1993; 11:1395–1404.

Collins et al, Vaccine 8(2) :164–168, 1990.

Hall et al, J. Infect. Dis. 162:1283–1290, 1990.

Mufson et al, J. Clin. Microbiol 29(1):162–165, 1991.

McIntosh et al *Virology* $2^{nd}$ Ed, Edited by B.N.

Fields et al, Raven Press, N.Y. pp. 1045–1072, 1990.

Hall, C. B. Science 265:1393–1394, 1994.

Mufson et al J. Clinical Microbiology 25(8): 1535–1539 1987.

McKay et al J. Med. Virology 25:411–421, 1988.

Kim et al, "Clinical and Immunological Response of Infants and Children to Administration of Low–Temperature Adapted Respiratory Syncytial Virus," Pediatrics 48(5): 745–755, 1971.

Freymuth et al, "Prevalence of Respiratory Syncytial Virus Subgroups A and B in France from 1982 to 1990" J. of Clinical Microbiology 39(3) :653–655, 1991.

*Primary Examiner*—Laurie Scheiner
*Attorney, Agent, or Firm*—Hamilton, Brook, Smith & Reynolds, P.C.

[57] ABSTRACT

This invention provides cold adapted mutant RSV, specifically, mutant RSV of subgroup A and B. Nucleic acid molecules encoding the mutant RSV of this invention, and immunogenic polypeptides of these mutant RSV also are provided by this invention. Pharmaceutical compositions containing any of the above compositions are provided herein. These are especially useful as vaccines. Further provided by this invention are methods of vaccinating a subject against RSV infection using the pharmaceutical compositions described herein.

15 Claims, 15 Drawing Sheets

FIG. 1A

RSV2B

```
Isolated, Expanded and
Adapted to Cell Culture
(35°C)
```
↓ PRMK x 7

```
Adapted to Vero
(35°C)
```
↓ Vero x 2

```
Plaque Purified
3 Times
(36°C)
```
↓ Vero x 6

```
Expanded
(36°C)
```
↓ Vero x 1

```
Filtered
Expanded
(36°C)
```
↓ Vero x 2

Parent Stocks

```
Master Seed
(36°C)
MK7 VI2b
```
↓ Vero x 1

```
Intermediate Seed
(36°C)
MK7 VI3b
```
↓ Vero x 1

```
Working Seed
(36°C)
MK7 VI4b
```
↓ Vero x 1

F

| DAY | 0 | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|---|
| 86A003 RSV 2B 4.0 PFU | | | | | | | | | | | | | | | | | | | | | |
| NASAL DISCHARGE | 0 | 0 | 0 | 0 | 0 | 0 | 2 | 2 | 0/+ | 0/+ | 2 | 2 | 2 | 1 | 0/+ | 0 | 0 | 0 | 0 | 0 | 0 |
| COUGH | 0 | 0 | 0 | 0 | 0 | 0 | 0 | 2 | 1 | 0 | 1 | 1 | 1 | 0 | 1 | 1 | 1 | 0 | 0 | 0 | 0 |
| 86A004 RSV 2B 5.0 PFU | | | | | | | | | | | | | | | | | | | | | |
| NASAL DISCHARGE | 0 | 0 | 0 | 0 | 0 | 0 | 1 | 1 | 0 | 0 | 1 | 1 | 0 | 0 | 0/+ | 0 | 0 | 0 | 0 | 0 | 0 |
| COUGH | 0 | 0 | 0 | 0 | 0 | 0 | 0 | 0 | 0 | 0 | 1 | 2 | 2 | 1 | 1 | 1 | 1 | 1 | 0 | 0 | 0 |
| 86A001 RSV 2Bp20L 4.0 PFU | | | | | | | | | | | | | | | | | | | | | |
| NASAL DISCHARGE | 0 | 0 | 0 | 0 | 0 | 0 | 0 | 0 | 0 | 0 | 0 | 0 | 0 | 0 | 0 | 0 | 0 | 0 | 0 | 0 | 0 |
| COUGH | 0 | 0 | 0 | 0 | 0 | 0 | 0 | 0 | 0 | 0 | 0 | 0 | 0 | 0 | 0 | 0 | 0 | 0 | 0 | 0 | 0 |
| 86A002 RSV 2Bp20L 5.0 PFU | | | | | | | | | | | | | | | | | | | | | |
| NASAL DISCHARGE | 0 | 0 | 0 | 0 | 0 | 0 | 0 | 0 | 0 | 0 | 0 | 0 | 0 | 0 | 0 | 0 | 0 | 0 | 0 | 0 | 0 |
| COUGH | 0 | 0 | 0 | 0 | 0 | 0 | 0 | 0 | 0 | 0 | 0 | 0 | 0 | 0 | 0 | 0 | 0 | 0 | 0 | 0 | 0 |

Days Post-Infection

FIG. 7B

MUTANT RESPIRATORY SYNCYTIAL VIRUS (RSV), VACCINES CONTAINING SAME AND METHODS OF USE

RELATED APPLICATIONS

The present application is a continuation-in-part of U.S. Ser. No. 07/871,420, filed on Apr. 21, 1992, now abandoned, the disclosure of which is incorporated herein by reference.

BACKGROUND OF THE INVENTION

Throughout this application, various references are referred to in parenthesis to more fully describe the state of the art to which this invention pertains. Full bibliographic information for each citation is found at the end of the specification, immediately preceding the claims. The disclosures of these references are hereby incorporated by reference into the present disclosure.

Respiratory syncytial virus (RSV), a member of the paramyxovirus family, is the leading cause of viral pneumonia and bronchiolitis in infants and young children and is responsible for an estimated 95,000 hospitalizations and 4,500 deaths per year in the United States (IOM report, 1985; Hall and McBride, 1991; McIntosh and Chanock, 1990). Serious disease is most prevalent in infants 6 weeks to 6 months of age and in children with certain underlying illnesses (e.g. immunodeficiencies, congenital heart disease and bronchopulmonary dysplasia). Two major subgroups of RSV have been identified, A and B, as well as antigenic variants within each subgroup (Anderson et al, 1985; Mufson et al, 1985). Multiple variants of each subgroup have been found to cocirculate in epidemics which occur annually during late fall, winter, and spring months (Anderson et al, 1991). Most children are infected by 2 years of age. Complete immunity to RSV does not develop and reinfections occur throughout life (Henderson et al, 1979; Hall et al, 1991). Most infections are symptomatic and are generally confined to mild upper respiratory tract disease. A decrease in severity of disease is associated with two or more prior infections and, in some studies, with high levels of serum antibody, suggesting that protective immunity to RSV disease will accumulate following repeated infections (Lamprecht et al, 1976; Henderson et al, 1979; Glezen et al, 1981; Glezen et al, 1986; Kasel et al, 1987/88; Hall et al, 1991). There is also evidence that children infected with one of the two major RSV subgroups may be somewhat protected against reinfection with the homologous subgroup (Mufson et al, 1987). These observations suggest that it is both possible and worthwhile to develop an RSV vaccination regimen for infants and young children which would provide sufficient temporary immunity to protect against severe disease and death.

The identification of the two major subgroups of RSV has been based on reactivities of the F and G surface glycoproteins with monoclonal antibodies (Anderson et al., 1985; Mufson et al., 1985) and further delineated by sequence analysis (Collins, 1991; Sullender et al., 1991). Both F and G proteins elicit neutralizing antibodies and immunization with these proteins models (Johnson et al., 1987; Stott et al., 1987; Walsh et al., 1987). Most neutralizing antibodies are directed against the F protein. Beeler and Coelingh (1989) reported that out of 16 neutralization epitopes mapped to the F protein, 8 epitopes were conserved in all or all but one of 23 virus isolates tested. A high degree of sequence homology exists between the F protein of subgroups A and B (~90% amino acid and ~80% nucleotide) whereas a much lower degree of homology exists between the G proteins (~50–60% amino acid and ~60–70% nucleotide) (Collins, 1991). Correspondingly, immunity elicited by the F protein is more crossprotective between subgroups than is immunity elicited by the G protein (Johnson et al., 1987; Stott et al., 1987). In mice, humoral immunity induced by both the F and G proteins is thought to be responsible for protection against reinfection with virus (Connors et al., 1991) whereas the CTL response is thought to be more important in resolution of primary infections (Sun et al., 1983; Anderson et al., 1990; Graham et al., 1991). The 22K protein has been shown to be a potent inducer of cytotoxic lymphocytes (CTL) in mice, with lesser CTL recognition of F, N, and P proteins (Oppenshaw et al., 1990; Nicholas et al., 1990). Human CTL's have been shown to recognize the F, 22K, N, M, SH, and 1b proteins (Cherrie et al., 1992). This data suggests that the F proteins of either virus subgroup is a crucial immunogen in any RSV vaccine and that the G, 22K, N, M, SH, and 1b proteins should also be considered potential vaccine components. The benefit for vaccine efficacy in humans of using a live RSV vaccine or incorporating additional viral proteins into a subunit vaccine, and including viruses or proteins of both subgroups, remains to be elucidated.

Early attempts (1966) to vaccinate young children used a parenterally administered formalin-inactivated RSV vaccine. Unfortunately, administration of this vaccine in several field trials was shown to be specifically associated with the development of a significantly exacerbated illness following subsequent natural infection with RSV (Kapikian et al, 1969; Kim et al, 1969; Fulginiti et al, 1969; Chin et al; 1969). The reasons why this vaccine enhanced RSV disease are not clear. It has been suggested that this exposure to RSV antigen elicited an abnormal or unbalanced immune response which led to an immunopathological potentiation of natural disease (Kim et al, 1976; Prince et al, 1986). Following the lack of success with the formalin-inactivated vaccine, emphasis was placed on the development of live attenuated RSV vaccines. Vaccine candidates developed by cold adaptation were reduced in virulence in seropositive adults, however, one vaccine tested in seronegative infants was found to be under-attenuated (Kim et al, 1971; Forsyth and Phillips, 1973). RSV temperature sensitive (TS) mutants derived by chemical mutagenesis (Gharpure et al, 1969) were attenuated in rodent and non-human primate models (Wright et al, 1970; Richardson et al, 1978). Two mutants which initially appeared promising were found to be over- or under- attenuated in seronegative infants and to lack genetic stability (Kim et al, 1973; Hodes et al, 1974; McIntosh et al, 1974; Wright et al, 1976; Wright et al, 1982). Another vaccination approach using parenteral administration of live virus was found to lack efficacy and efforts along this line were discontinued (Belshe et al, 1982). Notably, these live RSV vaccines were never associated with disease enhancement as was the formalin-inactivated RSV vaccine.

Current RSV vaccine development efforts continue for both the live virus and subunit approaches. Because of previous experience with the formalin-inactivated RSV vaccine, trials of vaccines composed of non-replicating viral antigens have proceeded very cautiously. Only one subunit vaccine, purified F protein (PFP, Lederle-Praxis Biologicals) is currently in clinical trials. Studies in seropositive children have thus far given no indication of enhancement of natural disease. Other subunit vaccines in development include baculovirus produced chimeric FG protein (Brideau et al, 1989 [Upjohn]; Wathen et al, 1991 [Upjohn]) and peptides from F and G proteins (Trudel et al, 1991a,b). Vaccine approaches using live-attenuated RSV TS mutants (McKay et al, 1988; Watt et al, 1990) and recombinant vaccinia and adenoviruses expressing RSV F and G proteins (Olmstead et al, 1988; Collins et al, 1990a,b) are also being investigated. Use of a live-attenuated or live-vectored virus vaccine has several advantages over subunit or inactivated virus vaccines. An intranasally administered replicating virus will elicit systemic immunity. In addition, it is more likely than a parenterally administered subunit or inactivated vaccine to give a solid local mucosal immunity comprising both humoral and cellular components. This immunity may confer satisfactory protection from lower respiratory illness, as well as avoiding complications which could lead to enhanced disease.

Cold adaptation, a process by which virus is adapted to growth at temperatures colder than those at which it normally optimally grows, has been used to develop attenuated TS virus mutants for use as vaccines (for review see Maassab and DeBorde, 1985). This method generally results in the accumulation of multiple genetic lesions, unlike chemical mutagenesis in which the genetic lesions are usually single. These multiple lesions may help to confer phenotypic stability by reducing the probability that reversion of any one lesion will result in reversion of the relevant phenotype. Maassab has used stepwise cold adaptation to successfully develop several TS influenza vaccine candidates currently in clinical trials (Maassab et al, 1990; Obrosova-Serova et al, 1990; Edwards et al, 1991). These mutants, which bear attenuating mutations in at least four different genes, appear to be attenuated, immunogenic, and phenotypically stable. Belshe and co-workers have used cold adaptation to develop attenuated, TS strains of a paramyxovirus, parainfluenza virus type 3 (Belshe and Hissom, 1982; Murphy et al, 1990). In this case, cold adaptation was carried out in primary African green monkey kidney cells by reducing temperatures to 20° C. Analysis of several virus variants cloned from this cold adapted population demonstrated that the level of attenuation and temperature sensitivity increased as the length of cold adaptation increased. These variants were shown to have reduced potential for virulence in humans, however the temperature sensitive phenotype was somewhat unstable in clinical trials (Clements et al, 1991). RSV was successfully cold adapted to 25–26° C. in several laboratories in the mid 1960's, but was found to be under-attenuated in vaccine trials (Kim et al, 1971; Maassab and DeBorde, 1985; Forsyth and Phillips, 1973 (Lederle)). Maassab and DeBorde (1985) have suggested this may be because cold adaptation was not carried out at low enough temperatures, or clones of adequately attenuated virus were not isolated from a genetically mixed population of cold adapted virus.

SUMMARY OF THE INVENTION

This invention provides cold adapted mutant RSV, specifically, mutant RSV of subgroup A and B. Nucleic acid molecules encoding the mutant RSV of this invention, and immunogenic polypeptides of these mutant RSV also are provided by this invention. Pharmaceutical compositions containing any of the above compositions are provided herein. These are especially useful as vaccines. Further provided by this invention are methods of vaccinating a subject against RSV infection using the pharmaceutical compositions described herein.

BRIEF DESCRIPTION OF THE FIGURES

FIGS. 1A and 1B show flow chart detailing the propagation of RSV 2B working seed MK7V14b and RSV 3A working seed MK8V17b.

FIGS. 7A and 7B compare the relative growth and pathogenicity of RSV 2B and RSV 2Bp20L in four (4) year old seropositive chimps.

DETAILED DESCRIPTION OF THE INVENTION

Figure 2:
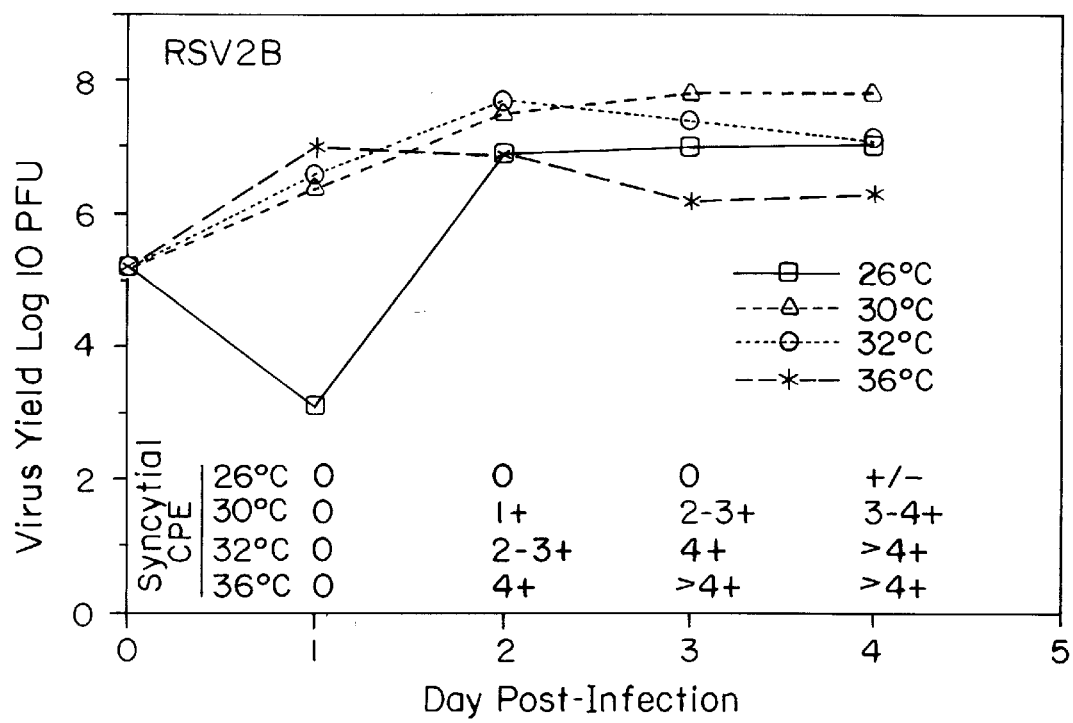
FIG. 2 shows growth and cytopathic effect of RSV 2B at temperatures from 26° C. to 36° C. in Vero cells.

This invention provides a cold adapted mutant respiratory syncytial virus (RSV). This mutant RSV is capable of eliciting an immune response when administered to a subject without causing significant disease, such as respiratory distress or otitis media. As used herein, the term "cold adapted mutant" means an attenuated virus that has been attenuated by propagation at lower than optimal temperatures. Examples of cold adapted mutant viruses have been provided in the background of the invention section, supra. In one embodiment of this invention, the cold adapted mutant RSV is a mutant subgroup A RSV. In a preferred embodiment, the mutant RSV subgroup A virus is a virus selected from the group consisting of 3Ap20E, 3Ap20F and 3Ap28F. Also provided by this invention is a cold adapted mutant RSV, wherein the cold adapted mutant is of the subgroup B. In a preferred embodiment, the cold adapted subgroup B virus is a virus selected from the group consisting of 2Bp33F, 2Bp24G, 2Bp20L and 2Bp34L. The viruses of this invention are useful (1) as live virus vaccines, (2) as a source of genetic material to give, enhance, or stabilize an attenuated phenotype of any RSV strain, (3) as a source of immunogenic polypeptide, (4) as a source of genetic material for recombinant expression of immunogenic polypeptides by a live virus or bacterial vector (e.g. baculovirus, vaccinia virus, adenovirus, attenuated Salmonella), (5) as viral vectors for expression of immunogenic proteins from other viruses, e.g., RSV F and G proteins, influenza HA and NA proteins, parainfluenza HN and F proteins, and (6) as a source of reagents to detect antibody in immunological assays or nucleic acid in enzyme amplification assays (e.g., polymerase chain reaction (PCR)).

This invention also encompasses all derived strains of the above-identified cold adapted mutants of the parental 3A and 2B strains, including, but not limited to those strains attenuated by chemical mutagenesis, cold adaptation, or genetic recombination, e.g. site-directed mutagenesis. These methods are well-known to those of skill in the art.

Vaccines and pharmaceutical compositions containing these virus are described infra.

Purified immunogenic polypeptides isolated from the mutant RSV described hereinabove or from cells infected with these same mutants, also is provided by this invention. As used herein, the term "polypeptide or peptide" is intended to mean a linear polymer of amino acids linked by means of peptide bonds and proteins such as antigenic proteins of RSV. The linear polymers or "protein fragments" may be of various length, as long as the polypeptide is capable of exhibiting immunological activity. Methods of determining immunological activity are described infra.

These polypeptides may be the polypeptides of mutant RSV including the polypeptides designated L, F, G, M, M2 (also known as 22K), P, SH, 1B, 1C or N. These polypeptides may be purified by methods described below and are useful as immunogens in a subunit vaccine to protect against lower respiratory disease and other disease symptoms of RSV infection. The purified RSV immunogenic polypeptides may be linked or conjugated to each other to provide a chimeric (or fusion) polypeptide. Methods of linking polypeptides are well-known to those of skill in the art. Subunit vaccines comprise the relevant immunogenetic material necessary to immunize a host. These vaccines encompass genetically engineered immunogens, chemically synthesized immunogens and/or immunogens comprising authentic substantially pure RSV polypeptides or chimeric polypeptides, alone or in combination with similarly prepared RSV polypeptides or proteins, which are capable of eliciting a protective immune response.

In one embodiment, the RSV polypeptide can be isolated in substantially pure form from RSV or cultures of cells infected with RSV. In an alternative embodiment, the RSV polypeptides can be isolated from a recombinant system or vector engineered to produce these polypeptides. In yet another embodiment, the RSV polypeptide can be chemically synthesized by methods well known to those of skill in the art. The immunogenic polypeptides are most preferably derived from the mutant RSV of this invention. Also within the scope of this invention are polypeptides isolated from wild-type viral strains as well as strains derived from the strains specifically disclosed herein.

As noted above, the mutant RSV polypeptides can be purified from recombinant vectors that express the immunogenic polypeptides. Such recombinants include any of bacterial transformants, yeast transformants, cultured cells infected with recombinant viruses or cultured mammalian cells such as Chinese hamster ovary (CHO) cells. The recombinant polypeptides can comprise multiple copies of the epitope of interest, or the same or different epitopes from different viral subgroups or strains.

Regardless of the method of production, the RSV polypeptide may be used to formulate a vaccine. To do so, the RSV polypeptide is adjusted to an appropriate concentration and formulated with any suitable vaccine adjuvant. The polypeptides can generally be formulated at concentrations in the range of 0.1 ug to 100 ug per kg/host. Physiologically acceptable media may be used as carriers. These include, but are not limited to: sterile water, saline, phosphate buffered saline and the like. Suitable adjuvants include, but are not limited to: surface active substances, e.g., hexadecylamine, octadecylamine, octadecyl amino acid esters, lysolecithin, dimethyl-dioctadecylammonium bromide, N,N-dioctadecyl-N'-N-bis(2-hydroxyethyl-propane diamine), methoxyhexadecyglycerol, and pluronic polyols; polyamines, e.g., aluminum hydroxide, aluminum phosphate, etc. The immunogen may also be incorporated into liposomes or conjugated to polysaccharides and/or other polymers for use in a vaccine formulation.

In yet another embodiment of the invention, the RSV polypeptide is a hapten, i.e., a molecule which is antigenic in that it reacts specifically or selectively with cognate antibodies, but is not immunogenic in that it cannot elicit an immune response. In such case, the hapten may be covalently bound to a carrier or immunogenic molecule; for example, a large protein such as protein serum albumin which will confer immunogenicity to the hapten coupled to it. The hapten-carrier may be formulated for use as a subunit vaccine.

The polypeptides of the present invention may be used when linked to a soluble macromolecular carrier. Preferably, the carrier and the polypeptides or proteins of the present invention are in excess of five thousand daltons after linking. More preferably, the carrier is in excess of five kilodaltons. Preferably, the carrier is a polyamino acid, either natural or synthetic, which is immunogenic in animals, including humans. The manner of linking is conventional. Many linking techniques are disclosed in U.S. Pat. No. 4,629,783 which is incorporated herein by reference. Many cross-linking agents are disclosed in 1986–87 Handbook and General Catalog, Pierce Chemical Company, (Rockford, Ill.) pages 311 to 340, which pages are incorporated herein by reference.

This invention also provides a nucleic acid molecule encoding the cold-adapted mutant RSV or the polypeptides described hereinabove. Also provided is a nucleic acid molecule encoding the chimeric polypeptides. These nucleic acids may be DNA molecules, cDNA molecules or RNA molecules, e.g. anti-sense RNA. The invention also encompasses nucleic acids molecules which differ from that of the nucleic acid molecules which encode these polypeptides, but which produce the same phenotypic effect. These altered, phenotypically equivalent nucleic acids molecules are referred to as "equivalent nucleic acids". This invention also encompasses nucleic acid molecules characterized by changes in non-coding regions that do not alter the phenotype of the polypeptide produced therefrom, when compared to the nucleic acid molecule described hereinabove.

Also provided is a nucleic acid molecule comprising noncoding sequences of the mutant RSV. These non-coding regions are to include 5' noncoding regions, 3' noncoding regions, intergenic sequences, and other noncoding regions of the viral genome. These include, but are not limited to transcriptional, translational, and other regulatory regions. These nucleic acid molecules also may be DNA molecules, cDNA molecules or RNA molecules.

Further encompassed are nucleic acid molecules which hybridize to the nucleic acid molecules of the subject invention under conditions of moderate to high stringency. Multiple factors are important in determining the stringency of a hybridization including species of nucleic acids hybridized, length of nucleic acid probe, $T_M$(melting temperature), temperature of hybridization and washes, salt concentration in the hybridization and wash buffers, aqueous or formamide hybridization buffer, and length of time for hybridization and for washes. An example of moderate to high stringency conditions are DNA-DNA hybridization with a probe greater than 200 nucleotides in aqueous buffer including 0.9M sodium chloride and 0.09M sodium citrate for eighteen hours at 55° C. to 65° C., and washed in buffer containing 0.3M sodium chloride and 0.03M sodium citrate at 42° C.

The nucleic acid molecules of this invention may be operatively linked to a promoter of RNA transcription, as well as other regulatory sequences. As used herein, the term "operatively linked" means positioned in such a manner that the promoter will direct the transcription of RNA off of the nucleic acid molecule. An example of a promoter is the T7 promoter. Vectors which contain both a promoter and a cloning site to which an inserted piece of nucleic acid is operatively linked to the promoter, are well known in the art. Preferably, these vectors are capable of transcribing nucleic acid in vitro and in vivo. Examples of such vectors are nucleic acids of the RSV genome of different types (including other attenuated subtypes) by substituting the nucleic acid regions encoding the polypeptides or the non-coding regions described hereinabove for the nucleic acids of other RSV types such that the resulting virus is more stronger or stably attenuated. Recombinant viral or bacterial vectors engineered to express the mutant RSV immunogenic polypeptides, e.g. vectors of adenovirus, vaccinia virus, poliovirus, influenza virus, parainfluenza virus, salmonella, each of which includes all members of these families.

Further provided are recombinant virus and polypeptides encoded by the nucleic acid molecules of this invention. As used herein, a "recombinant virus" is intended to mean a virus that is genotypically altered from wild-type virus.

Virosomes are artificial lipid envelopes (liposomes) whose membranes contain virus proteins and which encapsulate substances which can include nucleic acids, drugs, proteins and other active compounds. These liposomes may contain RSV envelope proteins from the RSV of this invention. As an example, the G protein of RSV will target the virosome to the respiratory epithelial cells. The F protein will cause fusion of the virosome with the target cell to enable the contents of the virosome to be delivered to the target cell. Virosomes may be administered to the subject intravenously, however, the preferred mode of administration is by aerosol delivery to the lungs e.g., by the use of a nebulizer. Methods of constructing virosome delivery systems are well-known to those of skill in the art. Nucleic acid encoding mutant RSV polypeptides and chimeric polypeptides, can be efficaciously delivered to target cells by a virosome delivery system to act as vaccines in the host.

A host vector system for the production of the recombinant polypeptides described hereinabove and for expressing the nucleic acid molecules of the subject invention are provided. The host vector system comprises one of the vectors described hereinabove in a suitable host. For the purpose of this invention, a suitable host may include, but is not limited to a eukaryotic cell, e.g., a mammalian cell, a yeast cell or an insect cell for baculovirus expression. Suitable mammalian cells may comprise, but are not limited to Vero cells, CHO cells, WI-38 cells and primary monkey kidney cells. The suitable host may also comprise a prokaryotic host cell such as the bacteria cell E. coli.

A pharmaceutical composition comprising any of the cold adapted mutant RSV described above or polypeptides or chimeric polypeptides, alone or in combination, and a pharmaceutically acceptable carrier is also provided by this invention. As used herein, the term "pharmaceutically acceptable carrier" encompasses any of the standard pharmaceutical carriers, such as physiologically balanced culture medium, phosphate buffer saline solution, water, and emulsions, such as an oil/water or water/oil emulsion, various types of wetting agents and protein stabilizer.

In one embodiment of this invention, the pharmaceutical composition is intended for use as a vaccine. In one embodiment a virus may be mixed with cryoprotective additives or stabilizers such as proteins (e.g., albumin, gelatin), sugars (e.g., sucrose, lactose, sorbitol), amino acids (e.g., sodium glutamate), saline, or other protective agents. This mixture is then dessicated or lyophilized for transport and storage and mixed with water immediately prior to administration. Alternatively, the virus may be inactivated by formalin or heat, and mixed with an adjuvant such as aluminum hydroxide, saline and a detergent such as phosphate Tween buffer. For methods of vaccine preparation, see Duffy, (1982).

Pharmaceutical compositions comprising any of the cold adapted mutant RSV, nucleic acid molecules encoding mutant RSV, the immunogenic polypeptide, or the chimeric polypeptide, or live vectors capable of expressing RSV polypeptides, is useful to vaccinate a subject against RSV infection. The scope of this invention is meant to include maternal immunization. Thus, this invention further provides a method of vaccinating a subject against RSV infection by administering to the subject an effective immunizing amount of a pharmaceutical composition described hereinabove.

This subject may be animal, for example a mammal, such as a chimp or preferably a human. A sufficient amount of the vaccine must be administered to the subject to elicit an immune response. Persons skilled in the art will readily be able to determine such amounts. Administration may be by any effective form, such as intranasally, parenterally, intravenously, orally, or topically applied to any mucosal surface such as intranasal, oral, eye or rectal surface. In the preferred embodiment of this invention, live viral vaccines are administered intranasally, orally parenterally or applied to any mucosal surface (nasal, oral, eye, rectal) as described hereinabove. Inactivated whole virus vaccine is preferably administered parenterally or to any mucosal surface.

A method for producing a recombinant polypeptide described hereinabove, is also provided, which comprises growing the cell containing nucleic acid of this invention and/or the host vector system of this invention under suitable conditions, permitting production of the polypeptide and recovering the resulting recombinant polypeptide produced.

Also provided by this invention is a substance capable of specifically forming a complex with a purified polypeptide, or chimeric polypeptide described hereinabove or the mutant attenuated cold adapted RSV. In one embodiment of this invention, the substance is an antibody, such as a monoclonal antibody or chimeric antibody. In the preferred embodiment of this invention, the monoclonal antibody is a human monoclonal antibody.

This invention further provides a method to attenuate a virus by cold-adaptation.

Samples of mutant RSV of this invention have been deposited with the American Type Culture Collection (ATCC) 12301 Parklawn Drive, Rockville, Md., U.S.A. 20852, on Mar. 19, 1992, under the provisions of the Budapest Treaty for the Deposit of Microorganisms for the Purposes of Patent Procedures ("Budapest Treaty"). The virus were accorded the following ATCC designation numbers: 2Bp33F(VR 2364), 2Bp24G(VR 2370), 2Bp20L(VR 2368), 2Bp34L(VR 2365), 3Ap20E(VR 2369), 3Ap20F(VR 2367), and 3Ap28F(VR 2366).

EXEMPLIFICATION

Passage and Characterization of RSV 2B and RSV 3A Parental Strains

RSV 2B and RSV 3A parental strains were isolated and passed in qualified cell lines and under conditions consistent with use as clinical study material.

Two RSV strains, 20648 and 23095, were isolated by Dr. Robert Belshe (Marshall University School of Medicine, West Virginia) from nasal swab samples taken from ill children. These viruses were later recovered from the original frozen nasal swab samples, passed 2 to 3 times in primary rhesus monkey kidney (PRMK) cells, and then sent to applicants.

Isolate 20648 (subgroup B) was renamed RSV 2B. Virus was passed 7 times in PRMK cells at 35° C., 2 times in Vero cells at 35° C. and plaque purified and amplified 3 times (6 passages) in Vero cells at 36° C. Virus was further amplified an additional 2 times in Vero (36° C.), stocks were filtered with a 0.2 m filter and amplified another 2 times in Vero cells. This was followed by production of a Master Seed (RSV 2B, MK7 V12b), Intermediate working seed (RSV 2B, MK7 V13b) and Working seed (RSV 2B, MK7 V14b). See FIG. 1.

Isolate 23095 (subgroup A) was renamed RSV 3A. RSV 3A was passed 8 times in PRMK cells at 35° C. This was followed by 2 passages in Vero at 35° C. and 6 passages in Vero cells at 36° C., including 3 plaque purification steps. Virus was further passaged 6 times in Vero cells at 36° C. including a 0.2 m filtration step. This was followed by production of a Master seed (RSV 3A, MK8 V15b), Intermediate working seed (RSV 3A, MK8 V16b), and Working seed (RSV 3A, MK8 V17b). See FIG. 1.

Subgroup specificities of RSV 2B and RSV 3A Master seeds were confirmed using subgroup specific monoclonal antibodies. Virus stocks were shown to be free of microbial contaminants and adventitious agents.

The F, N, and G proteins of RSV 2B and RSV 3A stocks and reference RSV strains A2, Long, and 18537 were analyzed by radioimmunoprecipitation (RIP) and western blotting procedures using monoclonal antibodies. The F1 subunits of the RSV subgroup B strains, 2B and 18537, migrated faster on SDS-polyacrylamide gels than did the F1 subunits of the RSV subgroup A strains, 3A and Long. No difference in migration of the N proteins of the RSV 2B and 3A strains and the reference strains was seen. In RIP gels, the G protein was visible as two bands at ~80–90 Kda and ~45 Kda. The 80–90 Kda bands of RSV 3A and Long comigrated; however, the 80–90 Kda band of RSV 2B also appeared to comigrate with the subgroup A species rather than with the faster RSV 18537 (subgroup B1). This suggests that RSV 2B may be a member of the B2 subgroup as described by Akerlind et al., 1988. In western blots, the relative proportions of 80–90 Kda and 45 Kda bands were roughly equal for RSV Long, A2, 2B, and 18537 grown in Vero cells, but staining of the 80–90 Kda band of RSV 3A was significantly greater, suggesting a difference in processing of the G protein for this strain when grown in Vero cells. These data demonstrate that the apparent $M_r$ for the RSV 2B and RSV 3A strains are consistent with current subgroup classifications of RSV, but confirm that these strains are not identical to the prototype RSV reference strains.

Growth of RSV 2B, RSV 3A and RSV A2 in mice and in cotton rats was compared. Both RSV 2B and RSV 3A replicated poorly in Balb/c mice compared to the RSV A2 reference strain. Consistent recovery of RSV 2B and RSV 3A could only be obtained at the highest inoculum dose used ($10^{6.0-6.2}$ PFU), and was similar in magnitude to recovery of RSV A2 at a 100-fold lower inoculum ($10^{4.3}$ PFU). In contrast, growth of RSV 2B in cotton rat nose and lungs was similar to growth of RSV A2. Growth of RSV 3A in the nose was similar to the other strains; however growth in lungs was significantly poorer. Both mouse and cotton rat growth data indicate that RSV 2B and RSV 3A have significantly different in vivo growth characteristics than the RSV A2 reference strain, as well as differing from each other.

Cold Adaptation of RSV

Figure 3:
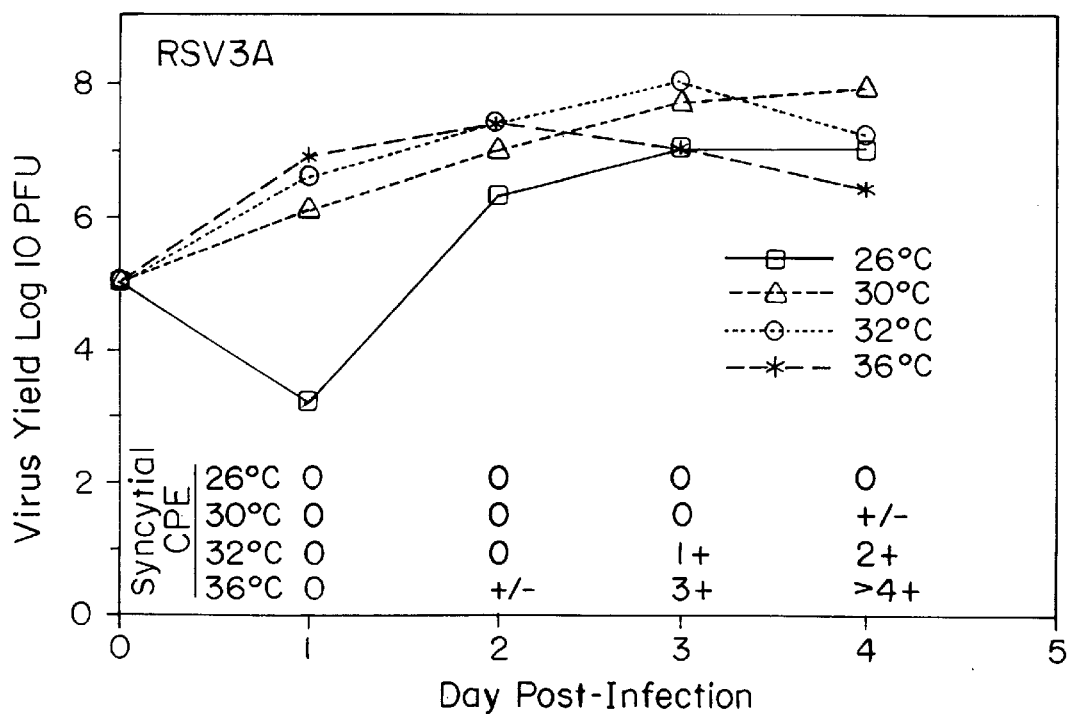
FIG. 3 shows growth and cytopathic effect of RSV 3A at temperatures from 26° C. to 36° C. in Vero cells.
Figure 4A:
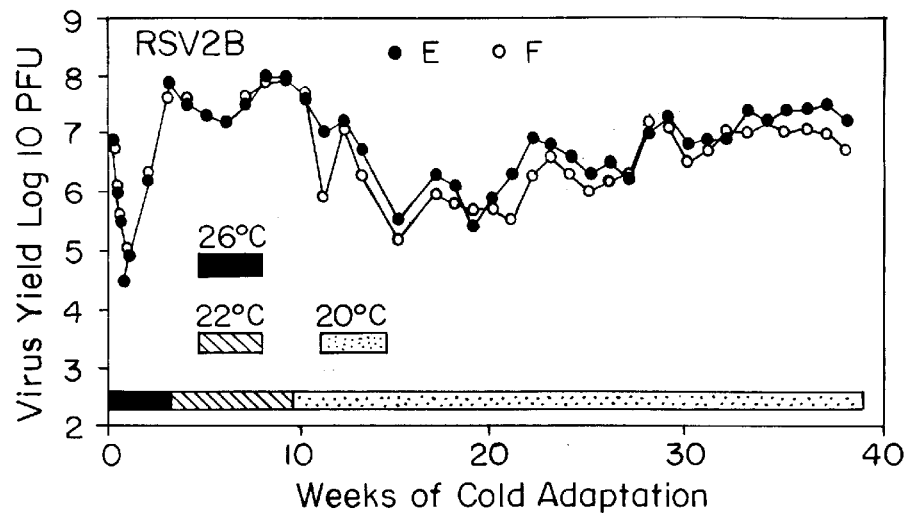
FIGS. 4A–4F graphically show titration results obtained at each passage of RSV 2B and RSV 3A.
Figure 4B:
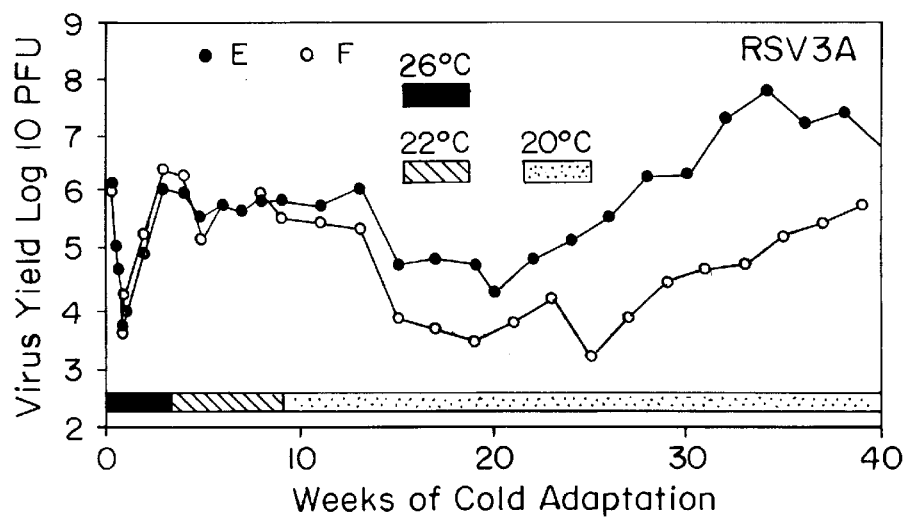
Figure 4C:
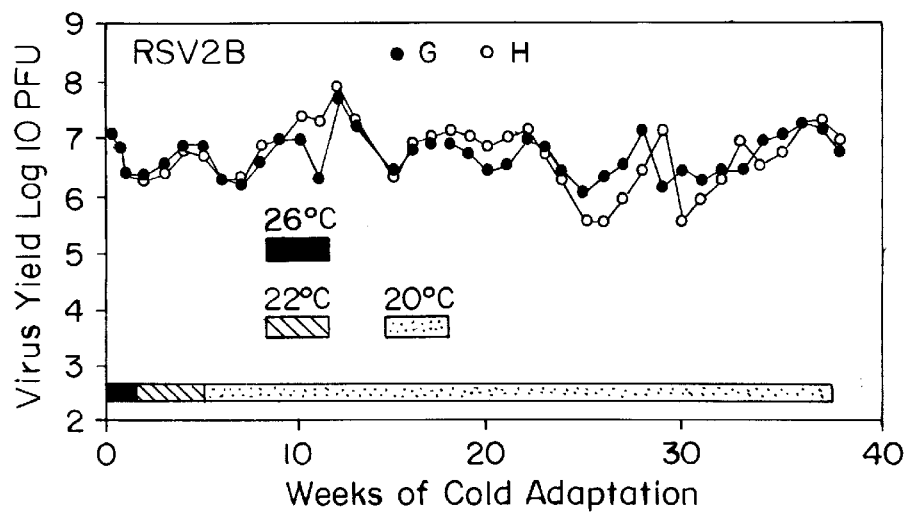
Figure 4D:
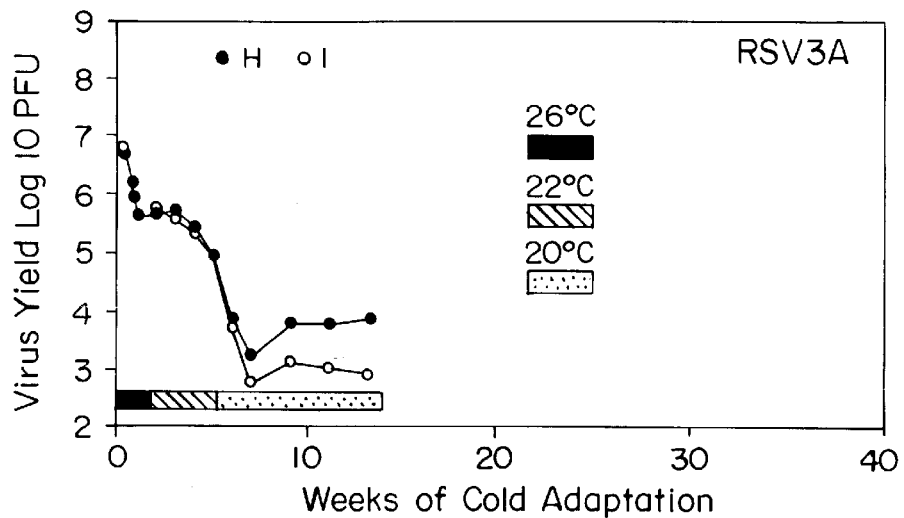
Figure 4E:
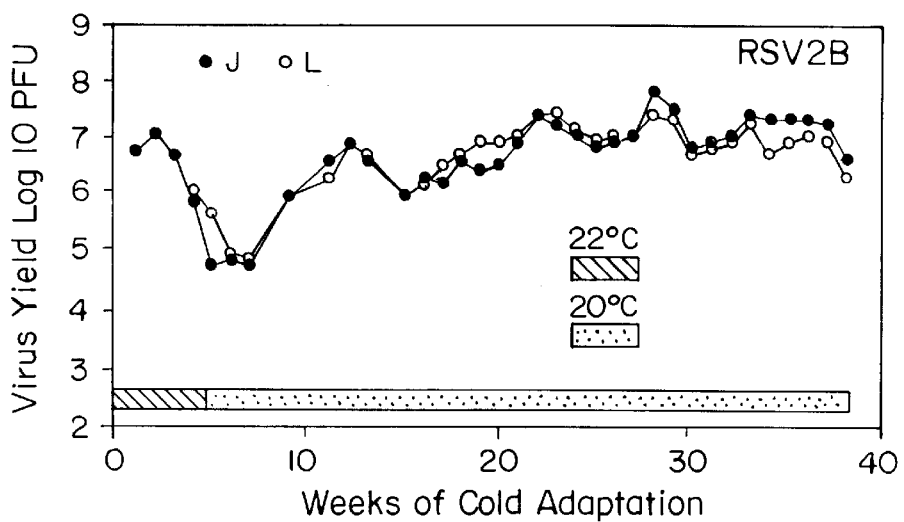
Figure 4F:
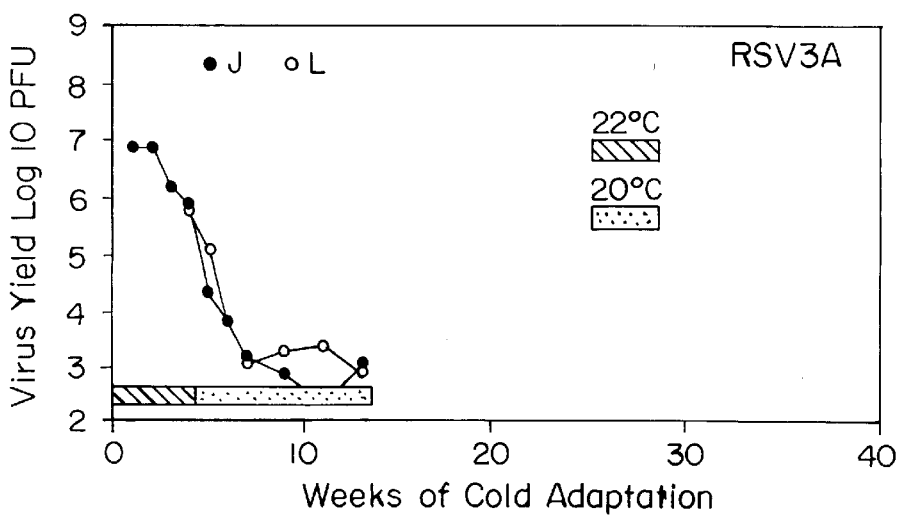
Figure 5A:
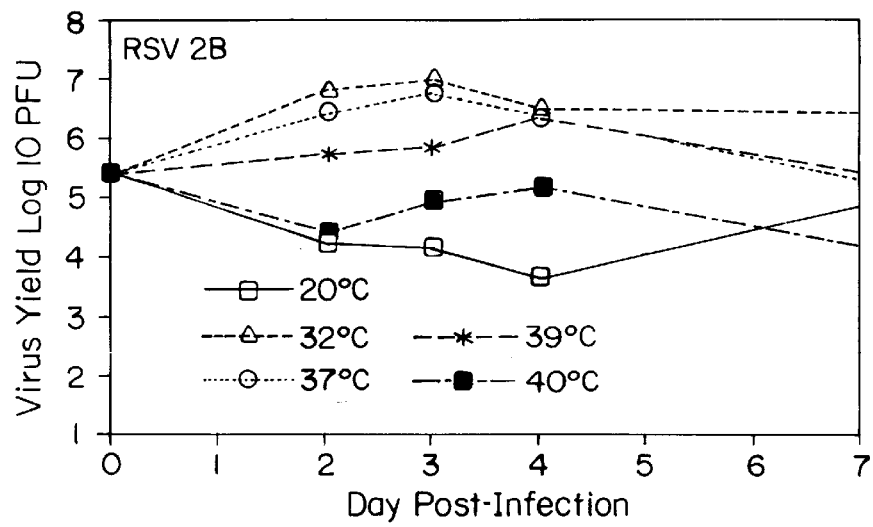
FIGS. 5A–5F show the growth curves of RSV 2B, RSV 2Bp24G, RSV 2Bp20L, RSV 3A, RSV 3Ap20E and RSV 3Ap20F in Vero cells at temperatures from 20° C. to 40° C.
Figure 5B:
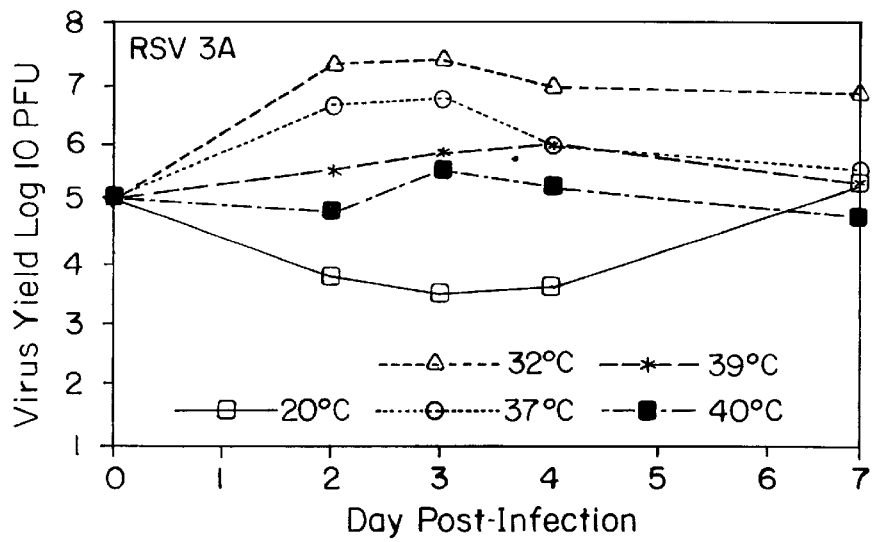
Figure 5C:
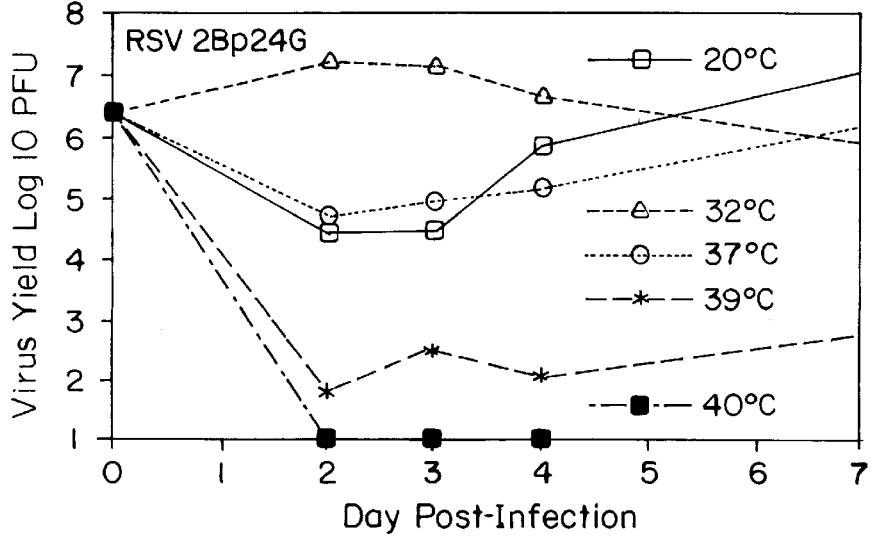
Figure 5D:
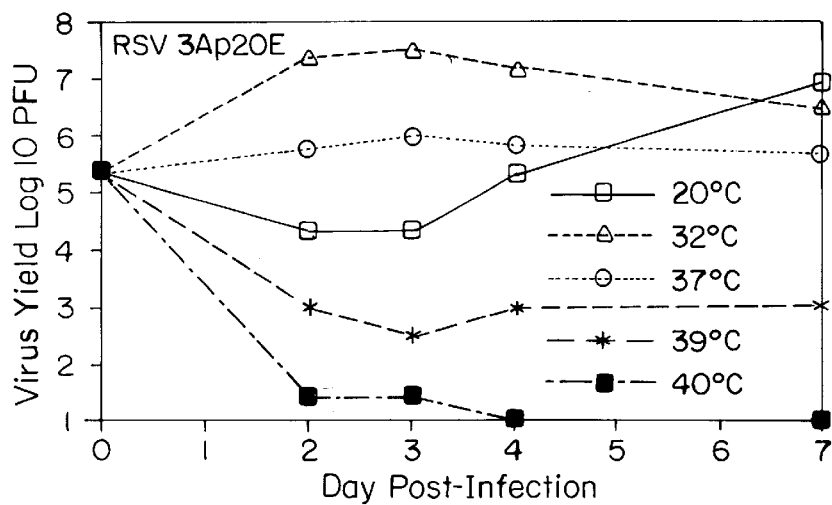
Figure 5E:
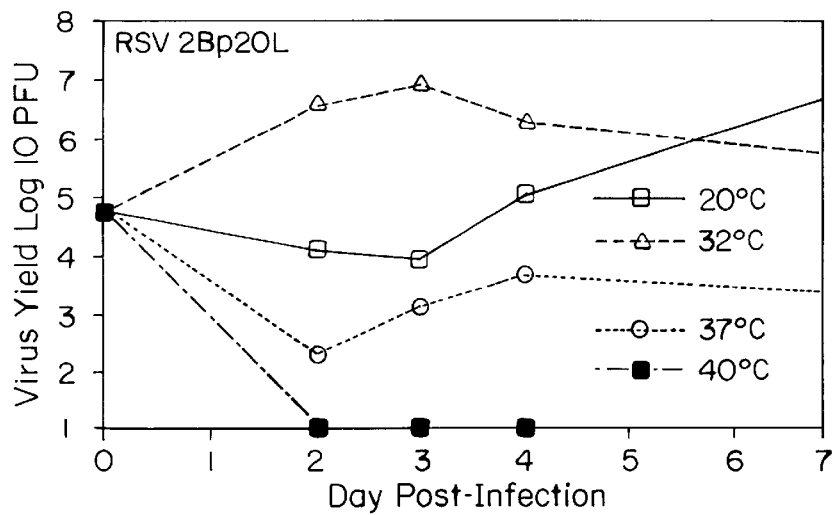
Figure 5F:
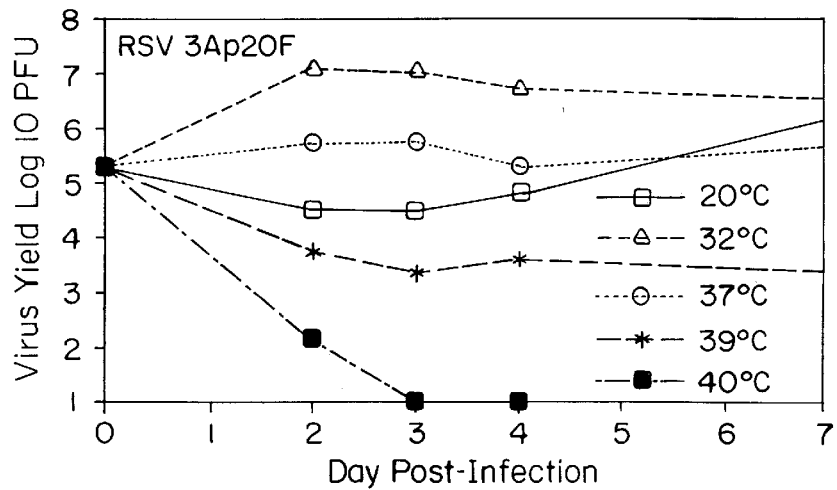

In order to select an appropriate starting temperature for cold adaptation of RSV, growth of the RSV 2B and RSV 3A parental strains in Vero cells at temperatures ranging from 26° C. to 36° C. was compared. Cells were infected at an MOI of 0.4 and virus yield and cytopathic effect (cpe) was monitored for 4 days. The results, shown in FIGS. 2 and 3, demonstrated that for both virus strains, growth at 30° C., 32° C., and 36° C. was similar in kinetics and yield. At 26° C., virus growth lagged behind growth at the higher temperatures by about 24 hours. The limiting factor in achieving optimum titers appeared to be the viral cpe, which occurred earlier at higher temperatures. For both RSV 2B and RSV 3A, optimum titers were achieved by maintaining cultures at 30° C. At this temperature, a lower level of cpe allowed growth and spread of virus to continue over a longer time period. The results suggested that these strains of RSV were already well adapted to growth at 30° C. to 36° C. A maximum temperature of 26° C. was selected as a starting temperature for cold adaptation, as virus growth at this temperature was suboptimal and therefore some selective pressure for cold adaptation would be exerted.

Cold adaptation was initiated on virus stocks RSV 2B (passage MK7 V14) and RSV 3A (passage MK8 V14). To maximize the chance of recovering appropriately attenuated mutants from these cold adapted populations, two flasks of virus were independently passed using each of three different cold adaptation strategies. This provided a total of six cold adapted populations for RSV 2B and six for RSV 3A. Virus was passaged in 25 cm$^2$ flasks containing confluent Vero cell monolayers. At each passage, virus was harvested by replacing the maintenance medium (10 mls of MEM/2%FBS/20 mM Hepes) in the infected flask with a reduced volume of freezing medium (3 mls of MEM/10%FBS/20 mM Hepes) and performing a quick freeze at −70° C. followed by a thaw at 32° C. To infect the next passage, 1 ml of the freeze-thaw lysate was transferred to a fresh flask of confluent Vero cells, virus was allowed to adsorb at room temperature (20° C.–22° C.), and then flasks were overlaid with maintenance medium (MEM/2%FBS/20 mM Hepes) and incubated at the appropriate temperature in water baths (i.e., 26° C., 22° C., 20° C.).

Titrations were performed at 32° C. on each freeze-thaw lysate and the remainder of the material was stored at −70° C. for future isolation of virus variants. Three passaging strategies were used. Flasks E and F were "slowly" adapted, beginning at 26° C. with 4 passages every 2 days, followed by passage once every week until titers appeared to be relatively stable or were increasing. Virus was then passaged weekly at 22° C. until consistently high titers were achieved, and finally maintained by passage every 1–2 weeks at 20° C. Flasks G, H, and I were adapted by a more moderate strategy. Virus was passaged 2 times at 26° C. at 3 day intervals, then passaged weekly at 22° C. 5 times, and finally maintained by passage every 1–2 weeks at 20° C. Flasks J and L were "rapidly" adapted, starting with 5 weekly passages at 22° C., followed by passage at 1–2 week intervals at 20° C. Actual passage conditions and titration results are shown in Tables 1 and 2, and are summarized in Table 3. Titration results obtained at each passage are graphically displayed in FIG. 4. The titration results demonstrated an influence of strain on rate of adaptation. For RSV 2B, all three cold adaptation strategies eventually yielded high virus titers when flasks were maintained at 20° C. In contrast, RSV 3A was adapted to growth at 20° C. using a "slow"

strategy (E,F), but efforts to force a more rapid adaptation resulted in a precipitous decline in virus growth. Passage of these cultures (3A:H,I,J,L) was discontinued.

To screen the cold adapted virus populations for accumulation of TS variants, virus taken from each flask following 5 and 17 weeks of cold adaptation was tested for efficiency of plaquing (EOP) at 39° C. vs. 32° C. As seen in Table 4, in most cases plaguing efficiency of the cold passage virus was relatively high at 39° C. ($\geq 0.2$) and was similar to values obtained with the parental virus control ($\geq 0.6$). The results showed that the cold adapted virus populations, with the possible exception of flask RSV 3A-F, had not become predominantly TS over a period of up to 17 low temperature passages.

Following further cold passaging, attempts were made to isolate temperature sensitive mutants by plaque purifying virus from each cold adapted flask. Plaque purified mutants were initially identified by relatively poor growth (lower titers or smaller plaque size) at 39° C. vs 32° C. In these assays, shown in Table 5, the percentage of plaque purified virus that could be clearly identified as temperature sensitive ranged from 0% to 40% of plaques picked. Several individual flasks (2B-H, 2B-L, 3A-E, 3A-F) appeared to contain a relatively higher percent of TS phenotypes, and in some cases the percentage of TS mutants increased over time. However, TS mutants did not appear to become a predominant variant over a period of up to 42 weeks of cold passaging.

To summarize, cold passaging of RSV 2B and RSV 3A resulted in cold adaptation of virus based on the ability of virus to grow stably at 20° C. with consistently high yields. Analysis of EOP assays and the rate of isolation of TS mutants indicated that although TS mutants did arise in the cold adapted virus populations, they did not become a predominant species.

Screening for Vaccine Candidates

TS mutants were further screened and selected for vaccine candidates based on degree of temperature sensitivity in vitro, attenuation in animal models (including mice, cotton rats, and chimps), and retention of neutralizing epitopes.

Over a period of 39 weeks of cold adaptation, a total of 13 RSV 2B and 6 RSV 3A TS mutants were plaque purified a second time and further characterized. Comparison of EOP's at 37/32° C., 39/32° C., and/or 40/32° C. confirmed that these mutants had reduced plaquing efficiency at the higher temperatures and represented a range of temperature sensitivity (see Table 6).

Prior to completing the isolation of all 19 mutants described above, a group of 4 mutants, RSV 2Bp24G, RSV 2Bp20L, RSV 3Ap20E, and RSV 3Ap20F, were selected from the first set of plaque purified viruses for preliminary characterization. To look at actual virus growth curves, Vero cells were infected with these 4 mutants at an MOI of 2, and incubated at 20° C., 32° C., 37° C., and 40° C. for 7 days. The results, shown in FIG. 5, indicated that all 4 mutants were cold adapted and temperature sensitive, as evidenced by earlier and higher rises in titer in cultures incubated at 20° C., and reduced or absent growth of virus in cultures incubated at 37° C., 39° C., and 40° C. Based on the degree of temperature sensitivity seen in EOP and growth studies, one subgroup A and one subgroup B mutant, RSV 2Bp20L and RSV 3Ap20E, were selected to perform additional preliminary experiments on phenotypic stability and growth in mice.

The infectivity and immunogenicity of RSV 2Bp20L and RSV 3Ap20E were evaluated in Balb/c mice. Virus growth was measured in nasal wash and lung samples harvested 4 and 5 days post-infection and serum neutralizing antibody titers were determined 32 days post-infection. Results are shown in Table 7. Growth and immunogenicity of the parental virus was very low, but detectable. In contrast, no virus was recovered and no neutralizing antibody was detected following inoculation of the TS strains, indicating that these strains were highly attenuated in mice.

Of the 19 TS mutants which were eventually isolated, four RSV 2B and 3 RSV 3A mutants were selected for further in vitro and in vivo characterization. These mutants included the original 4 mutants described above, as well as 3 mutants isolated at later time points. Selection criteria included demonstration of definite TS phenotype at both 37° C. and 39° C. and representation of both subgroups and varying passage strategies and passage numbers. These 7 TS mutants were plaque purified a third time and amplified to make small working stocks. Their passage histories are summarized in Table 8. The initial analysis of these mutant strains included comparison of plaquing efficiencies and plaque morphologies at 32° C., 37° C., and 39° C. in Vero cells (Table 9), and growth at 32° C., 37° C., 39° C., and 40° C. in Vero cells (Table 10). At 37° C. and 39° C., EOP was reduced and small and intermediate plaque sizes predominated, indicating that mutants were TS. Some breakthrough of "wt" plaque size revertants was seen with all variants except RSV 2Bp34L and RSV 3Ap20F. In growth studies, Vero cells were infected with the virus strains at an MOI of 0.2 and virus yield was determined 4 days postinfection. Comparison of virus yields in Vero cells at the various temperatures demonstrated that virus yield, expressed as PFU per cell, decreased significantly at the higher temperatures (37° C., 39° C., 40° C.). In some cases, virus yield was also somewhat reduced at 32° C. relative to the parental strain, indicating attenuation in growth at 32° C. This is consistent with the smaller plaque sizes observed in the 32° C. EOP assays (Table 9). For all strains, at least one plaque was detected in cells incubated at 39° C. or 40° C., suggesting that some revertants were present. Both EOP and virus yield studies demonstrate that these 7 isolates possess varying levels of temperature sensitivity and may represent a range of levels of attenuation.

Retention of neutralizing epitopes was examined by comparing reactivities of the 7 mutants and parental strains with 2 neutralizing monoclonal antibodies representing antigenic sites A and C on the F protein described by Beeler and Coelingh (1989) (Table 11). Both antibodies were able to neutralize all the virus strains at similarly high dilutions, indicating that the neutralizing epitopes were intact.

Growth and immunogenicity of the 7 TS mutant strains was evaluated in cotton rats. Groups of rats were inoculated intranasally with each mutant and lungs and nasal turbinates were harvested 4 days post-infection for virus titrations. Sera were collected from an identical set of rats 20 days postinfection to test for neutralizing and EIA antibody responses. A summary of virus titration and immunogenicity results are shown in Table 12. RSV 2B grew well in the nose and lungs, whereas growth of all 4 RSV 2B TS mutants was very poor. Two of the mutants, RSV 2Bp33F and RSV 2Bp24G, displayed a less attenuated phenotype than did RSV 2Bp20L and RSV 2Bp34L, as indicated by a slightly higher level of replication, as well as a 100% infection rate. The RSV 3A parental and TS mutant strains grew well in the nasal turbinates, but poorly in the lungs. Titers of the RSV 3A TS mutants were lower than that of the parental strain, indicating that the TS mutants were somewhat more attenuated than the parent virus. Neutralizing and EIA-F antibody titers on sera from rats infected with the RSV 2B and RSV 3A parental and TS mutant strains were also measured. The level of neutralizing and EIA-F antibody titer was low for the RSV 2B TS mutants, consistent with the low level of viral replication seen. Interestingly, titers from animals infected with RSV 2Bp33F were higher than would be expected in view of the low titration values, and may indicate an intermediate level of attenuation for this virus. Neutralizing and EIA-F antibody titrations on all 3 RSV 3A TS mutants demonstrated that these mutants were quite immunogenic, consistent with their high level of replication in nasal tissue.

Figure 6A:
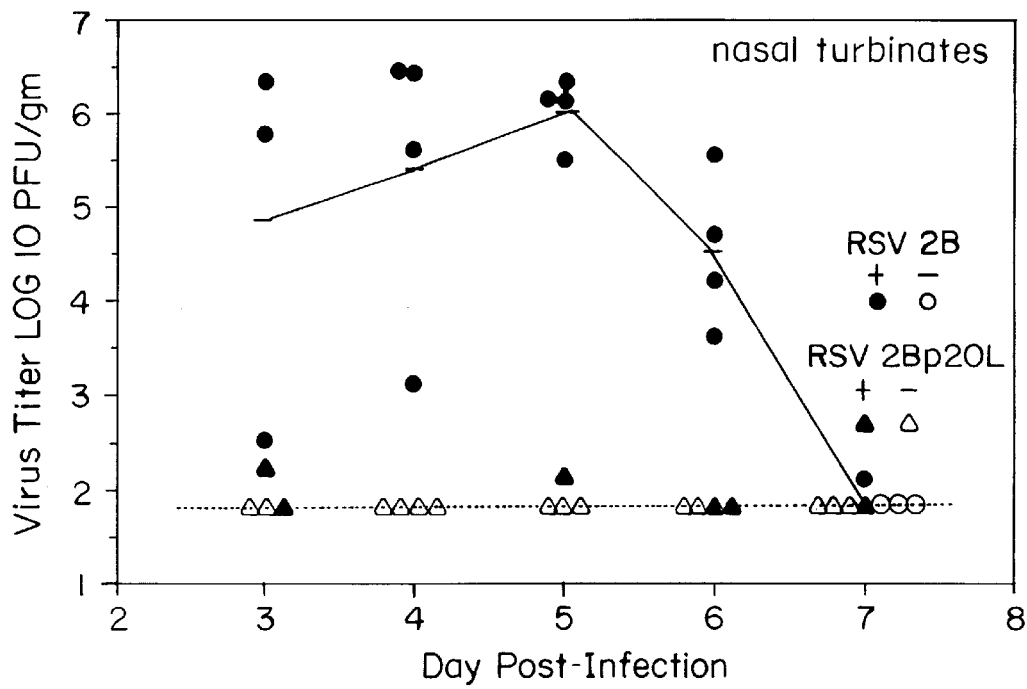
FIGS. 6A and 6B compare graphically the growth of RSV 2B and RSV 2Bp20L in cotton rats from 3 to 7 days postinfection.
Figure 6B:
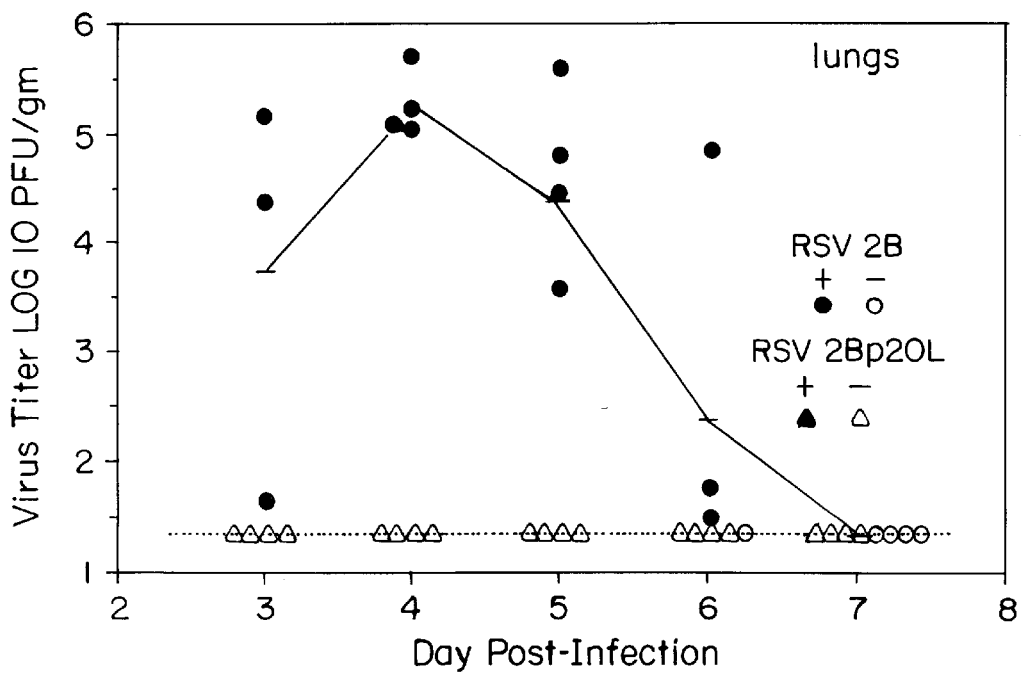

Growth of RSV 2Bp20L was further evaluated in cotton rats from 3 to 7 days post-infection to determine if failure to recover virus was due to a shift in timing of peak titers. RSV 2B was used as a positive control (see FIG. 6). The growth kinetics of RSV 2B were typical of other strains of RSV; peak titers occurred on days 4 and 5 in nasal turbinates and on day 4 in lungs. These results substantiate the use of day 4 as the optimal harvest day for the parental strain. RSV 2Bp20L was not detected in lungs and rare plaques were seen in nasal turbinate titrations on days 3, 5, 6, and 7, demonstrating that attenuation of this virus was not simply due to an early or late growth peak.

Figure 7A:
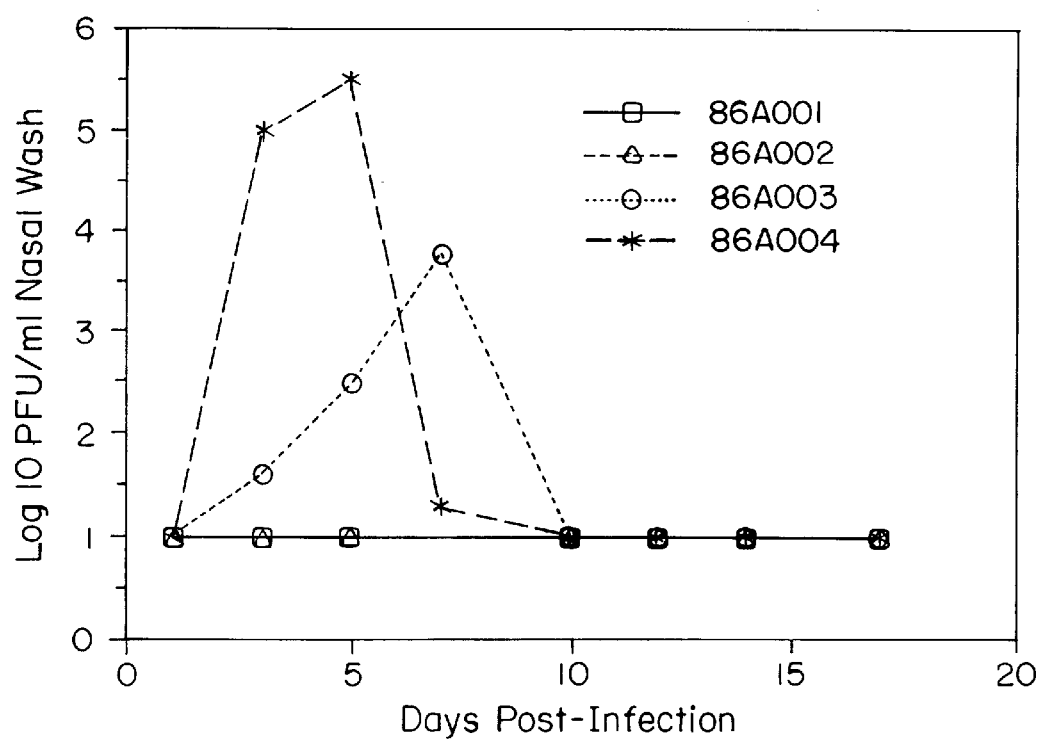

Relative growth and immunogenicity of RSV 2B and RSV 2Bp20L were also compared in 4 year old seropositive chimps. Two chimps were infected intranasally with $10^{4.0}$ and $10^{5.0}$ PFU of RSV 2B, and 2 chimps were similarly infected with RSV 2Bp20L. The results are shown in FIG. 7 and Table 13. Both chimps infected with RSV 2B developed a mild upper respiratory infection, consisting of nasal discharge and cough. Both chimps shed virus from 3 through 7 days postinfection. The amount of virus shed was higher and shedding occurred earlier in the chimp infected with the higher dose of RSV 2B. Neither chimp inoculated with RSV 2Bp20L showed clinical signs of disease or shed virus. Chemistry and hematology workups on all four chimps revealed no significant findings. Serum neutralizing and EIA-F, Ga, and Gb antibody titers were substantially increased 14 and 21 days post-infection with RSV 2B. No rises in antibody titers were seen in chimps inoculated with RSV 2Bp20L. The results indicated that, in seropositive chimps, the parental RSV 2B strain was infectious and immunogenic, whereas the RSV 2Bp20L mutant was highly attenuated.

Identification of Immunogenic Polypeptides

According to the present invention, the regions of RSV which are epitopes responsible for eliciting both antibody and cell mediated immunity can be determined. These epitopes may include, but are not limited to, B-cell and T-cell epitopes. Examples of immunogenic epitopes are those which elicit neutralizing and anti-fusion antibodies, those which induce cytotoxic T-cell (CTL) activity, and those which induce a lymphoproliferative (LP) response. These regions can be defined by three methods. The first method employs defined proteolytic cleavage of the native polypeptide. The second method relates to cloning and expressing fragments of the polypeptide gene, for example, in E. coli. The third relates to synthesis of synthetic polypeptides. In all three methods reactivity with an antibody or reactivity in a CTL or LP assay can be used to identify desired polypeptides, e.g. reactivity with a monoclonal antibody which is capable of neutralizing and preventing fusion of RSV, or ability to stimulate a CTL or LP response in T-cells isolated from animals which have been immunized with RSV or an RSV polypeptide.

Purification of Polypeptide

RSV polypeptide may be purified or isolated by any appropriate method known to those of skill in the art. For exemplary purposes only, an immunoaffinity procedure is provided below.

Immunoaffinity Purification

To isolate immunogenic polypeptides encoded by RSV, affinity chromatography using a monoclonal antibody directed against the polypeptide is used. The monoclonal antibody is purified by ammonium sulphate precipitation from ascetic fluid and adjusted to a concentration of about 10 mg/ml in bicarbonate buffer (0.1M $NaHCO_3$, pH 9.0, 0.5M NaCl). The antibody is coupled to prehydrolyzed cyanogen bromide-activated Sepharose 4B beads (Pharmacia) according to the manufacturer's instructions. A column constructed with 7 ml of beads is stored in PBS, 0.02% azide at 4° C.

RSV-infected cell lysates are applied to the column at 10 ml/hour at 4° C. After sample application, the column is washed with 500 ml of PBS containing 0.1% Triton X-100. Protein bound to the column is eluted with 0.1M glycine pH 2.5, 0.1% Triton X-100 at 6 ml/hour. Elution samples may be buffered to pH 7.0 with tris and analyzed by SDS-PAGE. Polypeptide samples may be pooled and dialyzed against PBS and stored at −70° C.

Proteolytic Cleavage

A monoclonal antibody can be tested for its ability to bind to the immunogenic polypeptide by radioimmunoprecipitation or ELISA analysis. T-cells can be tested for reactivity to the immunogenic polypeptide by CTL or LP assay.

To map the epitope, synthetic polypeptides will be prepared which correspond to various regions along the polypeptide. These synthetic polypeptides are then coupled to a carrier protein, such as keyhole lympet hemocyanin (KLH), and then used separately to immunize rabbits. Antisera produced in the rabbits will react with the uncoupled synthetic polypeptide corresponding to the immunogen which induced the anti-serum.

The purified polypeptide is then subjected to proteolytic cleavage under a variety of conditions. For example, the enzymes can be (1) trypsin which specifically cleaves after lysine and arginine residues, (2) endoproteinase Arg-C which cleaves specifically after arginine residues, and (3) endoproteinase Lys-C which cleaves specifically after lysine residues. Cleavage after a residue means the breaking of a peptide bond at the carboxyl end of the residue. It should be understood that other combinations of proteases can be used. Therefore, the presently exemplified combination should not be construed as a limitation on the present invention. Cleavages can also be performed in the presence and absence of the monoclonal antibody.

The cleaved protein fragments are separated by SDS-PAGE and the cleavage products analyzed by Western blot analysis for the ability to bind to the monoclonal antibody as well as the anti-synthetic polypeptide antibodies. Alternately, the cleaved fragments may be separated by SDS-PAGE and eluted from the gel, or separated by size exclusion columns, and analyzed for the ability to stimulate cell mediated responses, e.g. using LP assays. The positions of the proteolytic fragments within the polypeptide are deduced from the reactivities of these cleavage fragments with each of the anti-synthetic polypeptide antisera. Finally, the molecular weight of a fragment can be determined by its mobility in SDS-PAGE.

The relationship between the positions of the cleavage fragments and the reactivities of these fragments to the monoclonal antibody or in assays for cell mediated response, e.g., LP assays are analyzed, and the immunogenic epitopes of the RSV defined by the antibody or cellular reactivity are determined.

Cloning And Expression Of The Polypeptides

Regions of the nucleic acid encoding the polypeptide are excised from the cloning vector by restriction endonuclease digestion and ligated into a compatible expression vector (see supra). The expressed recombinant proteins are screened for reactivity first with polyclonal rabbit antiserum to native polypeptide to identify recombinant fragments and then with the appropriate monoclonal antibody or in a CTL or LP assay, to identify those fragments comprising the immunogenic epitope.

Antigenic Polypeptides

In order to confirm the identity of the immunogenic epitope identified as described above, synthetic polypeptides can be prepared corresponding in particular to amino acid residues of the RSV polypeptide. The peptides are analyzed for reactivity to an appropriate monoclonal antibody, or in a CTL or LP assay.

Preparation Of Proteins and Polypeptides And Peptides Related To RSV

The proteins and polypeptides of the present invention can be prepared in a wide variety of ways. The polypeptides, because of their relatively short size may be synthesized in solution or on a solid support in accordance with conventional techniques. Various automatic synthesizers are commercially available and can be used in accordance with known protocols. See, for example, Stewart and Young, 1984, Solid Phase Peptide Synthesis, 2d Ed., Pierce Chemical Co. The structural properties of polypeptides, of which three dimensional configuration is one, may only be minutely changed by the introduction of a small number of modifications such as substitutions, insertions and deletions of one or more amino acids. Generally, such substitutions in the amino acid sequence of a polypeptide are in the amount of less than twenty percent, more usually less than ten percent. Generally, conservative substitutions are less likely to make significant structural changes than non-conservation substitutions, which in turn are less likely to make significant structural changes than insertions or deletions. Examples of conservative substitutions are glycine for alanine; valine for isoleucine; aspartic acid for glutamic acid; asparagine for glutamine; serine for threonine; lysine for arginine; phenylalanine for threonine; and the converse of the above. Therefore, it is to be understood that the present invention embraces modified polypeptides so long as the epitope of the RSV polypeptide remains unchanged.

It is also well known that viral epitopes may exhibit strain-to-strain variations. Adjustment by the above-indicated modifications may indeed be used advantageously.

The polypeptides of the present invention may be employed as labeled or unlabeled compounds depending on their use. By label is intended a moiety which provides, directly or indirectly, a detectable signal. Various labels may be employed, such as radio-nucleotides, enzymes, fluorescers, chemiluminescers, enzyme substrates, cofactors or inhibitors, particles (e.g. magnetic particles), ligands (e.g. biotin) and receptors (e.g. avidin) or the like. In addition, the polypeptides may be modified in a variety of ways for binding to a surface, e.g. microtiter plate, glass beads, chromatographic surface, e.g. paper, cellulose and the like. The particular manner in which the polypeptides are joined to another compound or surface is conventional and finds ample illustration in the literature. See, for example, U.S. Pat. Nos. 4,371,515; 4,487,715 and the patents cited therein.

Alternatively, recombinant DNA technology may be employed to prepare the polypeptides biosynthetically.

Recombinant DNA Technology And Gene Expression

Recombinant DNA technology involves insertion of specific DNA sequences into a DNA vehicle (vector) to form a recombinant DNA molecule which is capable of being replicated in a host cell. Generally, but not necessarily, the inserted DNA sequence is foreign to the recipient DNA vehicle, i.e. the inserted DNA sequence and DNA vector are derived from organisms which do not exchange genetic information in nature, or the inserted DNA sequence comprises information which may be wholly or partially artificial. Several general methods have been developed which enable construction of recombinant DNA molecules. For example. U.S. Pat. No. 4,237,224 to Cohen and Boyer describes production of such recombinant plasmids using processes of cleavage of DNA with restriction enzymes and joining the DNA pieces by known methods of ligation.

These recombinant plasmids are then introduced by means of transformation or transfection and replicated in unicellular cultures including prokaryotic organisms and eukaryotic cells grown in tissue culture. Because of the general applicability of the techniques described therein, U.S. Pat. No. 4,237,224 is hereby incorporated by reference into the present specification. Another method for introducing recombinant DNA molecules into unicellular organisms is described by Collinq and Hohn in U.S. Pat. No. 4,304,863 which is also incorporated herein by reference. This method utilizes a packaging, transduction system with bacteriophage vectors (cosmids).

Nucleic acid sequences may also be inserted into viruses, for example, vaccinia virus or the mutant virus of this invention or its cDNA clone. Such recombinant viruses may be generated, for example, by transfection of plasmids or cotransfection of baculovirus into cells infected with virus (Chakrabarti et al., 1985).

Regardless of the method used for construction, the recombinant DNA molecule is preferably compatible with the host cell, i.e., capable of being replicated in the host cell either as part of the host chromosomes or as an extrachromosomal element. The recombinant DNA molecule or recombinant virus preferably has a marker function which allows the selection of the desired recombinant DNA molecule(s) or virus(es). In addition, if all of the proper replication, transcription and translation signals are correctly arranged on the recombinant DNA molecule, the foreign gene will be properly expressed in the transformed or transfected host cells either constitutively or by induction.

Different genetic signals and processing events control gene expression at different levels. For instance, DNA transcription is one level, and messenger RNA (mRNA) translation is another. Transcription of DNA is dependent upon the presence of a promoter which is a DNA sequence that directs the binding of RNA polymerase and thereby promotes RNA synthesis. The DNA sequences of eukaryotic promoters differ from those of prokaryotic promoters. Furthermore, eukaryotic promoters and accompanying genetic signals may not be recognized in or may not function in a prokaryotic system.

Similarly, translation of mRNA in procaryotes depends upon the presence of the proper prokaryotic signals which differ from those of eucaryotes. Efficient translation of mRNA in prokaryotes requires a ribosome binding site called the Shine-Dalgarno (SD) sequence on the mRNA. For a review on maximizing gene expression, see Roberts and Lauer, 1979.

Many other factors complicate the expression of foreign genes in prokaryotes even after the proper signals are inserted and appropriately positioned. One such factor is the presence of an active proteolytic system in *E. coli* and other bacteria. This protein-degrading system appears to destroy foreign proteins selectively. A tremendous utility, therefore, would be afforded by the development of a means to protect eukaryotic proteins expressed in bacteria from proteolytic degradation. One strategy is to construct hybrid genes in which the foreign sequence is ligated in phase (i.e. in the correct reading frame) with a prokaryotic structural gene. Expression of this hybrid gene results in a recombinant protein product (a protein that is a hybrid of prokaryotic and foreign amino acid sequences).

Similar considerations of gene expression in eukaryotic systems have been discussed in Enhancers & Eukaryotic Gene Expression, Gluzman & Shenk (Eds.), Cold Spring Harbor Laboratories, Cold Spring Harbor, N.Y. 1983, and Eukaryotic Viral Vectors, Gluzman (Ed.), Cold Spring Harbor Laboratories, Cold Spring Harbor, N.Y. 1982.

Successful expression of a cloned gene requires efficient transcription of DNA, translation of the mRNA and in some instances post-translational modification of the protein. Expression vectors have been developed to increase protein production from the cloned gene. In expression vectors, the cloned gene is often placed next to a strong promoter which is controllable so that transcription can be turned on when necessary. Cells can be grown to a high density and then the promoter can be induced to increase the number of transcripts. These, if efficiently translated, will result in high yields of protein. This is an especially valuable system if the foreign protein is deleterious to the host cell.

Determination of RSV Genomic Sequence

The nucleic acid sequence of the RSV genome is determined by sequencing cDNA copies of the viral mRNAs and by sequencing the 5' and 3' ends of a purified viral RNA. Intergenic regions are sequenced from "read-through" viral mRNAs or by polymerase chain reaction (PCR) of genomic viral RNA. The determination of the RSV A2 strain genomic sequence has been described by Collins (1991).

To sequence regions encoded by viral mRNA (e.g, regions encoding the L,P,N,G,F,M, M2(22K), SH, 1B, and 1C proteins) viral mRNAs are purified from RSV infected Vero cell cultures using an oligo-dT column. Procedures and kits for purification of mRNA are available commercially, e.g., Invitrogen's Fast Track™ kit. The purified poly (A)+ mRNA is used to make a cDNA library in competent E. coli (e.g., strain DH5a) using techniques well known to those skilled in the art and available in commercial kits e.g., Invitrogen's Librarian™ II cDNA Library Construction System. Ampicillin resistant bacterial colonies are screened by colony filter hybridization (Grunstein and Hogness, 1975) using hybridization probes specific for regions of RSV mRNA. These probes are radiolabeled RSV sequences and consist of synthesized oligonucleotides or portions of genes previously cloned from RSV. Methods of constructing and radiolabeling hybridization probes are well know to those skilled in the art and commercial kits are available, e.g., Boehringer Mannheim's 5' End Labeling kit or Random Primed DNA Labeling kit. Bacterial colonies which are identified as containing viral sequence (in recombinant plasmids) are used to amplify the plasmid DNA which is then sequenced by the dideoxynucleotide method of Sanger (1977) or by using an automated DNA sequencer (e.g. Applied Biosystems automated sequencer and Taq DyeDeoxy™ Terminator Cycle Sequencing kit). Some intergenic regions of the viral genomic RNA are identified in bacterial colonies containing clones which have "read-through" viral sequences which hybridize DNA probes from adjacent viral genes and which contain both or parts of these adjacent genes and the noncoding regions between these genes. The 3' end may be seen as a "read-through" from 1C mRNA. These regions are sequenced as described above.

Purified genomic viral RNA may be used to determine the sequence of regions of virus not encoded in the viral mRNA, e.g., the 5' and 3' noncoding regions and the intergenic sequences not obtained as described above. Genomic viral RNA is purified by the method of Huang and Wertz (1982) as follows. Virus-infected Vero cells are lysed by quick freeze-thaw and lysates are clarified by low speed centrifugation. Virus is pelleted from lysates by ultracentrifugation, then resuspended by sonication and centrifuged through a 10–50% linear sucrose gradient. The visible virus band is collected, sonicated, and rebanded in a 20–60% sucrose gradient. The visible virus band is collected, sonicated, and the genomic viral RNA isolated by phenol extraction and recovered by ethanol precipitation. The sequence of the 5' end may be determined by dideoxynucleotide sequencing of the 5' end of the genomic viral RNA. The sequence of the 3' end may be determined by direct chemical sequence analysis of 3' end-labeled viral RNA. Alternately, the 5' end may be determined by primer extension with a 5' end-labeled oligonucleotide of antigenome polarity using reverse transcriptase and the negative strand genomic viral RNA as template. The product from this reaction is gel purified and sequenced directly by the Maxam and Gilbert (1980) technique of base-specific cleavage. To sequence any internal sequence not obtained by other methods (e.g., intergenic sequences), PCR may be used. To use this method, the viral RNA is reverse transcribed to provide an initial DNA template, oligonucleotide primers are synthesized which hybridize strands of opposite polarity on either side of the region of interest, and the region is amplified by PCR. The PCR product may be sequenced directly or may be ligated into a plasmid vector and then sequenced.

Several recombinant DNA expression systems are described below for the purpose of illustration only, and these examples should not be construed to limit the scope of the present invention.

E. Coli As An Expression Vector

Many E. coli plasmids are known and have been used to express foreign genes. For economic reasons, it would be highly preferable to be able to obtain a high level of expression. One way to obtain large amounts of a given gene product is to clone a gene on a plasmid which has a very high copy number within the bacterial cell. By increasing the number of copies of a particular gene, mRNA levels would normally also increase, which in turn would lead to increased production of the desired protein. If a region of gene encodes a protein sequence that is detrimental to the E. coli, such region may be deleted from the nucleic acid and the remaining nucleic acid will encode a shorter polypeptide.

Vaccinia Virus As An Expression Vector

Vaccinia virus may be used as a cloning and expression vector. The virus contains a linear double-stranded DNA genome of approximately 187 kb pairs and replicates within the cytoplasm of infected cells. These viruses contain a complete transcriptional enzyme system (including capping, methylating and polyadenylating enzymes) within the virus core. This system is necessary for virus infectivity because vaccinia virus transcriptional regulatory sequences (promoters) allow for initiation of transcription by vaccinia RNA polymerase, but not by cellular RNA polymerase.

Expression of foreign DNA in recombinant viruses requires the fusion of vaccinia promoters to protein coding sequences of the foreign gene. Plasmid vectors, also called insertion vectors have been constructed to insert the chimeric gene into vaccinia virus. One type of insertion vector comprises: (1) a vaccinia virus promoter including the transcriptional initiation site; (2) several unique restriction endonuclease cloning sites downstream from the transcriptional start site for insertion of foreign DNA fragments; (3) nonessential vaccinia virus DNA (such as the thymidine kinase gene) flanking the promoter and cloning sites which direct insertion of the chimeric gene into the homologous nonessential region of the virus genome; and (4) a bacterial origin of replication and antibiotic resistance marker for replication and selection in E. coli. Examples of such vectors are described by MacKett (1984).

Recombinant viruses are produced by transfection of recombinant bacterial insertion vectors containing the foreign gene into cells infected with vaccinia virus. Homologous recombination takes place within the infected cells and results in the insertion of the foreign gene into the viral genome. See for example, U.S. Pat. No. 4,603,112, the contents of which are incorporated by reference. Immunological techniques, DNA plaque hybridization, or genetic selection can be used to identify and isolate the desired recombinant virus. These vaccinia recombinants retain the functions essential for infectivity and can be constructed to accommodate up to approximately 35 kb of foreign DNA.

Expression of a foreign gene can be detected by enzymatic or immunological assays (e.g., immunoprecipitation, enzyme-linked immunosorbent assay (ELISA), radioimmunoassay, or immunoblotting). Additionally, naturally occurring membrane glycoproteins produced from recombinant vaccinia infected cells are glycosylated and may be transported to the cell surface. High expression levels can be obtained by using strong promoters or cloning multiple copies of a single gene.

Poliovirus as an Expression Vector

Poliovirus is also used as expression vector for mutant RSV genetic sequences (e.g. immunogenic polypeptides). The virus contains a 7.5 kb linear single-stranded RNA genome of positive polarity and replicates within the cytoplasm of infected cells.

It has been found that full-length poliovirus cDNA is infectious. Such poliovirus cDNA clones are constructed and used to produce virus according to U.S. Pat. No. 4,719,177, the contents of which are incorporated by reference. Foreign DNA can be incorporated within the infectious poliovirus cDNA to produce altered virus particles. For example, poliovirus has been genetically altered such that antigenic site 1 presents epitopes of other pathogens (Rose and Evans, 1991).

Such chimeric viruses have been constructed by two methods. As described by Burke et al. (1988), a convenient restriction fragment of an infectious cDNA clone of poliovirus which includes the region of VP1 encoding antigenic site 1 (NAg-1) is subcloned into phage M13mp18. A mutated fragment is produced using oligonucleotide-directed mutagenesis so that the coding region for NAg-1 is replaced by the foreign epitope sequence. The full-length cDNA is reconstructed with the mutated fragment. According to another method by Burke et al. (1989), the full-length infectious cDNA is modified to create a cassette vector in which the region of VP1 encoding NAg-1 is flanked by unique restriction endonuclease sites. The NAg-1 site can then be readily replaced by complementary oligonucleotides encoding the foreign sequence.

A second approach involves using poliovirus as a delivery vector for expression of foreign genes in vivo. Full length or partial gene sequences can be introduced into the polio genome in frame with the polio open reading frame. The insertion site may be at the 5' end of the open reading frame or at other cleavage junctions within the genome, eg. between P1 and P2. Incorporation of polio protease cleavage recognition sites flanking the foreign gene allows processing of the foreign proteins following expression from the recombinant poliovirus. In this approach the foreign gene rather than protein is carried within the recombinant virus and is only expressed during viral replication.

The altered virus particles are produced by transfection of cells with the modified full-length poliovirus cDNA or RNA transcribed from the cDNA. Sequence analysis of genomic RNA can be used to confirm that the recovered virus contains the foreign sequence.

Expression of the foreign sequence can be detected by immunological assays (e.g. immunoprecipitation, neutralization, ELISA).

Baculovirus As An Expression Vector

A baculovirus, such as Autographica californica nuclear polyhedrosis virus (AcNPV) can also be used as a cloning or expression vector. The infectious form of AcNPV is normally found in a viral occlusion. This structure is largely composed of polyhedrin polypeptide in which virus particles are embedded. Polyhederin gene expression occurs very late in the infection cycle, after mature virus particles are formed. Therefore, polyhedrin gene expression is a dispensable function, i.e., non-occluded virus particles produced in the absence of polyhedrin gene expression are fully active and are capable of infecting cells in culture. According to European Patent Application Serial No. 84105841,5 by Smith et al., a recombinant baculovirus expression vector can be prepared in two steps. First, baculovirus DNA is cleaved to produce a fragment comprising a polyhedrin gene or a portion thereof, which fragment is inserted into a cloning vehicle. The gene to be expressed is also inserted into the cloning vehicle; and it is so inserted that it is under control of the polyhedrin gene promoter. This recombinant molecule is called a recombinant transfer vector. Normally, the recombinant transfer vector is amplified in appropriate host cells. Second, the recombinant transfer vector formed in this way is mixed with baculovirus helper DNA and used to transfect insect cells in culture to effect recombination and incorporation of the cloned gene at the polyhedrin gene locus of the baculovirus genome. The resultant recombinant baculovirus is used to infect susceptible insects or cultured insect cells.

In another example, restriction enzyme sites are constructed at both ends of the gene, or part thereof, to be expressed. Direct ligation is accomplished into an appropriately engineered baculovirus which has compatible restriction sites which are cut allowing specific insertion behind the polyhedrin promoter or other appropriate baculoviral promoter.

Insertion Of The RSV Polypeptide Coding Sequences Into Expression Vectors

The nucleotide sequence coding for the RSV polypeptide thereof or for the RSV polypeptide can be inserted in an appropriate expression vector, i.e. a vector which contains the necessary elements for the transcription and translation of the inserted protein-coding sequence. According to a preferred embodiment of the invention, nucleotide sequences coding for an immunogenic polypeptide is inserted into an appropriate expression vector. The coding sequence may be extended at either the 5' and 3' terminus or both termini to extend biosynthetically the polypeptide while retaining the epitope. The extension may provide an arm for linking, e.g., to a label, to a carrier or surface. The extension may provide for immunogenicity which may otherwise be lacking in some of the shorter antigenic polypeptides of the invention.

A variety of host-vector systems may be utilized to express the protein-coding sequence. These include but are not limited to mammalian cell cultures such as Chinese hamster ovary cell host cultures, etc.; mammalian cell systems infected with virus (e.g. vaccinia virus, adenovirus, etc.); insect cell systems infected with virus (e.g. baculovirus); microorganisms such as yeast containing yeast vectors or bacteria transformed with bacteriophage DNA, plasmid DNA or cosmid DNA. In one embodiment the expression vector can be an attenuated enteroinvasive bacteria including but not limited to Salmonella spp., enteroinvasive E. coli (EIEC), and Shigella spp. Such bacterium can invade gut epithelial tissue, disseminate throughout the reticuloendothelial system and gain access to mesenteric lymphoid tissue where they multiply and induce humoral and cell-mediated immunity. The expression elements of these vectors vary in their strength and specificities. Depending on the host-vector system utilized, any one of a number of suitable transcription and translation elements may be used. For instance, when cloning in mammalian cell systems, promoters isolated from the genome of mammalian cells, (e.g., mouse metallothionine promoter) or from viruses that grow in these cells, (e.g. vaccinia virus 7.5K promoter) may be used. Promoters produced by recombinant DNA or synthetic techniques may also be used to provide for transcription of the inserted sequences.

Specific initiation signals may have to be provided for efficient translation of inserted protein coding sequences. These signals include the ATG initiation codon and adjacent sequences. In cases where the RSV polypeptide, the RSV chimeric or RSV gene including its own initiation codon and adjacent sequences are inserted into the appropriate expression vectors, no additional translational control signals may be needed. However, in cases where only a portion of the RSV polypeptide sequence is inserted, exogenous translational control signals, including the ATG initiation codon must be provided. The initiation codon must have to be furthermore be in phase with the reading frame of the protein coding sequences to ensure translation of the entire insert. These exogenous translational control signals and initiation codons can be a variety of origins, both natural and synthetic.

Any of the methods previously described for the insertion of DNA fragments into a vector may be used to construct expression vectors containing a chimeric gene consisting of appropriate transcriptional/translational control signals and the protein coding sequences. These methods may include in vitro recombinant DNA and synthetic techniques and in vivo recombinations (genetic recombination).

In cases where an adenovirus is used as an expression vector, the mutant RSV polypeptide gene is ligated to an adenovirus transcriptional/translational control complex, e.g., the late promoter and tripartite leader sequences. This chimeric gene is then inserted in the adenovirus genome by in vitro or in vivo recombination. Insertion in a non-essential region of the viral genome (e.g., region E1 or E3) will result in a recombinant virus that is viable and capable of expressing the RSV polypeptide in infected hosts.

In addition, a host cell strain may be chosen which modulates the expression of the inserted sequences, or modifies and processes the chimeric gene product in the specific fashion desired. Expression from certain promoters can be elevated in the presence of certain inducers, (e.g., zinc and cadmium ions for metallothionine promoters). Therefore, expression of the genetically engineered RSV polypeptide may be controlled. This is important if the protein product of the cloned foreign gene is lethal to host cells. Furthermore, modifications (e.g., glycosylation) and processing (e.g., cleavage) of protein products are important for the function of the protein. Different host cells have characteristic and specific mechanisms for the post-translational processing and modification of proteins. Appropriate cell lines or host systems can be chosen to ensure the correct modification and processing of the foreign protein expressed.

Identification Of Recombinant Expression Vectors Capable Of Replicating And Expressing The Inserted Gene Expression vectors containing foreign gene inserts can be identified by three general approaches: (a) DNA—DNA hybridization, (b) presence or absence of "marker" gene functions, and (c) expression of inserted sequences. In the first approach, the presence of a foreign gene inserted in an expression vector can be detected by DNA—DNA hybridization using probes comprising sequences that are homologous to the foreign inserted gene. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus etc.) caused by the insertion of foreign genes in the vector. For example, if the RSV gene is inserted within the marker gene sequence of the vector, recombinants containing the RSV polypeptide inserted can be identified by the absence of the marker gene function. In the third approach, recombinant expression vectors can be identified by assaying the foreign gene product expressed by the recombinant. Such assays can be based on the physical, immunological, or functional properties of the gene product.

Once a particular recombinant DNA molecule is identified and isolated, several methods may be used to propagate it, depending on whether such a recombinant constitutes a self-replicating unit (a replicon). A self replicating unit e.g., plasmids, viruses, cells, etc., can multiply itself in the appropriate cellular environment and growth conditions. Recombinants lacking a self-relicating unit will have to be integrated into a molecule having such a unit in order to be propagated. For example, certain plasmid expression vectors upon introduction into a host cell need to be integrated into the cellular chromosome to ensure propagation and stable expression of the recombinant gene. Once a suitable host system and growth conditions are established, recombinant expression vectors can be propagated and prepared in quantity.

Identification And Purification Of The Expressed Gene Product

Once a recombinant which expresses the RSV polypeptide thereof is identified, the gene product should be analyzed. This can be achieved by assays based on the physical, immunological or functional properties of the product. Immunological analysis is especially important where the ultimate goal is to use the gene products or recombinant viruses that express such products in vaccine formulations and/or as antigens in diagnostic immunoassays.

A variety of antisera are available for analyzing imunoreactivity of the product, including but not limited to, polyclonal antisera raised against purified protein as described infra.

The protein should be immunoreactive whether it results from the expression of the entire gene sequence, a portion of the gene sequence or from two or more gene sequences which are ligated to direct the production of chimeric proteins. This reactivity may be demonstrated by standard immunological techniques, such as radioimmunoprecipitation, radioimmune competition, or immunoblots.

Once the RSV polypeptide is identified, it may be isolated and purified by standard methods including chromatography (e.g. ion exchange, affinity, and sizing column chromatography), centrifugation, differential solubility, or by any other standard technique for the purification of proteins.

Determination Of The Immunopotency Of The Pharmaceutical Composition

Immunopotency of the RSV related product or pharmaceutical composition can be determined by monitoring the immune response of test animals following immunization with any of the above-identified RSV live viral mutants, polypeptides or chimeric polypeptides. In cases where the RSV polypeptide is expressed by an infectious recombinant virus, the recombinant virus itself can be used to immunize test animals. Test animals may include but are not limited to mice, rats (e.g. cotton rats), rabbits, primates e.g. African green monkeys, chimps, and human subjects. Methods of introduction of the immunogen may include oral, intradermal, intramuscular, intraperitoneal, intravenous, subcutaneous, intranasal or any other standard routes of immunizations. The immune response of the test subjects can be analyzed by four approaches: (a) the reactivity of the resultant immune serum to authentic RSV antigens, as assayed by known techniques, e.g., enzyme linked immunosorbant assay (ELISA), immunoblots, radioimmunoprecipitations, etc., (b) the ability of the immune serum to neutralize RS virus infectivity in vitro, (c) the ability of the immune serum to inhibit virus fusion in vitro and (d) protection from RSV infection or significant disease.

The following data demonstrates the utility of RSV TS mutants in a vaccine composition. Experiments demonstrating efficacy of vaccines in a cotton rat model, and attenuation, immunogenicity, and efficacy of vaccines in an African green monkey model are described.

i) Cotton Rat Model:

Additional experiments were done in cotton rats to evaluate the efficacy of the RSV 2B and 3A TS mutants in preventing infection when challenged with a reference strain of the homologous subgroup (RSV 18537/subgroup B and RSV A2/subgroup A). Cotton rats (8 per group) were inoculated intranasally with each RSV TS mutant. Nasal turbinates and lungs were harvested 4 days post-infection, from 4 rats per group, for virus titrations. Six weeks post-infection, the remaining rats were bled for neutralizing and EIA-F titers, then challenged with the appropriate reference RSV strain. Four days post-challenge, nasal turbinates and lungs were removed for virus titration. Results are shown in Tables 14 and 15.

As discussed previously and shown in Table 12, growth of all four RSV 2B TS mutants was very poor compared to the parental RSV 2B strain. Neutralizing and EIA antibody titers elicited by RSV 2Bp33F and RSV 2Bp24G were relatively high despite poor virus recovery, possibly indicating an intermediate level of attenuation for both mutants. Level of protection against virus challenge reflected the level of neutralizing antibody response and was high for RSV 2Bp33F and 2Bp24G, moderate for RSV 2Bp20L, and ineffective for RSV 2Bp34L. All RSV 3A strains grew in the nasal turbinates but demonstrated a high level of attenuation in growth in the lungs. Titers of neutralizing and EIA antibodies were high and all rats were completely protected against virus challenge.

The results demonstrate that growth of the attenuated strains elicited protective immunity against virus challenge, suggesting that these strains may be useful as vaccine.

Failure of vaccination with the RSV 2Bp34L strain to protect was most likely due to failure of virus to grow due to its high level of attenuation. Since cotton rats are a less susceptible host than humans, failure of this strain to protect does not imply that 2Bp34L would be an ineffective vaccine in humans.

ii) African Green Monkey Model:

Growth, immunogenicity, and efficacy of TS mutant strains RSV 2Bp33F, 2Bp24G, 2Bp20L, 3Ap20E, 3Ap20F, and 3Ap28F were evaluated in African green monkeys (AGMs). AGMs are more susceptible to infection with human RSV than are the cotton rats, and characteristics of infection may be more relevant to that seen in humans because of the closer phylogenetic relationship. Two AGMs each were inoculated with $10^6$ PFU of each mutant virus by combined intranasal and intratracheal route. Virus growth was evaluated by nasal wash and bronchial lavage. Neutralizing and EIA antibody responses were tested at approximately 0, 1, 2, 3, 4, 6, and 8 weeks post-infection. Eight weeks post-infection, animals were challenged with $10^6$ PFU of the parental strain by intranasal and intratrachial route. Virus growth and antibody response was evaluated as described above.

Figure 8A:
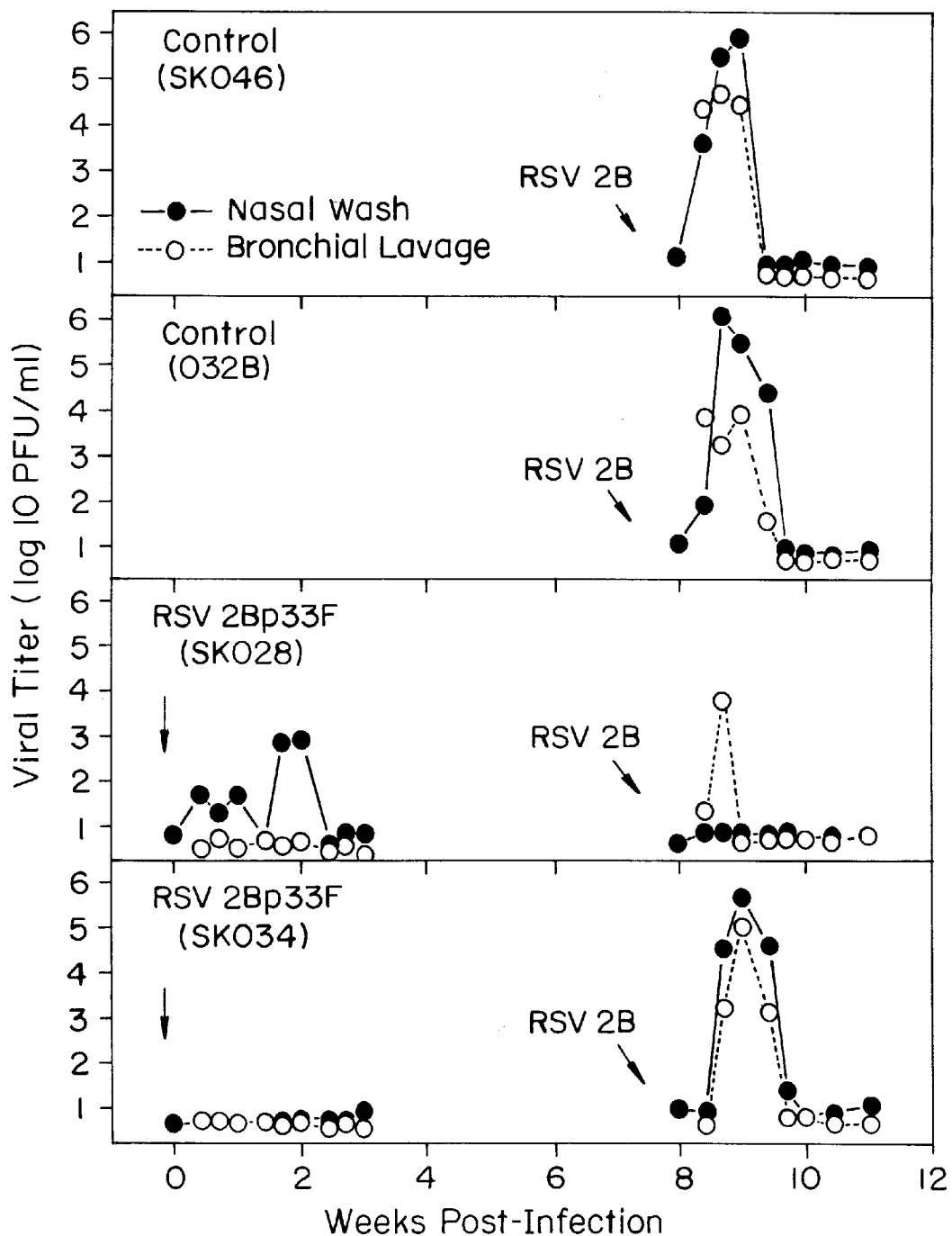
FIGS. 8A and 8B are diagrams showing virus titrations for monkeys infected with the RSV 2B TS mutants and subsequently challenged with the parental strain.
Figure 8B:
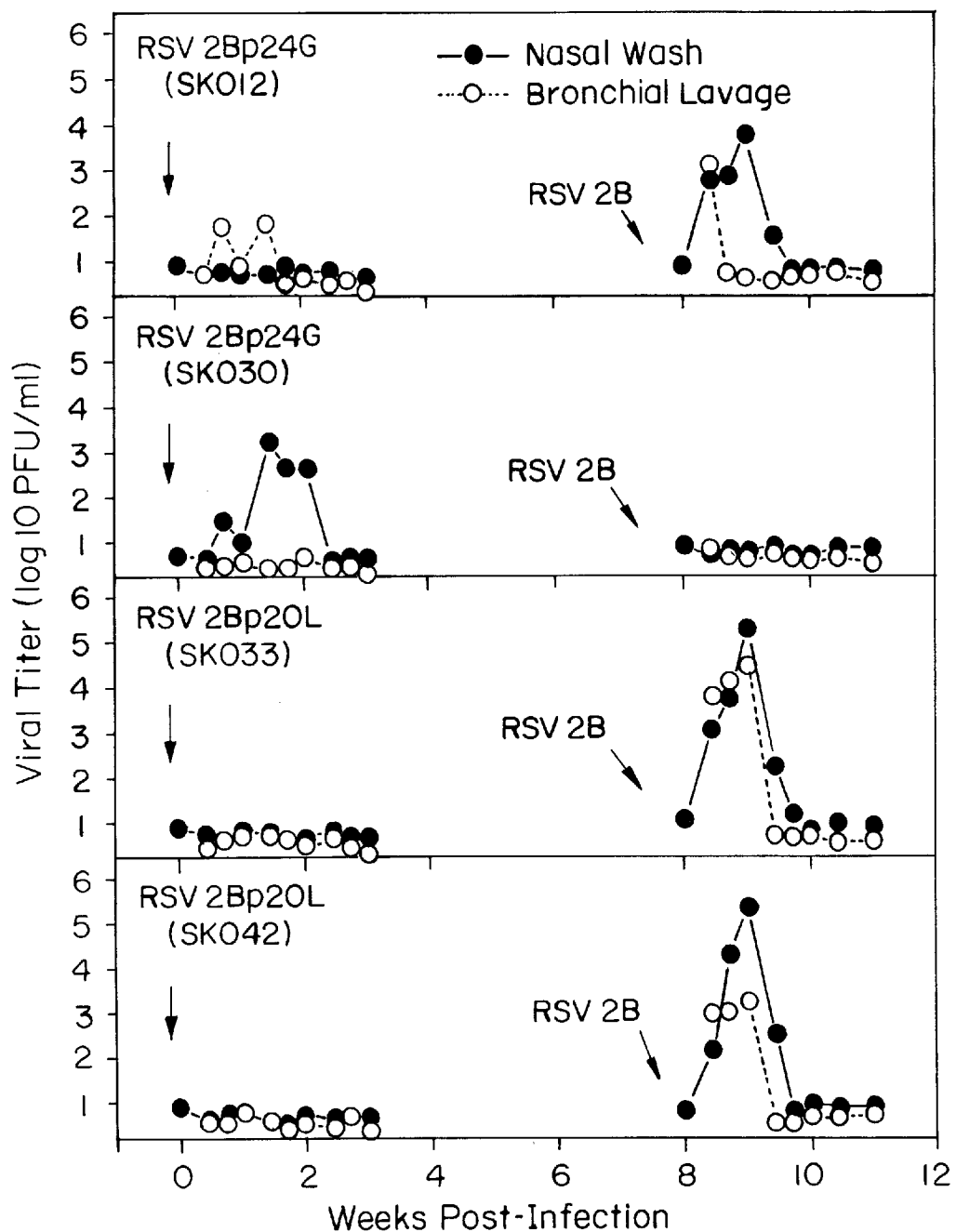
Figure 9A:
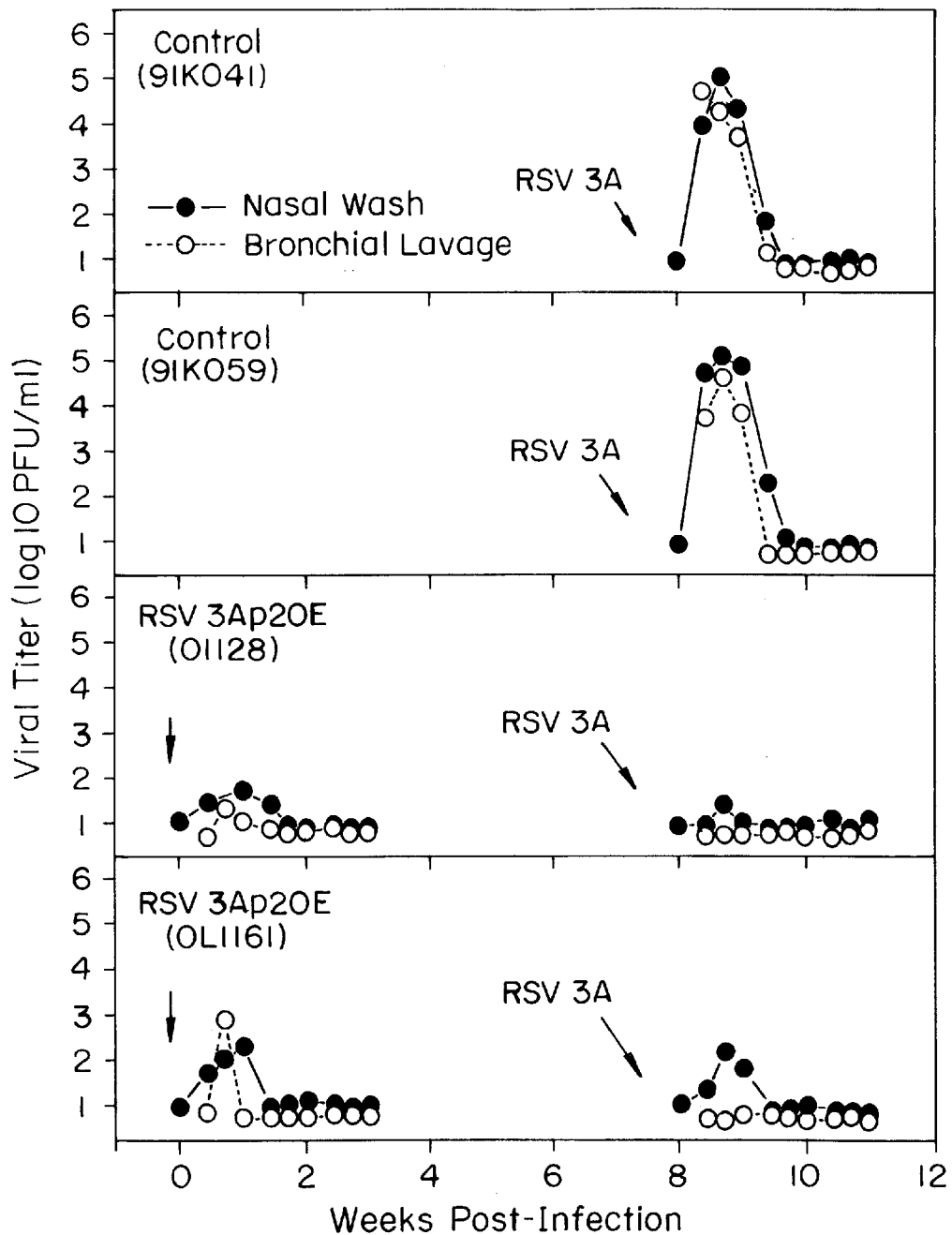
FIGS. 9A and 9B are diagrams showing virus growth in African green monkey cells infected with the RSV 3A TS mutants and challenged with the parental 3A strain.
Figure 9B:
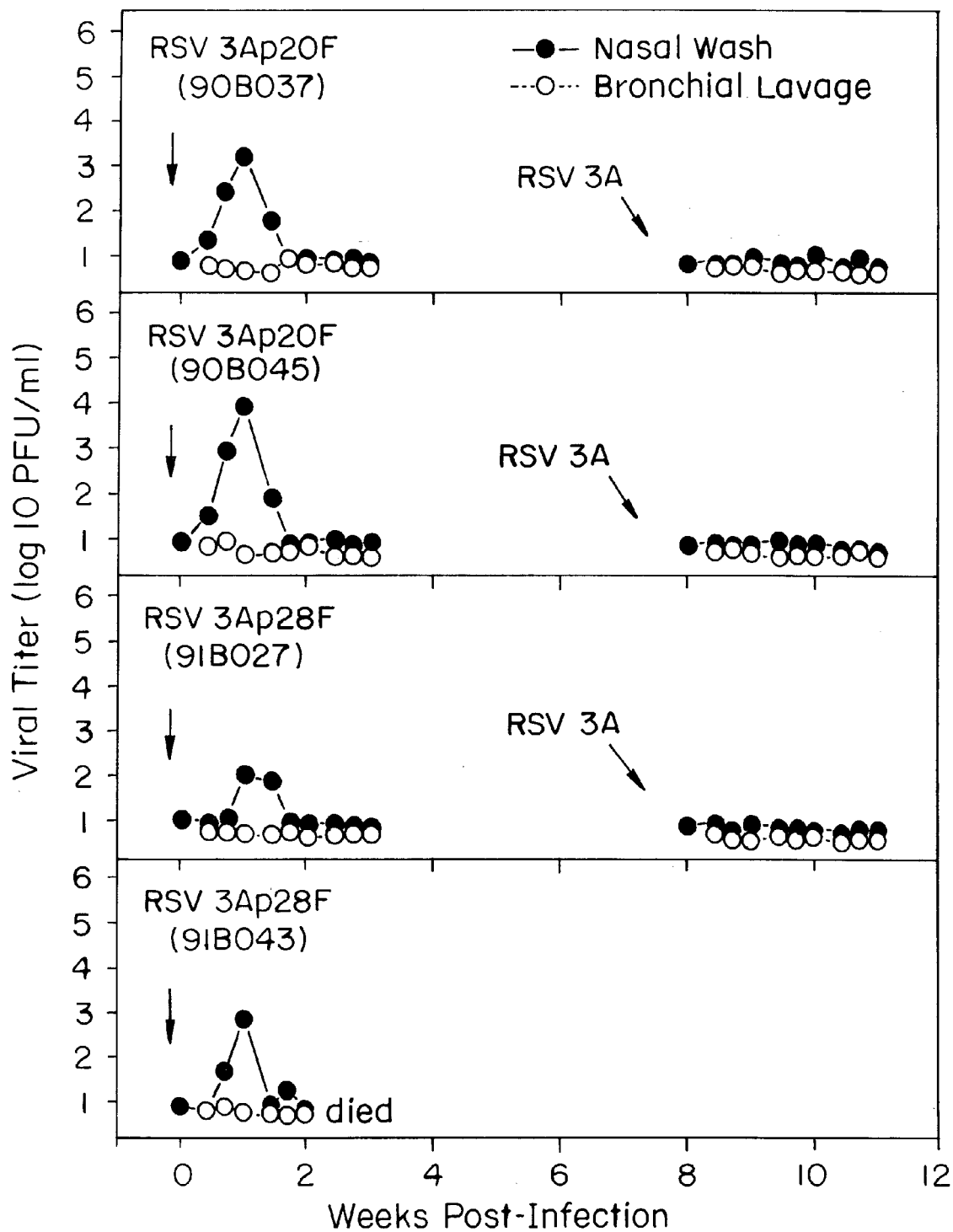

Growth of the parental RSV 2B and 3A strains can be seen in FIGS. 8 and 9: vaccine controls. Both virus strains grew to high titers in both the nose and lung. Nasal discharge and radiographic evidence of viral pneumonia was seen in one control monkey (032B) infected with RSV 2B, demonstrating that RSV is capable of causing disease in AGMs. These results confirm differences in these characteristics of infection in AGMs vs the cotton rat model, in which disease was not observed and RSV 3A was unable to replicate in the lung. Failure of the parental strains of RSV to cause disease in 3 of 4 monkeys suggests that the AGMs are not as susceptible a host as are humans.

Virus titrations for each monkey infected with the RSV 2B TS mutants and then challenged with the parental strain are shown in FIG. 8. RSV 2Bp33F grew to low levels in the nasal wash in 1 of 2 monkeys, RSV 2Bp24G grew to low levels in nasal wash or in lungs in both monkeys. RSV 2Bp20L failed to grow. In those AGMs where the RSV 2B TS mutants grew, monkeys were partially to fully protected against challenge with parental strain. Tables 16 and 17 give antibody titration results obtained for each monkey post-vaccination (Table 16) and post-virus challenge (Table 17). Results show that in monkeys where virus grew, low levels of neutralizing and EIA antibody titers were seen by 2.5 weeks post-infection. Following challenge with the parental strain, antibody titers boosted one full week earlier in vaccinated monkeys with antibody titers prior to challenge, than in vaccinated animals which failed to seroconvert or in unvaccinated controls. This demonstrated that vaccination with these TS mutants was sufficient to both prime the immune system and to elicit protection against virus challenge. Because these monkeys are not as susceptible to infection as humans, failure of attenuated virus to grow and to effectively immunize does not imply that virus would not be effective in a fully susceptible host (i.e. seronegative human infant).

Virus growth in AGMs infected with the RSV 3A TS mutants and challenged with the parental 3A strain are shown in FIG. 9. All 3 RSV 3A TS mutant strains were attenuated in growth, in the order of most to least attenuated: 3Ap28F>3Ap20E>3Ap20F. Vaccination with all 3 TS mutants afforded excellent protection against virus challenge. Antibody response for monkeys vaccinated with RSV 3A TS mutants is shown in Table 18, and response following virus challenge is shown in Table 19. In all vaccinated AGMs, with the exception of one monkey given RSV 3Ap28F, low levels of neutralizing and EIA antibody titers were detected beginning 3 weeks post-vaccination. Following challenge with the parental strain, all vaccinated monkeys boosted a full week earlier than the unvaccinated controls and were protected either fully or partially from infection, demonstrating that vaccination primed the immune response and was protective. This included the one AGM in which antibody response was not detected following vaccination, indicating that measure of serum antibody response may not be fully representative of level of protective immunity.

The results from the AGM studies again demonstrate that all six TS mutants tested were attenuated. Vaccination with those mutants which were able to replicate in these monkeys was efficacious in preventing infection with challenge virus.

Degree of Attenuation:

An RSV TS mutant, TS-1, was obtained from Dr. Brian Murphy, NIH. This TS mutant was originally derived from the RSV A2 strain by chemical mutagenesis and was tested in clinical trials in seronegative human infants in the 1970's. The outcome of these trials suggested that TS-1 was under-attenuated and caused an unacceptable level of disease (rhinitis and otitis media) in infants. In addition, the TS phenotype of TS-1 partially reverted following growth in humans. Experiments have been carried out which compare growth of the RSV 2B and 3A TS mutants with that of the TS-1 mutant in an attempt to assess the relative in vivo attenuation level of the RSV 2A and 3B mutants, and to demonstrate differences between these mutants and what had been used by others in previous clinical trials. The results of the cotton rat study are shown in Table 20, and may be compared directly with the cotton rat data shown in Tables 14 and 15. The TS-1 mutant was less attenuated than the RSV 2B and 3A TS mutants, as can most clearly be seen by comparing growth in the lung.

Figure 10A:
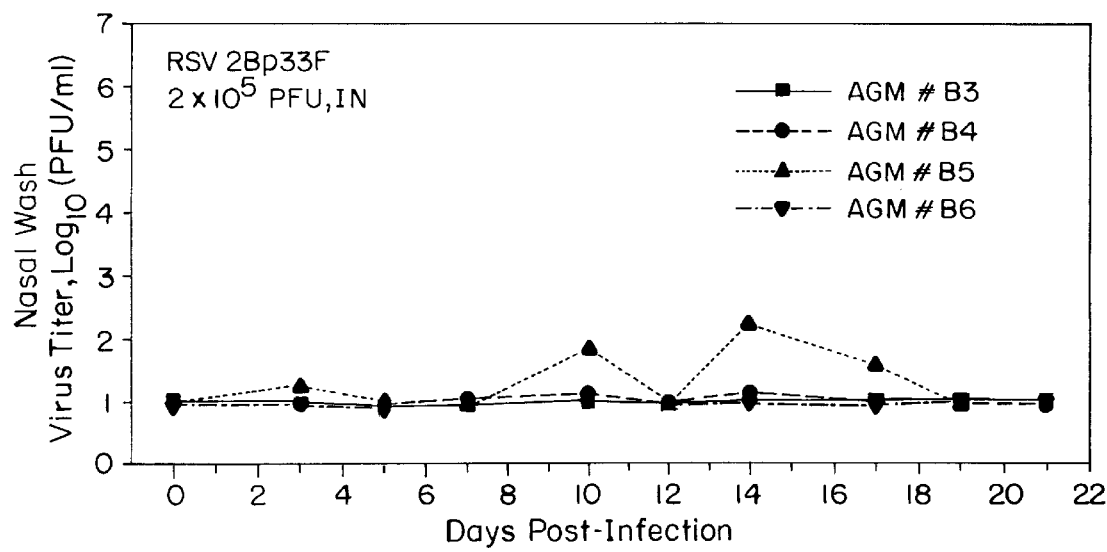
FIGS. 10A, 10B and 10C are diagrams showing a growth study in African green monkeys comparing TS-1 with RSV 2Bp33F and 3Ap28F.
Figure 10B:
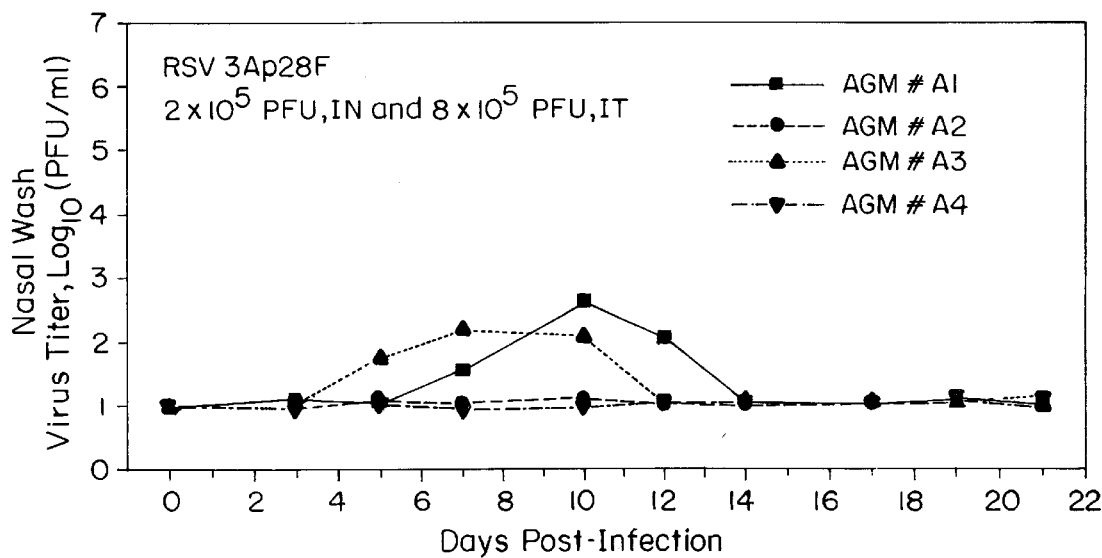
Figure 10C:
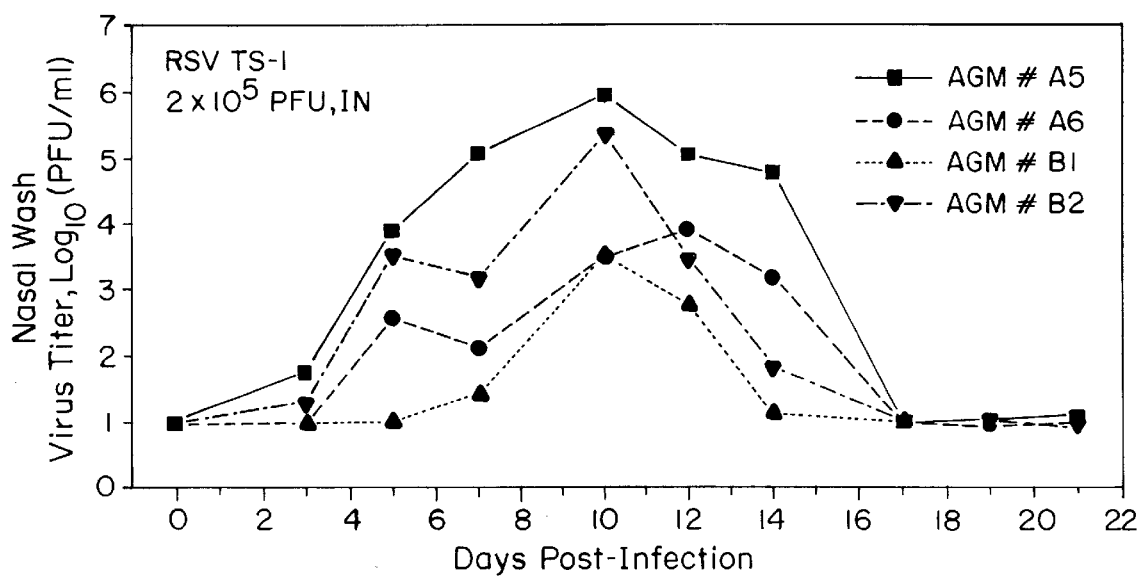

A growth study in African green monkeys (AGMs) comparing TS-1 with RSV 2Bp33F and 3Ap28F was carried out and the results are shown in FIG. 10. Monkeys were infected with virus either intranasally (TS-1 and 2Bp33F) or intranasally+intratracheally (3Ap28F). Virus was recovered in 1 of 4 monkeys infected with 2Bp33F and 2 of 4 monkeys infected with 3Ap28F. Titers were relatively low in both cases, indicating that virus was attenuated. In contrast, relatively high titers of virus were recovered in all 4 monkeys inoculated with TS-1. In 2 of 4 monkeys, the levels of TS-1 titers were equivalent to those seen in monkeys infected with wild type virus. TS-1 did not spread to the lungs, as would be expected for wild type virus, indicating that TS-1 was somewhat attenuated. The results clearly show that RSV 2Bp33F and 3Ap28F have different phenotypic characteristics than TS-1 and are significantly more attenuated. This higher level of attenuation is a property that is desirable for a vaccine to be administered to human infants.

Isolation of Monoclonal Antibodies

For the isolation of mouse monoclonal antibodies, eight (8) week old mice are inoculated intranasally with live RSV and/or are injected with about 50 micrograms of the purified polypeptide or mutant RSV in complete Freund's adjuvant 1:1 volume. Mice may then be boosted, at monthly intervals with the polypeptide or mutant RSV, this with incomplete Freund's adjuvant. Splenocytes are then fused with non-secreting myeloma cells, according to procedures which have been described and are known to those of skill in the art to which this invention pertains. Some time later, approximately two (2) weeks later, hybridoma supernatent is screened for binding activity against the polypeptide. Positive clones are isolated and propagated.

Isolates of human monoclonal antibodies can be done similarly, except B cells can be isolated from patients and transformed with Epstein-Barr Virus (EBV). The B cells are then fused with non-secreting myeloma cells according to procedures which have been described and are known to those of skill in the art to which this invention pertains. Some time later, approximately two (2) weeks later, hybridoma supernatent will be screened for binding activity against the polypeptide or mutant RSV. Positive clones are isolated and propagated. Alternatively human monoclonal antibodies can be prepared using methods described in U.S. Pat. Nos. 4,720,459, 4,693,975 or 4,574,116, the contents of which are hereby incorporated by reference. These monoclonal antibodies are useful for diagnostic assays and therapy.

Cold-Adaptation of Virus

This method comprises obtaining live virulent virus (RSV) derived from clinical isolates and that have been isolated in primary rhesus monkey kidney cells. These are then passed in Vero cells at 35–36° C. and plaque purified. Preferably, the Vero cells are passage 133 to 148 of the Vero cell line CCL81, obtained from the American Type Culture Collection (ATCC), 12301 Parklawn Drive, Rockville, Md., U.S.A. 20852. Maintenance medium is preferable MEM with 2% FBS, L-glutamine, non-essential amino acids and 20 mM Hepes pH 7.5, and freezing medium is MEM with 10% FBS and 20 mM Hepes pH 7.5.

A confluent monolayer of Vero cells are inoculated with about 1.0 ml of virus inoculum and virus is allowed to absorb for about 1 to 2 hours (preferably, 70 to 120 minutes, and most preferably 90 minutes) at ambient temperature (about 18° C. to about 25° C.).

The virus flask is incubated at about 18° C. to about 26° C., preferably about 20° C., for about two to fifteen days. Virus is harvested by removing the medium and replacing it with freezing medium. The flask is then frozen directly at −70° C., then thawed in a 32° C. water bath.

A portion (about 1 ml) is removed from the freeze thaw lysate and is used to inoculate Vero cells and the process is repeated. The remaining freeze-thaw lysate is stored at −70° C. It can be used to perform virus titrations and plaque purify virus.

To plaque purify virus, the freeze-thaw lysate is thawed in a 32° C. water bath. About 3 to 5 serial dilutions of the lysate is made in maintenance medium. Six-well, twenty-four well, or ninety-six well plates containing confluent Vero cells are rinsed with a phosphate buffered saline solution. Wells are inoculated with virus dilution, using only enough volume to cover the bottom of well. Virus inoculum is adsorbed for 90 minutes at ambient temperature. Wells are overlaid with 1% methylcellulose in MEM-maintenance medium. Plates are incubated at 32° C. for 5 days. Isolated plaques are identified microscopically by looking for typical syncytial plaques, and wells are marked. Plaques are picked at marked sites using small bore pipette or pipette tip and are emulsified in 0.5 ml maintenance medium for 1–3 hours at 4° C. Picked plaques are used to inoculate duplicates of 25 $cm^2$ flask or 96-well plates containing Vero cell monolayers as described above. Duplicate inoculated flasks or plates are overlaid with maintenance medium. One duplicate is incubated at 32° C. and the other at 39° C. for 5–10 days. Flasks or plates incubated at 32° C. are examined microscopically for virus CPE. Flasks or plates incubated at 39° C. are stained by immunoperoxidase assay for RSV specific antigen. Flasks or plates which demonstrate easily detectable CPE at 32° C. and little or no detectable RSV antigen by immunoperoxidase staining are selected as containing TS mutants. Virus from the selected flask or plate described above are harvested by freeze-thaw technique. This virus represents a plaque purified mutant.

DISCUSSION

Cold adaptation was used to develop attenuated strains of RSV from two parental strains derived from clinical isolates. Seven TS mutants were isolated, 4 from a subgroup B virus (RSV 2B) and 3 from a subgroup A virus (RSV 3A). All 7 mutants displayed a temperature sensitive phenotype in Vero cell culture, each with unique characteristics. All mutants were attenuated in growth in cotton rats, but displayed different phenotypes. Growth of one of the TS mutants, RSV 2Bp20L, was shown to be attenuated in seropositive chimpanzees. All 7 mutants retained 2 major neutralization epitopes.

Cold adaptation of RSV had previously been done in primary or diploid cell lines (bovine embryonic kidney, WI38, and cercopithecus monkey kidney) at temperatures beginning at 34° C.–37° C. and decreasing to 25° C.–26° C. No attempt had been made to isolate multiple individual mutant phenotypes from the cold adapted virus (Friedewald et al, 1968; Maassab and DeBorde, 1985; Frickey, 1969). This approach to cold adapting RSV differed in several significant ways from these previous attempts. This procedure started with a subgroup A and subgroup B virus of different strains than those used previously. These strains bore distinct phenotypic differences from the reference strains and each other. These strains were passed several times to adapt virus to Vero cells and to plaque purify virus. Virus was passaged in a continuous cell line, Vero cells, rather than a diploid or primary cell line. Several strategies of temperature change were used, to provide a greater potential for isolation of a variety of mutant phenotypes. Unlike previous RSV cold adaptation strategies where cold adaptation had started at 34–37° C. and gone down to 25–26° C., applicants started at either 26° C. (since applicants found that the parental strains grew well at this temperature) or 22° C., and gradually reduced the growth temperature to 20° C. Passage strategies attempted to cover both the recommendation of "slow" adaptation to very low temperatures as proposed by Maassab and DeBorde (1985), as well as efforts to try a faster and more aggressive approach. RNA viruses mutate at such a high frequency that any population of virus will contain a number of individual virus variants (Holland et al, 1982), therefore a variety of virus mutants were isolated from individual flasks at various virus passage levels and from different cold adaptation strategies. The results were interesting and somewhat unexpected. The rate at which virus became adapted (i.e., grew to consistently high titers at the 20° C. temperature), was most affected by the strain of virus used, implying a significant host-related factor in adaptation. RSV 2B easily adapted to the cold temperatures, even using a rapid adaptation scheme. In contrast, RSV 3A grew poorly at the low temperatures. RSV 3A was eventually cold adapted using the slow passage scheme, but the more rapid adaptation approaches did not appear promising and were discontinued. Based on cold adaptation experiences reported by other researchers, it was expected TS mutants would arise and eventually become the predominant virus variants in the cold adapted populations. For example, Belshe and Hissom (1982) reported that with parainfluenza virus type 3 adapted to grow at 20° C., 80% of plaque purified virus clones were TS by passage 18 and 100% were TS by passage 45. In this study, even after 38–40 low temperature passages, including up to 32 passages done at 20° C., RSV TS mutants remained a minor population. This would suggest that TS and cold adapted phenotypes may not be as strongly linked in RSV as they are in other viruses.

Level of attenuation is a critical factor in developing vaccines for any target population and is of particular importance for vaccines intended for infants and young children. Virus must be sufficiently attenuated to not cause disease, yet grow well enough in the vaccine to elicit protective immunity.

Widely accepted markers for attenuation are TS phenotype and reduced growth in animal models, however these markers are only approximate and testing must eventually be done in the target population. The RSV 3A TS mutants could be distinguished from the RSV 3A parental virus by reduced replication in both the nose and lungs. Also of note, although the RSV 3A parental virus grew much better in the nose than the lungs of cotton rats, virus recovery was similar in both nose and lungs of BALB/c mice. These data suggest that the attenuation seen in cotton rats is due to more than one factor, and that this factor is not directly related to temperature sensitivity as measured in vitro. The cotton rat is relatively nonpermissive for growth of RSV and disease does not develop, suggesting that this model is an unreliable indicator of level of attenuation in humans. In contrast, chimpanzees are highly susceptible to RSV infection and develop an upper and lower respiratory tract disease that is very similar to that seen in humans. In seropositive chimps applicants found the RSV 2B parental strain caused mild upper respiratory tract disease similar to that caused by natural RSV infections in adult humans. The RSV 2Bp20L mutant did not grow, clearly demonstrating that this TS mutant was attenuated in a permissive host as well as the non-permissive cotton rat. The level of attenuation is best assessed in a seronegative chimp, as prior virus exposure will affect the host response to virus challenge. Unfortunately, testing in seronegative chimps is severely hampered by the limited availability of these animals.

The mutants of this invention that have been examined here bear the desirable traits of an attenuated, phenotypically stable, and immunogenic RSV vaccine virus in the human target population.

TABLE 1

RSV 2B COLD ADAPTATION

E, F

| Passage # | Cumm. Time Passage Weeks | Incubation Temp ° C. | Time Days | Virus Yield $\log_{10}$PFU E | F |
|---|---|---|---|---|---|
| 1 | 0.2 | 26 | 2 | 6.9 | 6.7 |
| 2 | 0.4 | 26 | 2 | 6.0 | 6.1 |
| 3 | 0.6 | 26 | 2 | 5.5 | 5.6 |
| 4 | 0.8 | 26 | 2 | 4.5 | 4.7 |
| 5 | 1.0 | 26 | 7 | 4.9 | 5.0 |
| 6 | 2.0 | 26 | 7 | 6.2 | 6.3 |
| 7 | 3.0 | 26 | 7 | 7.9* | 7.6* |
| 8 | 4.0 | 22 | 7 | 7.5 | 7.6 |
| 9 | 5.0 | 22 | 7 | 7.3 | 7.3 |
| 10 | 6.0 | 22 | 7 | 7.2* | 7.2* |
| 11 | 7.0 | 22 | 7 | 7.5* | 7.7* |
| 12 | 8.0 | 22 | 7 | 8.0* | 7.9* |
| 13 | 9.0 | 22 | 7 | 8.0* | 7.9* |
| 14 | 10.0 | 20 | 7 | 7.6 | 7.7 |
| 15 | 11.0 | 20 | 7 | 7.0 | 5.9 |

TABLE 1-continued

RSV 2B COLD ADAPTATION

E, F

| Passage # | Cumm. Time Passage Weeks | Incubation Temp °C. | Incubation Time Days | Virus Yield log₁₀PFU E | Virus Yield log₁₀PFU F |
|---|---|---|---|---|---|
| 16 | 12.0 | 20 | 7 | 7.2 | 7.1 |
| 17 | 13.0 | 20 | 7 | 6.7 | 6.3 |
| 18 | 15.0 | 20 | 14 | 5.5 | 5.2 |
| 19 | 17.0 | 20 | 14 | 6.3 | 6.0 |
| 20 | 18.0 | 20 | 7 | 6.1 | 5.8 |
| 21 | 19.0 | 20 | 7 | 5.4 | 5.7 |
| 22 | 20.0 | 20 | 7 | 5.9 | 5.7 |
| 23 | 21.0 | 20 | 7 | 6.3 | 5.5 |
| 24 | 22.0 | 20 | 7 | 6.9 | 6.3 |
| 25 | 23.0 | 20 | 7 | 6.8 | 6.6 |
| 26 | 24.0 | 20 | 8 | 6.6 | 6.3 |
| 27 | 25.0 | 20 | 7 | 6.3 | 6.0 |
| 28 | 26.0 | 20 | 6 | 6.5 | 6.2 |
| 29 | 27.0 | 20 | 7 | 6.2 | 6.3 |
| 30 | 28.0 | 20 | 7 | 7.0 | 7.2 |
| 31 | 29.0 | 20 | 7 | 7.3 | 7.1 |
| 32 | 30.0 | 20 | 7 | 6.8 | 6.5 |
| 33 | 31.0 | 20 | 7 | 6.9 | 6.7 |
| 34 | 32.0 | 20 | 7 | 6.9 | 7.0 |
| 35 | 33.0 | 20 | 7 | 7.4 | 7.0 |
| 36 | 34.0 | 20 | 7 | 7.2 | 7.1 |
| 37 | 35.0 | 20 | 7 | 7.4 | 7.0 |
| 38 | 36.0 | 20 | 7 | 7.4 | 7.1 |
| 39 | 37.0 | 20 | 7 | 7.5 | 7.0 |
| 40 | 36.0 | 20 | 7 | 7.2 | 6.7 |

*Syncytial CPE seen at harvest

TABLE 1b

RSV 2B COLD ADAPTATION

G, H

| Passage # | Cumm. Time Passage Weeks | Incubation Temp °C. | Incubation Time Days | Virus Yield log₁₀PFU G | Virus Yield log₁₀PFU H |
|---|---|---|---|---|---|
| 1 | 0.3 | 26 | 3 | 7.1 | 7.1 |
| 2 | 0.7 | 26 | 3 | 6.9 | 6.9 |
| 3 | 1.0 | 22 | 7 | 6.4 | 6.4 |
| 4 | 2.0 | 22 | 7 | 6.4 | 6.3 |
| 5 | 3.0 | 22 | 7 | 6.6 | 6.4 |
| 6 | 4.0 | 22 | 7 | 6.9 | 6.8 |
| 7 | 5.0 | 22 | 7 | 6.9 | 6.7 |
| 8 | 6.0 | 20 | 7 | 6.3 | 6.3 |
| 9 | 7.0 | 20 | 7 | 6.2 | 6.3 |
| 10 | 8.0 | 20 | 7 | 6.6 | 6.9 |
| 11 | 9.0 | 20 | 7 | 7.0 | 7.0 |
| 12 | 10.0 | 20 | 7 | 7.0 | 7.4 |
| 13 | 11.0 | 20 | 7 | 6.3 | 7.3 |
| 14 | 12.0 | 20 | 7 | 7.7 | 7.9 |
| 15 | 13.0 | 20 | 7 | 7.2 | 7.4 |
| 16 | 15.0 | 20 | 14 | 6.4 | 6.3 |
| 17 | 16.0 | 20 | 8 | 6.8 | 6.9 |
| 18 | 17.0 | 20 | 6 | 6.9 | 7.0 |
| 19 | 18.0 | 20 | 7 | 6.9 | 7.1 |
| 20 | 19.0 | 20 | 7 | 6.7 | 7.0 |
| 21 | 20.0 | 20 | 7 | 6.4 | 6.8 |
| 22 | 21.0 | 20 | 7 | 6.5 | 7.0 |
| 23 | 22.0 | 20 | 7 | 6.9 | 7.1 |
| 24 | 23.0 | 20 | 7 | 6.8 | 6.7 |
| 25 | 24.0 | 20 | 8 | 6.4 | 6.2 |
| 26 | 25.0 | 20 | 7 | 6.0 | 5.5 |
| 27 | 26.0 | 20 | 6 | 6.3 | 5.5 |
| 28 | 27.0 | 20 | 7 | 6.5 | 5.9 |
| 29 | 28.0 | 20 | 7 | 7.1 | 6.4 |
| 30 | 29.0 | 20 | 7 | 6.1 | 7.1 |
| 31 | 30.0 | 26 | 7 | 6.4 | 5.5 |
| 32 | 31.0 | 20 | 7 | 6.2 | 5.9 |
| 33 | 32.0 | 20 | 7 | 6.4 | 6.2 |
| 34 | 33.0 | 20 | 7 | 6.4 | 6.9 |
| 35 | 34.0 | 20 | 7 | 6.9 | 6.5 |
| 36 | 35.0 | 20 | 7 | 7.0 | 6.7 |
| 38 | 37.0 | 20 | 7 | 7.1 | 7.2 |

TABLE 1c

RSV 2B COLD ADAPTATION

J, L

| Passage # | Cumm. Time Passage Weeks | Incubation Temp °C. | Incubation Time Days | Virus Yield log₁₀PFU J | Virus Yield log₁₀PFU L |
|---|---|---|---|---|---|
| 1 | 1.0 | 22 | 7 | 6.8 | |
| 2 | 2.0 | 22 | 7 | 7.1 | |
| 3 | 3.0 | 22 | 7 | 6.7 | |
| 4 | 4.0 | 22 | 7 | 5.9 | 6.1 |
| 5 | 5.0 | 22 | 7 | 4.8 | 5.7 |
| 6 | 6.0 | 20 | 7 | 4.9 | 5.0 |
| 7 | 7.0 | 20 | 7 | 4.8 | 4.9 |
| 8 | 9.0 | 20 | 14 | 6.0 | 6.0 |
| 9 | 11.0 | 20 | 14 | 6.6 | 6.3 |
| 10 | 12.0 | 20 | 7 | 6.9 | 6.9 |
| 11 | 13.0 | 20 | 7 | 6.6 | 6.7 |
| 12 | 15.0 | 20 | 14 | 6.0 | 6.0 |
| 13 | 16.0 | 20 | 8 | 6.3 | 6.2 |
| 14 | 17.0 | 20 | 6 | 6.2 | 6.5 |
| 15 | 18.0 | 20 | 7 | 6.6 | 6.7 |
| 16 | 19.0 | 20 | 7 | 6.4 | 6.9 |
| 17 | 20.0 | 20 | 7 | 6.5 | 6.9 |
| 18 | 21.0 | 20 | 7 | 6.9 | 7.0 |
| 19 | 22.0 | 20 | 7 | 7.4 | 7.4 |
| 20 | 23.0 | 20 | 7 | 7.2 | 7.4 |
| 21 | 24.0 | 20 | 8 | 7.0 | 7.1 |
| 22 | 25.0 | 20 | 7 | 6.8 | 6.9 |
| 23 | 26.0 | 20 | 6 | 6.9 | 7.0 |
| 24 | 27.0 | 20 | 7 | 7.0 | 7.0 |
| 25 | 28.0 | 20 | 7 | 7.8 | 7.4 |
| 26 | 29.0 | 20 | 7 | 7.5 | 7.3 |
| 27 | 30.0 | 20 | 7 | 6.8 | 6.7 |
| 28 | 31.0 | 20 | 7 | 6.9 | 6.8 |
| 29 | 32.0 | 20 | 7 | 7.0 | 6.9 |
| 30 | 33.0 | 20 | 7 | 7.4 | 7.2 |
| 31 | 34.0 | 20 | 7 | 7.3 | 6.7 |
| 32 | 35.0 | 20 | 7 | 7.3 | 6.9 |
| 33 | 36.0 | 20 | 7 | 7.3 | 7.0 |
| 34 | 37.0 | 20 | 7 | 7.2 | 6.9 |
| 35 | 38.0 | 20 | 7 | 6.6 | 6.3 |

TABLE 2a

RSV 3A COLD ADAPTATION

E

| Passage # | Cumm. Time Passage Weeks | Incubation Temp °C. | Time Days | Virus Yield $\log_{10}$PFU E |
|---|---|---|---|---|
| 1 | 0.2 | 26 | 2 | 6.2 |
| 2 | 0.4 | 26 | 2 | 5.1 |
| 3 | 0.6 | 26 | 2 | 4.7 |
| 4 | 0.8 | 26 | 2 | 3.8 |
| 5 | 1.0 | 26 | 7 | 4.0 |
| 6 | 2.0 | 26 | 7 | 5.0 |
| 7 | 3.0 | 26 | 7 | 6.1 |
| 8 | 4.0 | 22 | 7 | 6.0 |
| 9 | 5.0 | 22 | 7 | 5.6 |
| 10 | 6.0 | 22 | 7 | 5.8 |
| 11 | 7.0 | 22 | 7 | 5.7 |
| 12 | 8.0 | 22 | 7 | 5.9 |
| 13 | 9.0 | 22 | 7 | 5.9 |
| 14 | 11.0 | 20 | 14 | 5.8 |
| 15 | 13.0 | 20 | 14 | 6.1 |
| 16 | 15.0 | 20 | 14 | 4.8 |
| 17 | 17.0 | 20 | 14 | 4.9 |
| 18 | 19.0 | 20 | 14 | 4.8 |
| 19 | 20.0 | 20 | 7 | 4.3 |
| 20 | 22.0 | 20 | 14 | 4.9 |
| 21 | 24.0 | 20 | 14 | 5.2 |
| 22 | 26.0 | 20 | 15 | 5.6 |
| 23 | 28.0 | 20 | 13 | 6.3 |
| 24 | 30.0 | 20 | 14 | 6.3 |
| 25 | 32.0 | 20 | 14 | 7.3 |
| 26 | 34.0 | 20 | 14 | 7.8 |
| 27 | 36.0 | 20 | 14 | 7.2 |
| 28 | 38.0 | 20 | 14 | 7.4 |
| 29 | 40.0 | 20 | 14 | 6.8 |
| 30 | 42.0 | 20 | 14 | 7.3 |

TABLE 2b

RSV 3A COLD ADAPTATION

F

| Passage # | Cumm. Time Passage Weeks | Incubation Temp °C. | Time Days | Virus Yield $\log_{10}$PFU F |
|---|---|---|---|---|
| 1 | 0.2 | 26 | 2 | 6.1 |
| 2 | 0.4 | 26 | 2 | 5.1 |
| 3 | 0.6 | 26 | 2 | 4.7 |
| 4 | 0.8 | 26 | 2 | 3.6 |
| 5 | 1.0 | 26 | 7 | 4.3 |
| 6 | 2.0 | 26 | 7 | 5.3 |
| 7 | 3.0 | 26 | 7 | 6.4 |
| 8 | 4.0 | 22 | 7 | 6.3 |
| 9 | 5.0 | 22 | 7 | 5.2 |
| 10 | 6.0 | 22 | 7 | 5.8 |
| 11 | 7.0 | 22 | 7 | 5.7 |
| 12 | 8.0 | 22 | 7 | 6.0 |
| 13 | 9.0 | 22 | 7 | 5.6 |
| 14 | 11.0 | 20 | 14 | 5.5 |
| 15 | 13.0 | 20 | 14 | 5.4 |
| 16 | 15.0 | 20 | 14 | 3.9 |
| 17 | 17.0 | 20 | 14 | 3.7 |
| 18 | 19.0 | 20 | 14 | 3.5 |
| 19 | 21.0 | 20 | 14 | 3.8 |
| 20 | 23.0 | 20 | 14 | 4.2 |
| 21 | 25.0 | 20 | 15 | 3.2 |
| 22 | 27.0 | 20 | 13 | 3.9 |
| 23 | 29.0 | 20 | 14 | 4.5 |
| 24 | 31.0 | 20 | 14 | 4.7 |
| 25 | 33.0 | 20 | 14 | 4.8 |
| 26 | 35.0 | 20 | 14 | 5.3 |
| 27 | 37.0 | 20 | 14 | 5.5 |
| 28 | 39.0 | 20 | 14 | 5.8 |

TABLE 2c

RSV 3A COLD ADAPTATION

H, I

| Passage # | Cumm. Time Passage Weeks | Incubation Temp °C. | Time Days | Virus Yield $\log_{10}$PFU H | I |
|---|---|---|---|---|---|
| 1 | 0.3 | 26 | 3 | 6.9 | 7.0 |
| 2 | 0.7 | 26 | 3 | 6.1 | 6.4 |
| 3 | 1.0 | 22 | 7 | 5.8 | 5.8 |
| 4 | 2.0 | 22 | 7 | 5.8 | 5.9 |
| 5 | 3.0 | 22 | 7 | 5.9 | 5.7 |
| 6 | 4.0 | 22 | 7 | 5.6 | 5.5 |
| 7 | 5.0 | 22 | 7 | 5.1 | 5.1 |
| 8 | 6.0 | 20 | 7 | 4.0 | 3.8 |
| 9 | 7.0 | 20 | 7 | 3.3 | 2.8 |
| 10 | 9.0 | 20 | 14 | 3.9 | 3.2 |
| 11 | 11.0 | 20 | 14 | 3.9 | 3.1 |
| 12 | 13.0 | 20 | 14 | 4.0 | 3.0 |

J, L

| Passage # | Cumm. Time Passage Weeks | Incubation Temp °C. | Time Days | Virus Yield $\log_{10}$PFU J | L |
|---|---|---|---|---|---|
| 1 | 1.0 | 22 | 7 | 6.7 | |
| 2 | 2.0 | 22 | 7 | 6.7 | |
| 3 | 3.0 | 22 | 7 | 6.0 | |
| 4 | 4.0 | 22 | 7 | 5.7 | 5.6 |
| 5 | 5.0 | 22 | 7 | 4.2 | 4.9 |
| 6 | 6.0 | 20 | 7 | 3.7 | 3.7 |
| 7 | 7.0 | 20 | 7 | 3.1 | 3.0 |
| 8 | 9.0 | 20 | 14 | 2.8 | 3.2 |
| 9 | 11.0 | 20 | 14 | 2.3 | 3.3 |
| 10 | 13.0 | 20 | 14 | 3.0 | 2.8 |

TABLE 3

Summary of Cold Adaptation Passage History.

| | #Parental Virus Passage | | | | | #Cold Adaptation Passage | | | |
| | PRMK | Vero | | | | Vero | | | |
| Virus | 35° C. | 35° C. | 36° C. | Total | Flask | 26° C. | 22° C. | 20° C. | Total |
|---|---|---|---|---|---|---|---|---|---|
| 2B | 7 | 2 | 12 | 21 | E, F | 7 | 6 | 27 | 40 |
| | | | | | G, H | 2 | 5 | 32 | 39 |
| | | | | | J, L | 0 | 5 | 30 | 35 |
| 3A | 8 | 2 | 12 | 22 | E | 7 | 6 | 17 | 30 |
| | | | | | F | 7 | 6 | 15 | 28 |
| | | | | | H, I | 2 | 5 | 5 | 12 |
| | | | | | J, L | 0 | 5 | 5 | 10 |

TABLE 4

Efficiency of Plaquing of Cold Passaged Virus

| | EOP 39/32° C. | |
| Virus | Week 5 | Week 17 |
|---|---|---|
| 23 | 0.8 | 0.6 |
| 2B-E | 0.6 | 0.6 |
| 2B-F | 0.8 | 0.7 |
| 2B-G | 0.6 | 0.8 |
| 2B-H | 0.7 | 0.4 |
| 2B-J | ND | 0.9 |
| 2B-L | 0.7 | 0.6 |
| 3A | 0.6 | 0.6 |
| 3A-E | 0.6 | 0.4 |
| 3A-F | 0.8 | 0.2 |
| 3A-H | 0.6 | ND |
| 3A-I | 0.9 | ND |
| 3A-J | 0.6 | ND |
| 3A-L | 0.6 | ND |

TABLE 5

TS Mutants Plaque Purified from Cold Adapted Virus

| | RSV 2B | | | RSV 3A | |
| Cumm./Passage Weeks # | #TS/#Total Plaques Isolated | | Cumm./Passage Weeks # | #TS/#Total Plaques Isolated | |
|---|---|---|---|---|---|
| | E | F | | E | |
| wk23/p25 | 0/10 | 1/10 | wk22/p20 | 2/10 | |
| wk31/p33 | 0/10 | 1/10 | wk32/p25 | 1/10 | |
| wk38/p40 | 0/10 | 1/10 | wk42/p30 | 3/9 | |
| | G | H | | F | |
| wk23/p24 | 1/10 | 2/10 | wk23/p20 | 1/9 | |
| wk31/p32 | 0/10 | 2/10 | wk31/p24 | 0/10 | |
| wk38/p39 | 1/10 | 4/10 | wk37/p27 | 1/10 | |
| | | | wk39/p28 | 2/5 | |
| | J | L | | | |
| wk23/p20 | 0/9 | 1/10 | | | |

TABLE 5-continued

TS Mutants Plaque Purified from Cold Adapted Virus

| | RSV 2B | | RSV 3A | |
| Cumm./Passage Weeks # | #TS/#Total Plaques Isolated | | Cumm./Passage Weeks # | #TS/#Total Plaques Isolated |
|---|---|---|---|---|
| wk31/p28 | 0/10 | 0/10 | | |
| wk37/p34 | 0/8 | 2/9 | | |
| wk38/p35 | 1/20 | 3/8 | | |

TABLE 6

Summary of EOP Data on Twice Plaque Purified RSV TS Mutants

| | EOP | | |
| RSV Isolate | 37/32° C. | 39/32° C. | 40/32° C. |
|---|---|---|---|
| 2B (parent) | 0.7–1.0 | 0.6–0.8 | 0.4 |
| 2Bp33F (pp10-1) | 0.5 | 0.002 | ND |
| 2Bp40F (pp7-2) | 0.9 | 0.0008 | ND |
| 2Bp24G (pp2-1) | 0.2 | 0.00001 | <0.00001 |
| 2Bp39G (pp7-3) | 1.0 | 0.009 | ND |
| 2Bp24H (pp3-2) | ND | 0.003 | 0.001 |
| 2Bp32H (pp6-2) | 0.9 | 0.03 | ND |
| 2Bp39H (pp6-5) | 1.0 | 0.04 | ND |
| 2Bp35J (pp2-1) | 0.4 | 0.2 | ND |
| 2Bp20L (pp5-1) | 0.02 | ND | <0.00001 |
| 2Bp34L (pp2-2) | 0.005 | 0.0005 | ND |
| 2Bp35L (pp1-1) | 0.3 | 0.02 | ND |
| 2Bp35L (pp2-1) | 0.5 | 0.1 | ND |
| 2Bp35L (pp8-3) | 0.2 | 0.05 | ND |
| 3A (parent) | 1.0 | 0.5–0.9 | 0.6 |
| 3Ap20E (pp3-1) | 0.6 | 0.006 | 0.000009 |
| 3Ap25E (pp7-5) | 0.5 | 0.2 | ND |
| 2Ap30E (pp3-1) | 0.4 | 0.08 | ND |
| 3Ap20F (pp4-3) | 0.8 | >0.1 | 0.000004 |
| 3Ap27F (pp1-2) | 0.3 | 0.003 | ND |
| 3Ap28F (pp10-1) | 0.2 | 0.002 | ND |

ND = Not Done

TABLE 7

RSV INFECTION OF BALB/C MICE: ATTENUATION AND IMMUNOGENICITY

| Virus Strain | Dose $Log_{10}$ Pfu | Infection Rate | Nasal Wash $Log_{10}$ PFU/ml day 4 | day 5 | Lung Tissue $Log_{10}$ PFU/G day 4 | day 5 | Antibody Titers[+] Neut. 2B | 3A | A2 |
|---|---|---|---|---|---|---|---|---|---|
| 2B (parental) | 6.2 | 8/8[F] | 2.0 | 1.9 | 2.8 | 2.0* | 17 | 21 | <8 |
| 2B-CAp20L | 6.3 | 0/8 | N.P. | N.P. | N.P. | N.P. | <8 | <8 | <8 |
| 3A (parental) | 6.0 | 8/8 | 1.4 | 0.5* | 2.3* | 2.6 | 19 | 57 | 11 |
| 3A-CAp20E | 6.5 | 0/8 | N.P. | N.P. | N.P. | N.P. | <8 | <8 | <8 |
| Vero | — | 0/8 | N.P. | N.P. | N.P. | N.P. | <8 | <8 | <8 |

N.P. = No plaques
* = Values are below optimal detection limits of assay based on a minimum of 1 plaque per well.
+ = Sera was taken 32 days post-infection.
Neutralization results are expressed as the reciprocal of the dilution giving 60% plaque reduction neutralization, again RSV 2B, 3A, and A2
F = Infection rate = # of mice positive for RSV/Total # of mice inoculated.

TABLE 8

Summary of RSV TS Mutant Passage History.

| | PRMK | Adaptation and Plaque Purification (×3) (parental virus) | | | Cold Adaptation | | | Plaque Purification (×3) + expansion |
|---|---|---|---|---|---|---|---|---|
| Virus | 35° C. | 35° C. | 36° C. | 26° C. | 22° C. | 20° C. | | 32° C. |
| 2Bp33F pp10-1-2 | 7 | 2 | 12 | 7 | 6 | 20 | | 6 |
| 2Bp24G pp2-1-1 | 7 | 2 | 12 | 2 | 5 | 17 | | 5 |
| 2Bp20L pp5-1-1 | 7 | 2 | 12 | — | 5 | 15 | | 5 |
| 2Bp34L pp2-2-2 | 7 | 2 | 12 | — | 5 | 29 | | 5 |
| 3Ap20E pp3-1-1 | 8 | 2 | 12 | 7 | 6 | 7 | | 5 |
| 3Ap20F pp4-3-1 | 8 | 2 | 12 | 7 | 6 | 7 | | 5 |
| 3Ap28F pp10-1-2 | 8 | 2 | 12 | 7 | 6 | 15 | | 5 |

TABLE 9

EOP AND PLAQUE MORPHOLOGY OF RSV 2B AND RSV 3A TS MUTANTS IN VERO CELLS

| VIRUS | TEMPERATURE (° C.) | EOP | PLAQUE MORPHOLOGY OBSERVATIONS |
|---|---|---|---|
| 2B | 32° | 1.0 | 99% WT |
| | 37° | 0.9 | H, Most WT |
| | 39° | 0.6 | 99% WT |
| 2Bp33F pp10-1-2, V + 3 | 32° | 1.0 | ⅓ SP, I, WT |
| | 37° | 0.01 | Mostly SP, F |
| | 39° | 0.00005 | 95% SP, D, Few WT |
| 2Bp24G pp2-1-1, V + 3 | 32° | 1.0 | ⅓ SP, I, WT |
| | 37° | 0.09 | H, SP and I |
| | 39° | 0.004 | ⅓ SP, I, WT |
| 2Bp20L pp5-1-1, V + 4 | 32° | 1.0 | H, ⅓ WT |
| | 37° | 0.01 | ⅓ SP, I, WT |
| | 39° | 0.0002 | ⅓ SP, I, WT |
| 2Bp34L pp2-2-2, V + 3 | 32° | 1.0 | H, Mostley I |
| | 37° | 0.002 | Mostly SP, F |
| | 39° | 0.0001 | Very SP, No WT |
| 3A | 32° | 1.0 | 99% WT |
| | 37° | 0.9 | Mostly WT |
| | 39° | 0.5 | Mostly WT |
| 3Ap20E pp3-1-1, V + 4 | 32° | 1.0 | Mostly I |
| | 37° | 0.8 | Mostly I, ⅓ SP |
| | 39° | 0.04 | 95% SP, I, F, Few WT |
| 3Ap20F pp4-3-1, V + 3 | 32° | 1.0 | Mostly I and WT |
| | 37° | 0.7 | Mostly I and WT |
| | 39° | 0.1 | Mostly SP, I, No WT |
| 3Ap28F pp10-1-2, V + 3 | 32° | 1.0 | Mostly SP and I |
| | 37° | 0.4 | Mostly I, F, Few WT |
| | 39° | 0.01 | 90% SP, I, F, Few WT |

Abbreviations:
SP Small Plaque
I Intermediate
WT Wild Type
D Dark Stained
F Faint Stained
H Heterogeneous

TABLE 10

TEMPERATURE-RELATED GROWTH OF RSV 2B AND RSV 3A STRAINS IN VERO CELLS: FOUR DAY VIRUS YIELDS

| | Virus Yield PFU/Cell | | | |
|---|---|---|---|---|
| Virus | 32° C. | 37° C. | 39° C. | 40° C. |
| 2B | 0.8 | 0.6 | 0.4 | 0.1 |
| 2Bp33F pp10-1-2, V + 3 | 0.5 | 0.01 | ≦0.00008 | <0.000005 |

TABLE 10-continued

TEMPERATURE-RELATED GROWTH OF RSV 2B AND RSV 3A STRAINS IN VERO CELLS: FOUR DAY VIRUS YIELDS

| | Virus Yield | | | |
|---|---|---|---|---|
| | PFU/Cell | | | |
| Virus | 32° C. | 37° C. | 39° C. | 40° C. |
| 2Bp24G pp2-1-1, V + 3 | 1.0 | 0.08 | 0.0003 | 0.00001 |
| 2Bp20L pp5-1-1, V + 4 | 0.5 | 0.01 | 0.00003 | 0.000007 |
| 2Bp34L pp2-2-2, V + 3 | 0.008 | <0.000005 | <0.000005 | ≦0.000007 |
| 3A | 1.6 | 0.3 | 0.08 | 0.05 |
| 3Ap20E pp3-1-1, V + 4 | 0.2 | 0.02 | ≦0.000006 | <0.000006 |
| 3Ap20F pp4-3-1, V + 3 | 0.5 | 0.05 | 0.00005 | <0.000006 |
| 3Ap28F pp10-1-2, V + 3 | 0.2 | 0.006 | ≦0.000006 | <0.000006 |

TABLE 11

Monoclonal Antibody Neutralization of RSV 2B and RSV 3A Parental and TS Mutants

| | Neutralization Titers | |
|---|---|---|
| Challenge Strains | 143-6C | 133-1H |
| 2B | 15,091 | 46,775 |
| 2Bp33F | 23,364 | 32,690 |
| 2Bp24G | >25,600 | 32,571 |
| 2Bp20L | 25,972 | 32,790 |
| 2Bp34L | 16,757 | 77,172 |
| 3A | 99,814 | 46,493 |
| 3Ap20E | 76,203 | >25,600 |
| 3Ap20F | 69,513 | 13,743 |
| 3Ap28F | 80,436 | 34,136 |

Note: Neutralizations were done by a standard 60% plaque reduction neutralization assay on Vero cell monolayers in 96-well microtiter plates. Challenge with a 1:400 dilution of non-neutralizing monoclonal antibody 131-2G showed no reduction in titer in any of the nine strains.

TABLE 12

RSV TS Mutant Infection of Cotton Rats - 4 Days Post-Infection

| | | | Virus Growth | | Immunogenicity* | | | | | |
|---|---|---|---|---|---|---|---|---|---|---|
| | | | GMT+ $\text{Log}_{10}$ PFU/gm | | | PRNT Challenge Virus | | | | |
| Virus Strain | Dose $\text{Log}_{10}$ Pfu | Infection Rate | Nasal | Lung | Sero(+) Rate | RSV 2B | RSV A2 | RSV 3A | EIA-F | EIA-Ga | EIA-Gb |
| 2B | 6.5 | 4/4 | 5.48 (0.19) | 5.00 (0.42) | 4/4 | 2.80 (0.36) | 2.26 (0.52) | 3.42 (0.40) | 3.43 (0.14) | ≦1.95 (0.30) | 3.23 (0.13) |
| 2Bp33F | 7.3 | 4/4 | 1.88 (0.28) | <1.30 (0.12) | 4/4 | 2.24 (0.22) | 1.86 (0.48) | 2.95 (0.25) | 2.76 (0.26) | <1.70 | 2.33 (0.25) |
| 2Bp24G | 6.9 | 4/4 | 1.73 (0.33) | ≦1.30 (0.08) | 4/4 | 1.58 (0.23) | ≦1.05 (0.05) | 2.33 (0.24) | 2.62 (0.34) | ≦1.71 (0.01) | 2.10 (0.32) |
| 2Bp20L | 7.0 | 0/4 | <1.92 (0.11) | <1.30 (0.12) | 2/3 | ≦1.26 (0.24) | ≦1.01 (0.02) | ≦1.25 (0.31) | ≦2.05 (0.32) | <1.70 | <1.70 |
| 2Bp34L | 5.6 | 1/4 | ≦1.73 (0.05) | <1.33 (0.10) | 1/3 | ≦1.03 (0.06) | <1.00 | ≦1.08 (0.08) | <1.70 | <1.70 | <1.70 |
| 3A | 6.3 | 4/4 | 5.70 (0.23) | 2.00 (0.42) | 4/4 | 2.31 (0.13) | 2.28 (0.28) | 3.12 (0.31) | 3.55 (0.18) | 2.28 (0.29) | ≦1.93 (0.46) |
| 3Ap20E | 6.5 | 4/4 | 4.97 (0.22) | ≦1.40 (0.22) | 4/4 | 2.09 (0.05) | 1.74 (0.09) | 2.59 (0.16) | 3.40 (0.18) | 2.61 (0.58) | 2.18 (0.32) |
| 3Ap20F | 6.7 | 4/4 | 4.95 (0.13) | ≦1.70 (0.29) | 4/4 | 2.40 (0.41) | 2.59 (0.26) | 3.32 (0.39) | 3.62 (0.12) | 2.88 (0.33) | 2.57 (0.47) |
| 3Ap28F | 6.4 | 4/4 | 3.98 (0.86) | ≦1.40 (0.05) | 4/4 | 2.12 (0.64) | 1.90 (0.44) | 2.73 (0.36) | 3.28 (0.36) | 2.45 (0.16) | ≦1.83 (0.22) |

+GMT = geometric mean titer
*Sera obtained from animals three weeks post-infection.
PRNT is a 60% plaque reduction neutralization test.
EIA-F, Ga, Gb are enzyme immunoassays testing reactivity of sera with purified F protein (from RSV A2), purified Ga (from RSV A2, and purified Gb (from RSV 18537).

TABLE 13

RSV Infection of Seropositive Chimps

| VIRUS | DOSE | DAY | NEUTRALIZATION TITERS[1] (LOG$_{10}$) 2B | 3A | A2 | EIA TITERS[2] (LOG$_{10}$) EIA-F | EIA-Ga | EIA-Gb |
|---|---|---|---|---|---|---|---|---|
| RSV 2B | 4.0 PFU | −1 | 2.0 | 2.1 | 2.0 | 4.1 | 3.6 | 2.9 |
|  |  | 7 | 2.7 | 2.4 | 2.4 | 4.2 | 3.4 | 3.1 |
|  |  | 14 | 5.0 | 5.1 | 5.0 | 6.6 | 5.4 | 5.2 |
|  |  | 21 | 4.9 | 5.0 | 4.9 | 6.5 | 5.3 | 5.2 |
|  |  | D21/D-1* | 2.9 | 2.9 | 2.9 | 2.4 | 1.7 | 2.3 |
| RSV2B | 5.0 PFU | −1 | 2.4 | 2.8 | 2.8 | 4.6 | 4.3 | 3.5 |
|  |  | 7 | 2.9 | 3.2 | 3.0 | 4.9 | 4.3 | 3.5 |
|  |  | 14 | 5.0 | 5.1 | >5.1 | 6.5 | 5.5 | 4.7 |
|  |  | 21 | 4.8 | 5.4 | 4.9 | 6.4 | 5.8 | 5.3 |
|  |  | D21/D-1 | 2.4 | 2.6 | 2.1 | 1.8 | 1.5 | 1.8 |
| RSV 2Bp20L | 4.0 PFU | −1 | 2.1 | 2.7 | 2.1 | 4.2 | 3.7 | 2.7 |
|  |  | 7 | 2.2 | 2.4 | 2.0 | 4.2 | 3.8 | 2.6 |
|  |  | 14 | 2.0 | 2.4 | 1.9 | 4.1 | 3.8 | 2.6 |
|  |  | 21 | 2.2 | 2.8 | 2.4 | 4.1 | 3.7 | 2.8 |
|  |  | D21/D-1 | 0.1 | 0.1 | 0.3 | −0.1 | 0.0 | 0.1 |
| RSV 2Bp20L | 5.0 PFU | −1 | 1.8 | 2.6 | 2.3 | 3.8 | 4.0 | 3.0 |
|  |  | 7 | 1.8 | 2.2 | 2.2 | 3.7 | 3.9 | 2.8 |
|  |  | 14 | 2.2 | 2.5 | 1.9 | 3.8 | 3.9 | 2.7 |
|  |  | 21 | 2.4 | 2.5 | 2.1 | 3.9 | 4.0 | 3.0 |
|  |  | D21/D-1 | 0.6 | −0.1 | −0.2 | 0.1 | 0.0 | 0.0 |

[1] = 60% plaque reduction neutralization assay performed against RSV strain 2B, 3A, + A2.
[2] = Enzyme immunoassay testing testing reactivity purified RSV.
Source of protein = F (RSV A2), GA (RSV A2), Gb (RSV 18537).
* = Rise in titer day −1 to day 21.

TABLE 14

GROWTH, IMMUNOGENICITY, AND EFFICACY OF RSV 2B TS MUTANTS IN COTTON RATS[1]

| VIRUS | DOSE | #RSV(+) | VIRUS TITER (log$_{10}$ PFU/gm) NASAL | LUNG | IMMUNOGENICITY NEUTRALIZATION[1] A2 | 3A | 2B | EIA-F[2] | CHALLENGE VIRUS TITER (log$_{10}$ PFU/gm) #RSV(+) | NOSE | LUNG |
|---|---|---|---|---|---|---|---|---|---|---|---|
| 2B | 6.1 | 4/4 | ≦3.1 | 4.6 | 174 | 502 | 521 | 1,911 | 1/3 | ≦2.0 | ≦1.8 |
| 2Bp33F | 5.8 | 2/4 | ≦1.2 | <1.1 | 35 | 115 | 145 | 1,041 | 1/4 | <1.8 | ≦1.8 |
| 2Bp24G | 6.4 | 2/4 | ≦1.3 | ≦1.0 | 92 | 201 | 377 | 2,432 | 0/4 | <1.7 | <1.4 |
| 2Bp20L | 6.2 | 0/4 | <1.3 | <1.0 | 41 | 123 | 75 | 482 | 3/4 | ≦2.6 | 3.1 |
| 2BP34L | 5.2 | 0/4 | <1.3 | <1.1 | <10 | <10 | <10 | ≦77 | 4/4 | 4.8 | 5.4 |
| PBS |  |  |  |  | <10 | <10 | <10 | <50 | 4/4 | 4.9 | 5.5 |

[1] = Cotton rats were inoculated with virus by intranasal route. Four days post-infection, lungs and nasal turbinates were harvested for virus titrations. Six weeks post-infection, blood was taken for neutralization and EIA titrations and rats were challenged intranasally with 10$^6$ PFU of RSV 18537. Lungs and nasal turbinates were harvested 4 days post-challenge. Virus and antibody titers are reported as geometric mean titers.
[2] = 60% plaque reduction neutralization test.
[3] = Source of coating protein is RSV A2 F protein.

TABLE 15

GROWTH, IMMUNOGENICITY, AND EFFICACY OF RSV 3A TS MUTANTS IN COTTON RATS[1]

| VIRUS | DOSE | #RSV(+) | VIRUS TITER (log$_{10}$ PFU/gm) NASAL | LUNG | IMMUNOGENICITY NEUTRALIZATION[1] A2 | 3A | 2B | EIA-F[2] | CHALLENGE VIRUS TITER (log$_{10}$ PFU/gm) #RSV(+) | NOSE | LUNG |
|---|---|---|---|---|---|---|---|---|---|---|---|
| 3A | 6.0 | 4/4 | 3.2 | <4.1 | 35 | 141 | 35 | 1,202 | 0/3 | <1.6 | <1.4 |
| 3Ap20E | 6.0 | 4/4 | ≦3.2 | ≦1.4 | ≦17 | 85 | 66 | 646 | 0/4 | <1.6 | <1.3 |
| 3Ap20F | 6.0 | 4/4 | 3.7 | <1.3 | ≦23 | 87 | 55 | 708 | 0/4 | <1.8 | <1.2 |

TABLE 15-continued

GROWTH, IMMUNOGENICITY, AND EFFICACY OF RSV 3A TS MUTANTS IN COTTON RATS[1]

| | | | VIRUS TITER | | IMMUNOGENICITY | | | | CHALLENGE VIRUS TITER | | |
| | | | ($\log_{10}$ PFU/gm) | | NEUTRALIZATION[1] | | | | ($\log_{10}$ PFU/gm) | | |
| VIRUS | DOSE | #RSV(+) | NASAL | LUNG | A2 | 3A | 2B | EIA-F[2] | #RSV(+) | NOSE | LUNG |
|---|---|---|---|---|---|---|---|---|---|---|---|
| 3Ap28F | 6.0 | 3/4 | ≦2.3 | <1.4 | 47 | 282 | 123 | 2,188 | 0/4 | <1.6 | <1.4 |
| PBS | | | | | <10 | <10 | <10 | <50 | 4/4 | 5.6 | 5.6 |

[1] = Cotton rats were inoculated with virus by intranasal route. Four days post-infection, lungs and nasal turbinates were harvested for virus titrations. Six weeks post-infection, blood was taken for neutralization and EIA titrations and rats were challenged intranasally with $10^6$ PFU of RSV A2. Lungs and nasal turbinates were harvested 4 days post-challenge. Virus and antibody titers are reported as geometric mean titers.
[2] = 60% plaque reduction neutralization test.
[3] = Source of coating protein is RSV A2 F protein.

TABLE 16

RSV GROWTH AND IMMUNOGENICITY IN AFRICAN GREEN MONKEYS: RSV 2B TS MUTANTS[1]

| | | TS MUTANT VIRUS GROWTH | | IMMUNOGENICITY | | | | |
| | | PEAK VIRUS TITER (log10 PFU/ml) | | | NEUTRALIZATION TITERS[2] | | | EIA TITERS[3] (×10³) |
| VIRUS | AGM | NASAL | LUNG | DAY | 2B | A2 | 3A | anti-F |
|---|---|---|---|---|---|---|---|---|
| 2Bp33F | SK034 | <0.7 | <0.7 | 0 | <10 | <10 | <10 | <0.15 |
| | | | | 7 | <10 | <10 | <10 | <0.15 |
| | | | | 14 | <10 | <10 | <10 | 0.88 |
| | | | | 24 | <10 | <10 | <10 | 0.49 |
| | | | | 27 | <10 | <10 | <10 | 0.92 |
| | | | | 41 | <10 | <10 | <10 | 0.26 |
| 2Bp33F | SK028 | 2.9 | <0.7 | 0 | <10 | <10 | <10 | <0.15 |
| | | | | 7 | <10 | <10 | <10 | <0.15 |
| | | | | 14 | <10 | <10 | <10 | <0.15 |
| | | | | 24 | 28 | <10 | <10 | 2.92 |
| | | | | 27 | 33 | <10 | <10 | 3.56 |
| | | | | 41 | 19 | <10 | 11 | 1.74 |
| 2Bp24G | SK012 | <0.7 | 1.9 | 0 | <10 | <10 | <10 | <0.15 |
| | | | | 7 | <10 | <10 | <10 | <0.15 |
| | | | | 14 | <10 | <10 | <10 | <0.15 |
| | | | | 24 | 12 | <10 | <10 | 14.91 |
| | | | | 27 | 10 | <10 | <10 | 13.18 |
| | | | | 41 | <10 | <10 | <10 | 11.05 |
| 2Bp24G | SK030 | 3.2 | <0.7 | 0 | <10 | <10 | <10 | <0.15 |
| | | | | 7 | <10 | <10 | <10 | <0.15 |
| | | | | 14 | <10 | <10 | <10 | <0.15 |
| | | | | 24 | 440 | 10 | 204 | 34.13 |
| | | | | 27 | 404 | 21 | 190 | 37.64 |
| | | | | 41 | 256 | <10 | 98 | 17.74 |
| 2Bp20L | SK033 | <0.7 | <0.7 | 0 | <10 | <10 | <10 | 0.24 |
| | | | | 7 | <10 | <10 | <10 | 0.30 |
| | | | | 14 | <10 | <10 | <10 | 1.48 |
| | | | | 24 | <10 | <10 | <10 | 1.64 |
| | | | | 27 | <10 | <10 | <10 | 1.24 |
| | | | | 41 | <10 | <10 | <10 | 0.34 |
| 2Bp20L | SK042 | <0.7 | <0.7 | 0 | <10 | <10 | <10 | <0.15 |
| | | | | 7 | <10 | <10 | <10 | <0.15 |
| | | | | 14 | <10 | <10 | <10 | <0.15 |
| | | | | 24 | <10 | <10 | <10 | 0.18 |
| | | | | 27 | <10 | <10 | <10 | 0.20 |
| | | | | 41 | <10 | <10 | <10 | 0.15 |

[1] = All monkeys were inoculated with $10^6$ PFU of RSV 2B TS virus, IN + IT.
[2] = 60% plaque reduction neutralization test.
[3] = Source of coating protein is RSV A2 F protein.

TABLE 17

RSV GROWTH AND IMMUNOGENICITY IN AFRICAN GREEN MONKEYS: RSV 2B CHALLENGE OF MONKEYS 8 WEEKS POST-VACCINATED WITH RSV 2B TS MUTANTS[1]

| VACCINE VIRUS | AGM | CHALLENGE VIRUS GROWTH PEAK VIRUS TITER (log10 PFU/ml) NASAL | LUNG | DAY | IMMUNOGENICITY NEUTRALIZATION TITERS[2] 2B | A2 | 3A | EIA TITERS[3] (×10³) anti-F |
|---|---|---|---|---|---|---|---|---|
| 2Bp33F | SK034 | 5.7 | 5.0 | 0 | <10 | <10 | <10 | 0.52 |
| | | | | 7 | <10 | <10 | <10 | 0.91 |
| | | | | 14 | 451 | 10 | 472 | 303.84 |
| | | | | 21 | 6797 | 33 | 829 | 592.61 |
| | | | | 28 | 4353 | 50 | 815 | 135.85 |
| | | | | 42 | 1978 | 44 | 264 | 52.76 |
| 2Bp33F | SK028 | <0.8 | 3.8 | 0 | 13 | <10 | <10 | 2.50 |
| | | | | 7 | 208 | 65 | 576 | 43.64 |
| | | | | 14 | 2868 | 443 | 2051 | 131.70 |
| | | | | 21 | 1883 | 404 | 2344 | 144.39 |
| | | | | 28 | 1127 | 227 | 2797 | 53.22 |
| | | | | 42 | 941 | 79 | 729 | 43.30 |
| 2Bp24G | SK012 | 3.9 | 3.2 | 0 | <10 | <10 | <10 | 21.58 |
| | | | | 7 | 281 | 111 | 323 | 258.89 |
| | | | | 14 | 604 | 431 | 731 | 551.49 |
| | | | | 21 | 698 | 298 | 692 | 668.50 |
| | | | | 28 | 357 | 325 | 985 | 189.81 |
| | | | | 42 | 272 | 82 | 895 | 104.16 |
| 2Bp24G | SK030 | <0.8 | <0.7 | 0 | 91 | <10 | 69 | 34.55 |
| | | | | 7 | 628 | 322 | 1120 | 174.07 |
| | | | | 14 | 1617 | 397 | 1953 | 203.58 |
| | | | | 21 | 1184 | 256 | 968 | 145.71 |
| | | | | 28 | 851 | 276 | 1313 | 49.28 |
| | | | | 42 | 637 | 48 | 329 | 27.36 |
| 2Bp20L | SK033 | 5.3 | 4.5 | 0 | <10 | <10 | <10 | 1.78 |
| | | | | 7 | <10 | <10 | <10 | 1.88 |
| | | | | 14 | 516 | <10 | 325 | 289.94 |
| | | | | 21 | 500 | 22 | 550 | 418.91 |
| | | | | 28 | 783 | 56 | 525 | 148.25 |
| | | | | 42 | 518 | 48 | 442 | 91.39 |
| 2Bp20L | SK042 | 5.4 | 3.3 | 0 | <10 | <10 | <10 | 0.21 |
| | | | | 7 | <10 | <10 | <10 | 0.32 |
| | | | | 14 | 36 | <10 | 116 | 135.80 |
| | | | | 21 | 213 | 21 | 284 | 116.99 |
| | | | | 28 | 256 | 30 | 300 | 30.06 |
| | | | | 42 | 516 | 40 | 289 | 19.30 |
| Control | SK046 | 5.9 | 4.7 | 0 | <10 | <10 | <10 | 0.10 |
| | | | | 7 | <10 | <10 | <10 | 0.13 |
| | | | | 14 | 272 | 50 | 594 | 275.33 |
| | | | | 21 | 488 | 98 | 1140 | 587.93 |
| | | | | 28 | 1377 | 75 | 1393 | 190.49 |
| | | | | 42 | 1659 | 47 | 573 | 183.97 |
| Control | 032B | 5.5 | 3.9 | 0 | <10 | <10 | <10 | 0.25 |
| | | | | 7 | <10 | <10 | <10 | 0.24 |
| | | | | 14 | 2462 | 201 | 3458 | 626.57 |
| | | | | 21 | 1546 | 303 | 1279 | 482.31 |
| | | | | 28 | 1162 | 104 | 1729 | 164.53 |
| | | | | 42 | 1044 | 83 | 689 | 75.1 |

[1] = AGMs were previously vaccinated with RSV 2B TS virus strains. All monkeys were challenged 8 weeks post-vaccination with 10⁶ PFU of RSV 2B, IN + IT.
[2] = 60% plaque reduction neutralization test.
[3] = Source of coating protein is RSV A2 F protein.

TABLE 18

RSV GROWTH AND IMMUNOGENICITY IN AFRICAN GREEN MONKEYS: RSV 3A TS MUTANTS[1]

| VIRUS | AGM | VIRUS GROWTH PEAK VIRUS TITER (log10 PFU/ml) | | DAY | IMMUNOGENICITY NEUTRALIZATION TITERS[2] | | | EIA-F TITERS[3] |
|---|---|---|---|---|---|---|---|---|
| | | NASAL | LUNG | | 2B | A2 | 3A | ($\times 10^3$) |
| 3Ap20E | 01128 | 1.7 | 1.3 | 0 | <10 | <10 | <10 | <0.05 |
| | | | | 7 | <10 | <10 | <10 | <0.05 |
| | | | | 14 | <10 | <10 | <10 | 3.72 |
| | | | | 21 | 38 | <10 | 39 | 23.12 |
| | | | | 28 | 21 | <10 | 13 | 27.42 |
| | | | | 40 | 14 | <10 | <10 | 31.11 |
| 3Ap20E | 0L1161 | 2.3 | 2.9 | 0 | <10 | <10 | <10 | <0.05 |
| | | | | 7 | <10 | <10 | <10 | <0.05 |
| | | | | 14 | <10 | <10 | 30 | 5.84 |
| | | | | 21 | 14 | 12 | 57 | 19.51 |
| | | | | 28 | 56 | 18 | 126 | 27.53 |
| | | | | 40 | 44 | 31 | 108 | 38.90 |
| 3Ap20F | 90B037 | 3.2 | <1.0 | 0 | <10 | <10 | <10 | <0.05 |
| | | | | 7 | <10 | <10 | <10 | <0.05 |
| | | | | 14 | <10 | <10 | 11 | 1.17 |
| | | | | 21 | 12 | <10 | 47 | 34.32 |
| | | | | 28 | 20 | 17 | 86 | 31.58 |
| | | | | 40 | 49 | 26 | 123 | 35.05 |
| 3Ap20F | 90B045 | 3.9 | 1.0 | 0 | <10 | <10 | <10 | 0.35 |
| | | | | 7 | <10 | <10 | <10 | 0.30 |
| | | | | 14 | <10 | <10 | 19 | 3.16 |
| | | | | 21 | 11 | 11 | 22 | 12.61 |
| | | | | 28 | 12 | 13 | 24 | 16.82 |
| | | | | 40 | 24 | <10 | 39 | 14.92 |
| 3Ap28F | 91B027 | 2.0 | <0.8 | 0 | <10 | <10 | <10 | <0.05 |
| | | | | 7 | <10 | <10 | <10 | <0.05 |
| | | | | 14 | <10 | <10 | <10 | 0.18 |
| | | | | 21 | <10 | <10 | <10 | 1.29 |
| | | | | 28 | <10 | <10 | <10 | 2.63 |
| | | | | 40 | <10 | <10 | <10 | 3.44 |
| 3Ap28F | 91B043[4] | 2.9 | <0.9 | 0 | <10 | <10 | <10 | <0.05 |
| | | | | 7 | <10 | <10 | <10 | <0.05 |
| | | | | 14 | <10 | 11 | 27 | 3.83 |

[1] = All monkeys were inoculated with $10^6$ PFU of RSV 3A TS viruses, IN + IT.
[2] = 60% plaque reduction neutralization test.
[3] = Source of coating protein is RSV A2 F protein.
[4] = Monkey died on day 15. Cause of death unrelated to RSV infection.

TABLE 19

RSV GROWTH AND IMMUNOGENICITY IN AFRICAN GREEN MONKEYS: RSV 3A CHALLENGE OF MONKEYS 8 WEEKS POST- VACCINATED WITH RSV 3A TS MUTANTS[1]

| VACCINE VIRUS | AGM | CHALLENGE VIRUS GROWTH PEAK VIRUS TITER (log10 PFU/ml) | | DAY | IMMUNOGENICITY NEUTRALIZATION TITERS[2] | | | EIA-F TITERS[3] |
|---|---|---|---|---|---|---|---|---|
| | | NASAL | LUNG | | 2B | A2 | 3A | ($\times 10^3$) |
| 3Ap20E | 01128 | 1.4 | 0.7 | 0 | 14 | 12 | <10 | 35.75 |
| | | | | 7 | 216 | 281 | 602 | 699.10 |
| | | | | 14 | 417 | 265 | 784 | 611.24 |
| | | | | 21 | 289 | 307 | 573 | 247.16 |
| | | | | 28 | 263 | 289 | 731 | 463.57 |
| | | | | 42 | 145 | 141 | 426 | 285.47 |
| 3Ap20E | 0L1161 | 2.2 | <0.8 | 0 | 21 | <10 | 56 | 25.37 |
| | | | | 7 | 526 | 412 | 2735 | 535.05 |
| | | | | 14 | 516 | 521 | 2382 | 252.93 |
| | | | | 21 | 581 | 473 | 1840 | 275.32 |
| | | | | 28 | 478 | 437 | 1651 | 244.01 |
| | | | | 42 | 250 | 239 | 753 | 141.33 |
| 3Ap20F | 90B03 | <1.1 | <0.8 | 0 | 84 | 56 | 221 | 41.17 |
| | | | | 7 | 2374 | 2093 | 6051 | 435.25 |
| | | | | 14 | 3701 | 2916 | 8652 | 450.55 |

TABLE 19-continued

RSV GROWTH AND IMMUNOGENICITY IN AFRICAN GREEN MONKEYS: RSV 3A
CHALLENGE OF MONKEYS 8 WEEKS POST- VACCINATED WITH RSV 3A TS MUTANTS[1]

| VACCINE VIRUS | AGM | CHALLENGE VIRUS GROWTH PEAK VIRUS TITER (log10 PFU/ml) | | DAY | IMMUNOGENICITY | | | |
|---|---|---|---|---|---|---|---|---|
| | | | | | NEUTRALIZATION TITERS[2] | | | EIA-F TITERS[3] |
| | | NASAL | LUNG | | 2B | A2 | 3A | (×10³) |
| 3Ap20F | 90B045 | <1.0 | <0.8 | 21 | 2933 | 2224 | 6561 | 481.99 |
| | | | | 28 | 1849 | 1588 | 4031 | 287.28 |
| | | | | 42 | 3086 | 967 | 3950 | 207.98 |
| | | | | 0 | 24 | 12 | 56 | 13.44 |
| | | | | 7 | 644 | 627 | 1381 | 182.99 |
| | | | | 14 | 1024 | 549 | 2174 | 223.70 |
| | | | | 21 | 1835 | 699 | 2130 | 273.87 |
| | | | | 28 | 831 | 318 | 1499 | 177.21 |
| | | | | 42 | 534 | 258 | 1073 | 127.80 |
| 3Ap28F | 91B027 | <1.0 | 0.8 | 0 | <10 | <10 | <10 | 5.50 |
| | | | | 7 | 408 | 229 | 521 | 150.97 |
| | | | | 14 | 585 | 560 | 2016 | 234.25 |
| | | | | 21 | 449 | 311 | 1161 | 359.53 |
| | | | | 28 | 316 | 400 | 714 | 184.91 |
| | | | | 42 | 242 | 217 | 436 | 142.67 |
| Control | 91K041 | 5.0 | 4.7 | 0 | <10 | <10 | <10 | <0.05 |
| | | | | 7 | <10 | <10 | <10 | 0.13 |
| | | | | 14 | 19 | <10 | 205 | 213.29 |
| | | | | 21 | 106 | 33 | 423 | 602.54 |
| | | | | 28 | 123 | 99 | 278 | 562.05 |
| | | | | 42 | 107 | 80 | 277 | 252.99 |
| Control | 91K059 | 5.1 | 4.6 | 0 | <10 | <10 | <10 | <0.05 |
| | | | | 7 | <10 | <10 | <10 | 0.09 |
| | | | | 14 | 97 | 34 | 384 | 166.59 |
| | | | | 21 | 288 | 158 | 1259 | 268.47 |
| | | | | 28 | <160 | <160 | 575 | 286.52 |
| | | | | 42 | 290 | 178 | 1448 | 218.74 |

[1] = AGMs were previously vaccinated with RSV 3A TS virus strains. All monkeys were challenged 8 weeks post-vaccination with 10⁶ PFU of RSV 3A, IN + IT.
[2] = 60% plaque reduction neutralization test.
[3] = Source of coating protein is RAV A2 F protein.

TABLE 20

GROWTH, IMMUNOGENICITY, AND EFFICACY OF RSV TS-1 COTTON RATS[1]

| VIRUS | DOSE | #RSV(+) | VIRUS TITER (log₁₀ PFU/gm) | | IMMUNOGENICITY | | | | CHALLENGE VIRUS TITER | | |
|---|---|---|---|---|---|---|---|---|---|---|---|
| | | | | | NEUTRALIZATION[1] | | | | | (log₁₀ PFU/gm) | |
| | | | NASAL | LUNG | A2 | 3A | 2B | EIA-F[2] | #RSV(+) | NOSE | LUNG |
| A2 | 5.5 | 4/4 | 3.6 | 4.0 | 234 | 367 | 188 | 1,259 | 0/4 | <1.8 | <1.3 |
| TS-1 | 5.9 | 4/4 | <2.7 | 2.3 | 100 | 385 | 181 | 2,071 | 0/3 | <1.9 | <1.3 |
| PBS | | | | | <10 | <10 | <10 | <50 | 4/4 | 4.5 | 4.8 |

[1] = Cotton rats were inoculated with virus by intranasal route. Four days post-infection, lungs and nasal turbinates were harvested for virus titrations. Six weeks post-infection, blood was taken for neutralization and EIA titrations and rats were challenged intranasally with 10⁶ PFU of RSV A2. Lungs and nasal turbinates were harvested 4 days post-challenge. Virus and antibody titers are reported as geometric mean titers.
[2] = 60% plaque reduction neutralization test.
[3] = Source of coating protein is RSV A2 F protein.

REFERENCES

Anderson J J, Norden J, Saunders D, Toms G L, Scott R (1990): Analysis of the local and systemic immune responses induced in BALB/c mice by experimental respiratory syncytial virus infection. Journal of General Virology 71:1561–1570.

Anderson L J, Hierholzer J C, Tsou C, Hendry R M, Fernie B F, Stone Y, McIntosh K (1985): Antigenic characterization of respiratory syncytial virus strains with monoclonal antibodies. Journal of Infectious Diseases 151:626–633.

Anderson L J, Hendry R M, Pierik L T, Tsou C, McIntosh K (1991): Multicenter study of strains of respiratory syncytial virus. Journal of Infectious Diseases 163:687–692.

Akerlind B, Norrby E, Orvell C, Mufson M A (1988): Respiratory syncytial virus: Heterogeneity of subgroup B strains. Journal of General Virology 69:2145–2154.

Beeler J A, Coelingh K W (1989): Neutralization epitopes of the F glycoprotein of respiratory syncytial virus: Effect of mutation upon fusion function. Journal of Virology 63:2941–2950.

Belshe R B, Hissom F K (1982): Cold adaptation of parainfluenza virus type 3: Induction of three phenotypic markers. Journal of Medical Virology 10:235–242.

Belshe R B, Van Voris L P, Mufson M A (1982): Parenteral administration of live respiratory syncytial virus vaccine: Results of a field trial. Journal of Infectious Diseases 145:311–319.

Brideau R J, Walters R R, Stier M A, Wathen M W (1989): Protection of cotton rats against human respiratory syncytial virus by vaccination with a novel chimeric FG glycoprotein. Journal of General Virology 70:2637–2644.

Burke K L, Dunn G, Ferguson M, Minor P D, Almond J W (1988): Antigen chimaeras of poliovirus as potential new vaccines. Nature 332:81–82.

Burke K L, Evans D J, Jenkins O, Meredith J, D'Souza E D A, Almond J W (1989): A cassette vector for the construction of antigen chimaeras of poliovirus. Journal of General Virology 70:2474–2479.

Chakrabarti et al. (1985): Mol. Cell Biol. 5:3403–3409.

Chin J, Magoffin R L, Shearer L A, Schieble J H, Lennette E H (1969): Field evaluation of a respiratory syncytial virus vaccine and a trivalent parainfluenza virus vaccine in a pediatric population. American Journal of Epidemiology 89:449–463.

Clements M L, Belshe R B, King J, Newman F, Westblom T U, Tierney E L, London W T, Murphy B R (1991): Evaluation of Bovine, cold-adapted human, and wild-type human parainfluenza type 3 viruses in adult volunteers and in chimpanzees. Journal of Clinical Microbiology 29:1175–1182.

Collins, P L (1991): The molecular biology of human respiratory syncytial virus (RSV) of the genus Pneumovirus. In Kingsbury D W (ed): "The Paramyxoviruses". Plenum Publishing Corporation, pp103–162.

Collins P L, Prince G A, Camargo E, Purcell R H, Chanock R M, Murphy B R, Davis A R, Lubeck M D, Mizutani S, Hung P P (1990): Evaluation of the protective efficacy of recombinant vaccinia viruses and adenoviruses that express respiratory syncytial virus glycoproteins. In "Vaccines 90", Cold Spring Harbor Laboratory Press, pp79–84.

Collins P L, Purcell R H, London W T, Lawrence L A, Chanock R M, Murphy B R (1990): Evaluation in chimpanzees of vaccinia virus recombinants that express the surface glycoproteins of human respiratory syncytial virus. Vaccine 8:164–168.

Collins P L, Mink M A, Stec D S (1991): Rescue of synthetic analogs of respiratory syncytial virus genomic RNA and effect of truncations and mutations on the expression of a foreign reporter gene. Proceedings of the National Academy of Science USA 88:9663–9667.

Connors M, Collins P L, Firestone C Y, Murphy B R (1991): Respiratory syncytial virus (RSV) F, G, M2 (22K), and N proteins each induce resistance to RSV challenge, but resistance induced by M2 and N proteins is relatively short-lived. Journal of Virology 65:1634–1637.

Duffy, J I, Vaccine Preparation Techniques, Noyes Data Corporation (1980).

Edwards K M, King J C, Steinhoff M C, Thompson J, Clements M L, Wright P F, Murphy B R (1991): Safety and immunogenicity of live attenuated cold-adapted influenza B/Ann Arbor/1/86 reassortant virus vaccine in infants and children. Journal of Infectious Diseases 163:740–745.

Forsyth B R, Phillips C A (1973): Laboratory and antigenic studies of respiratory syncytial virus; evaluation of respiratory syncytial, meningococcal, and pneumococcal polysaccharide vaccines. NIH contract report number IDB-VDP-07-067.

Frickey P H (1969): Markers differentiating a "cold" variant of respiratory syncytial virus from its parent line. Internal report—Lederle Laboratories.

Friedewald W T, Forsyth B R, Smith C B, Gharpure M A, Chanock RM (1968): Low-temperature-grown RS virus in adult volunteers. Journal of the American Medical Association 204:690–694.

Fulginiti V A, Eller J J, Sieber O F, Joyner J W, Minamitani M, Meiklejohn G (1969): I. A field trial of two inactivated respiratory virus vaccines; an aqueous trivalent parainfluenza virus vaccine and an alum-precipitated respiratory syncytial virus vaccine. American Journal of Epidemiology 89:435–448.

Gharpure M A, Wright P F, Chanock R M (1969): Temperature-sensitive mutants of respiratory syncytial virus. Journal of Virology 3:414–421.

Glezen W P, Paredes A, Allison J E, Taber L H, Frank A L (1981): Risk of respiratory syncytial virus infection for infants from low-income families in relationship to age, sex, ethnic group, and maternal antibody level. Journal of Pediatrics 98:706–715.

Glezen W P, Taber L H, Frank A L, Kasel J A (1986): Risk of primary infection and reinfection with respiratory syncytial virus. American Journal of Diseases of Children 140:543–546.

Graham B S, Bunton L A, Wright P F, Karzon D T (1991): Role of T lymphocyte subsets in the pathogenesis of primary infection and rechallenge with respiratory syncytial virus in mice. Journal of Clinical Investigation 88:1026–1033.

Grunstein, M. and Hogness, D. (1975): A method for isolation of cloned DNAs that contain a specific gene. Proceedings of the National Academy of Sciences 72:3961–3965.

Hall C B, McBride J T (1991): Respiratory syncytial virus—from chimps with colds to conundrums and cures. New England Journal of Medicine 325:57–58.

Hall C B, Walsh E E, Long C E, Schnabel K C (1991): Immunity to and frequency of reinfection with respiratory syncytial virus. Journal of Infectious Diseases 163:693–698.

Henderson F W, Collier A M, Clyde W A, Denny F W (1979): Respiratory-syncytial-virus infections, reinfections and immunity; A prospective, longitudinal study in young children. New England Journal of Medicine 300:530–534.

Hodes D S, Kim H W, Parrott R H, Camargo E, Chanock R M (1974): Genetic alteration in a temperature-sensitive mutant of respiratory syncytial virus after replication in vivo (37972). Proceedings of the Society for Experimental Biology and Medicine 145:1158–1164.

Holland J, Spindler K, Horodyski F, Grabau E, Nichol S, Vandepol S (1982): Rapid evolution of RNA genomes. Science 215:1577–1585.

Huang, Y. and Wertz, G. (1982): The genome of respiratory syncytial virus is a negative-stranded RNA that codes for at least seven mRNA species. Journal of Virology 42:150–157.

Institute of Medicine, Committee on Issues and Priorities for New Vaccine Development (1985): Prospects for immunizing against respiratory syncytial virus. In "New vaccine development: establishing priorities, Vol: diseases of importance in the United States". Washington, D.C.: National Academy Press, pp 397–409.

Johnson P R, Olmsted R A, Prince G A, Murphy B R, Alling D W, Walsh E E, Collins P L (1987): Antigenic relatedness between glycoproteins of human respiratory syncytial virus subgroups A and B: Evaluation of the contributions of F and G glycoproteins to immunity. Journal of Virology 61: 3163–3166.

Kapikian A Z, Mitchell R H, Chanock R M, Shvedoff R A, Stewart C E (1968): An epidemiologic study of altered clinical reactivity to respiratory syncytial (RS) virus infection in children previously vaccinated with an inactivated RS virus vaccine. American Journal of Epidemiology 89:405–421

Kasel J A, Walsh E E, Frank A L, Baxter B D, Taber L H, Glezen W P (1987/1988): Relation of serum antibody to glycoproteins of respiratory syncytial virus with immunity to infection in children. Viral Immunology 1:199–205.

Kim H W, Canchola J G, Brandt C D, Pyles G, Chanock R M, Jensen K, Parrott R H (1969): Respiratory syncytial virus disease in infants despite prior administration of antigenic inactivated vaccine. American Journal of Epidemiology 89:422–434.

Kim H W, Arrobio J O, Pyles G, Brandt C D, Camargo E, Chanock R M, Parrott R H (1971): Clinical and immunological response of infants and children to administration of low-temperature adapted respiratory syncytial virus. Pediatrics 48:745–755.

Kim H W, Arrobio J O, Brandt C D, Wright P, Hodes D, Chanock R M, Parrott R H (1973): Safety and antigenicity of temperature sensitive (TS) mutant respiratory syncytial virus (RSV) in infants and children. Pediatrics 52:56–63.

Kim H W, Leikin S L, Arrobio J, Brandt C D, Chanock R M, Parrott R H (1976): Cell-mediated immunity to respiratory syncytial virus induced by inactivated vaccine or by infection. Pediatric Research 10:75–78.

Lamprecht C L, Krause H E, Mufson M A (1976): Role of maternal antibody in pneumonia and bronchiolitis due to respiratory syncytial virus. Journal of Infectious Diseases 134:211–217.

Maassab H F, DeBorde D C (1985): Development and characterization of cold-adapted viruses for use as live virus vaccines. Vaccine 3:355–369.

Maassab H F, Heilman C A, Herlocher M L (1990): Cold-adapted influenza viruses for use as live vaccines for man, In "Viral Vaccines" Wiley-Liss, Inc.

MacKett (1984): J. Virol. 49:857–864.

Maxam, A M. Gilbert, W. (1977): A new method for sequencing DNA. Proceedings of the National Academy of Sciences 74:560.

Maxam A M, Gilbert W (1980): Sequencing end-labeled DNA with base-specific chemical cleavages. Methods in Enzymology 65:499–560.

McIntosh K, Arbeter A M, Stahl N K, Orr I A, Hodes D S, Ellis E F (1974): Attenuated respiratory syncytial virus vaccines in asthmatic children. Pediatric Research 8:689–696.

McIntosh K, Chanock R M (1990): Respiratory Syncytial Virus. In Fields B N, Knipe D M (eds):"Virology" New York: Raven Press, Ltd, pp1045–1072.

McKay E, Higgins P, Tyrell D, Pringle C (1988): Immunogenicity and pathogenicity of temperature-sensitive modified respiratory syncytial virus in adult volunteers. Journal of Medical Virology 25:411–421.

Mufson M A, Orvell C, Rafnar B, Norrby E (1985): Two distinct subtypes of human respiratory syncytial virus. Journal of General Virology 66:2111–2124.

Mufson M A, Belshe R B, Orvell C, Norrby E (1987): Subgroup characteristics of respiratory syncytial virus strains recovered form children with two consecutive infections. Journal of Clinical Microbiology 25:1535–1539.

Murphy B R, Walsh E E (1988): Formalin-inactivated respiratory syncytial virus vaccine induces antibodies to the fusion glycoprotein that are deficient in fusion-inhibiting activity. Journal of Clinical Microbiology 26:1595–1597.

Murphy B R, Tierney E L, London W T, Belshe R B (1990): A cold-adapted mutant of human parainfluenza virus type 3 is attenuated and protective in chimpanzees. In "Vaccines 90" Cold Spring Harbor Laboratory Press pp 91–95.

Nicholas J A, Rubino K L, Levely M E, Adams E G, Collins P L (1990): Cytolytic T-lymphocyte responses to respiratory syncytial virus: Effector cell phenotype and target proteins. Journal of Virology 64:4232–4241.

Obrosova-Serova N P, Slepushkin A N, Kendal A P, Harmon M W, Burtseva E I, Bebesheva N I, Beljaev A L, Lonskaja N I, Medvedva T E, Egorov A Y, Peklisove L V, Alexandrova G I (1990): Evaluation in children of cold-adapted influenza B live attenuated intranasal vaccine prepared by reassortment between wild-type B/Ann Arbor/1/86 and cold-adapted B/Leningrad/14/55 viruses. Vaccine 8:57–60.

Olmsted R A, Buller R M L, Collins P L, London W T, Beeler J A, Prince G A, Chanock R M, Murphy B R (1988): Evaluation in non-human primates of the safety, immunogenicity and efficacy of recombinant vaccinia viruses expressing the F or G glycoprotein of respiratory syncytial virus. Vaccine 6:519–524.

Oppenshaw P J M, Anderson K, Wertz G W, Askonas B A (1990): The 22,000-kilodalton protein of respiratory syncytial virus is a major target for $K^d$-restricted cytotoxic T lymphocytes from mice primed by infection. Journal of Virology 64:1683–1689.

Prince G A, Jenson A B, Hemming V G, Murphy B R, Walsh E E, Horswood R L, Chanock R M (1986): Enhancement of respiratory syncytial virus pulmonary pathology in cotton rats by prior intramuscular inoculation of formalin-inactivated virus. Journal of Virology 57:721–728.

Richardson L S, Belshe R B, London W T, Sly D L, Prevar D A, Camargo E, Chanock R M (1978): Evaluation of five temperature-sensitive mutants of respiratory syncytial virus in primates: I. Viral shedding, immunologic response, and associated illness. Journal of Medical Virology 3:91–100.

Roberts and Lauer (1979): Methods in Enzymology 68:473.

Rose C S P, Evans D J (1991): Poliovirus antigen chimeras. Trends in Biotechnology 9:415–421.

Sanger, F. Nicklen S, Coulson A R (1977): DNA Sequencing with chain-terminating inhibitors. P.N.AS. 74:5463–5467.

Sanger, F. (1977): National Acadamy Science 74:5463–5467.sequencing with chaim-terminating inhibitors. Proceedings of the National Academy of Sciences 74:5463–5467

Stott E J, Taylor G, Ball L A, Anderson K, Young K K Y, King A M Q, Wertz G W (1987): Immune and histopathological responses in animals vaccinated with recombinant vaccinia viruses that express individual genes of human respiratory syncytial virus. Journal of Virology 61:3855–3861.

Sullender W M, Mufson M A, Anderson L J, Wertz G W (1991): Genetic diversity of the attachment protein of subgroup B respiratory syncytial viruses. Journal of Virology 65:5425–5434.

Sun C S, Wyde P R, Knight V (1983): Correlation of cytotoxic activity in lungs to recovery of normal and gamma-irradiated cotton rats from respiratory syncytial virus infection. American Review of Respiratory Diseases 128:668–672.

Trudel M, Nadon F, Seguin C, Binz H (1991): Protection of BALB/c mice from respiratory syncytial virus infection by immunization with a synthetic peptide derived from the G glycoprotein. Virology 185:749–757.

Trudel M, Stott E J, Taylor G, Oth D, Mercier F, Nadon F, Seguin C, Simard C, Lacroix M (1991): Synthetic peptides corresponding to the F protein of RSV stimulate murine B and T cells but fail to confer protection. Archives of Virology 117:59–71.

Wair, G W, "Preparation of Antigens and Principles of Immunization", in J J Marchalonis and G W Warr, eds., *Antibody as Tool—The Applications of Immunochemistry*, pp 21–58, John Wiley & Sons (1982).

Walsh E E, Hall C B, Briselli M, Brandriss M W, Schlesinger J J (1987): Immunization with glycoprotein subunits of respiratory syncytial virus to protect cotton rats against viral infection. Journal of Infectious Diseases 155:1198–1204.

Wathen M W, Kakuk T J, Brideau R J, Hausknecht E C, Cole S L, Zaya R M (1991): Vaccination of cotton rats with a chimeric FG glycoprotein of human respiratory syncytial virus induces minimal pulmonary pathology on challenge. Journal of Infectious Diseases 163:477–482.

Watt P J, Robinson B S, Pringle C R, Tyrell D A J (1990): Determinants of susceptibility to challenge and the antibody response of adult volunteers given experimental respiratory syncytial virus vaccines. Vaccine 8:231–236.

Wright P F, Woodend W G, Chanock R M (1970): Temperature-sensitive mutants of respiratory syncytial virus: In-vivo studies in hamsters. Journal of Infectious Diseases 122:501–512.

Wright P F, Shinozaki T, Fleet W, Sell S H, Thompson J, Karzon D T (1976): Evaluation of a live, attenuated respiratory syncytial virus vaccine in infants. Journal of Pediatrics 88:931–936.

Wright P F, Belshe R B, Kim H W, Van Voris L P, Chanock R M (1982): Administration of a highly attenuated, live respiratory syncytial virus vaccine to adults and children. Infection and Immunity 37:397–400.

What is claimed is:

1. A cold adapted mutant respiratory syncytial virus which is more attenuated in African green monkeys than the TS-1 respiratory syncytial virus mutant, wherein the mutant is derived from 3A strain of respiratory syncytial virus.

2. A pharmaceutical composition comprising a cold adapted mutaril respiratory syncytial virus which is more attenuated in African monkeys than the TS-1 respiratory syncytial virus mutant, and a pharmaceutically acceptable carrier, wherein the mutant is derived from 3A strain of respiratory syncytial virus.

3. A pharmaceutical composition of claim 2, wherein the mutant respiratory syncytial virus is selected from the group consisting of ATCC designations VR 2369 and VR 2367.

4. A method of vaccinating against respiratory syncytial viral infection in a subject mammal comprising administering to the subject mammal an effective immunizing amount of a pharmaceutical composition comprising a cold adapted mutant respiratory syncytial virus which is more attenuated in African monkeys than the TS-1 respiratory syncytial virus mutant, and a pharmaceutically acceptable carrier, wherein the mutant is derived from 3A strain of respiratory syncytial virus.

5. A method of claim 4, wherein the mutant respiratory syncytial virus is selected from the group consisting of ATCC designations VR 2369 and VR2367.

6. A cold adapted mutant respiratory syncytial virus which is more attenuated in African green monkeys than the TS-1 respiratory syncytial virus mutant, wherein the mutant is derived from 2B strain of respiratory syncytial virus.

7. A pharmaceutical composition comprising a cold adapted mutant respiratory syncytial virus which is more attenuated in African green monkeys than the TS-1 respiratory syncytial virus mutant, and a pharmaceutically acceptable carrier, wherein the mutant is derived from 2B strain of respiratory syncytial virus.

8. A pharmaceutical composition of claim 7, wherein the mutant virus is selected from the group consisting of ATCC designations VR 2364, VR 2370 and VR 2368.

9. A method of vaccinating against respiratory syncytial viral infection in a subject mammal comprising administering to the subject mammal an effective immunizing amount of a pharmaceutical composition comprising a cold adapted mutant respiratory syncytial virus which is more attenuated in African monkeys than the TS-1 respiratory syncytial virus mutant, and a pharmaceutically acceptable carrier, wherein the mutant is derived from 2B strain of respiratory syncytial virus.

10. A method of claim 9, wherein the mutant virus is selected from the group consisting of ATCC designations VR 2364, VR 2370 and VR 2368.

11. Cold adapted mutant respiratory syncytial virus having the ATCC designation VR2369.

12. Cold adapted mutant respiratory syncytial virus having the ATCC designation VR2367.

13. Cold adapted mutant respiratory syncytial virus having the ATCC designation VR2364.

14. Cold adapted mutant respiratory syncytial virus having the ATCC designation VR2370.

15. Cold adapted mutant respiratory syncytial virus having the ATCC designation VR2368.

* * * * *

UNITED STATES PATENT AND TRADEMARK OFFICE
CERTIFICATE OF CORRECTION

PATENT NO. : 5,932,222
DATED : August 3, 1999
INVENTOR(S) : Valerie B. Randolph

It is certified that error appears in the above-identified patent and that said Letters Patent is hereby corrected as shown below:

Title page, item [75] please delete Joan C. Crowley as inventor.

In claim 2, column 53, line 42 "mutaril" should be ---mutant---.

Signed and Sealed this

Sixth Day of February, 2001

Attest:

Q. TODD DICKINSON

Attesting Officer

Director of Patents and Trademarks